(12) United States Patent
Ginsberg et al.

(10) Patent No.: US 10,161,890 B2
(45) Date of Patent: Dec. 25, 2018

(54) CATHODOLUMINESCENCE-ACTIVATED NANOSCALE IMAGING

(71) Applicant: The Regents of the University of California, Oakland, CA (US)

(72) Inventors: Naomi Ginsberg, Oakland, CA (US); Connor Gregory Bischak, Berkeley, CA (US); Craig L. Hetherington, Berkeley, CA (US); David M. Kaz, Oakland, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/564,542

(22) PCT Filed: Apr. 8, 2016

(86) PCT No.: PCT/US2016/026685
§ 371 (c)(1),
(2) Date: Oct. 5, 2017

(87) PCT Pub. No.: WO2016/164751
PCT Pub. Date: Oct. 13, 2016

(65) Prior Publication Data
US 2018/0080885 A1 Mar. 22, 2018

Related U.S. Application Data

(60) Provisional application No. 62/144,767, filed on Apr. 8, 2015.

(51) Int. Cl.
*G01N 23/22* (2018.01)
*G01N 23/2254* (2018.01)

(52) U.S. Cl.
CPC ......... *G01N 23/2254* (2013.01); *G01N 23/22* (2013.01); *G01N 2223/612* (2013.01)

(58) Field of Classification Search
CPC .. G01N 23/22; G01N 23/225; G01N 23/2251; G01N 23/2254
USPC ................................................. 250/306, 307
See application file for complete search history.

(56) References Cited

U.S. PATENT DOCUMENTS

2009/0086204 A1    4/2009 Maiti et al.

OTHER PUBLICATIONS

Invitation to Pay Additional Fees received for PCT Patent Application No. PCT/US2016/026685, dated May 31, 2016, 2 pages.

(Continued)

*Primary Examiner* — Nicole Ippolito
*Assistant Examiner* — Hanway Chang
(74) *Attorney, Agent, or Firm* — Morrison & Foerster LLP

(57) ABSTRACT

Provided herein are non-invasive methods of nanoscale imaging of a sample using an illumination layer and an electron beam. For example, the electron may activate the illumination layer without activating the sample, and the illumination layer may emit cathodoluminescence to produce a nanoscale image of the sample.

23 Claims, 30 Drawing Sheets

(56) References Cited

OTHER PUBLICATIONS

International Search Report and Written Opinion received for PCT Application No. PCT/US2016/026685, dated Aug. 19, 2016, 11 pages.
International Preliminary Report on Patentability received for PCT Patent Application No. PCT/US2016/026685, dated Oct. 19, 2017, 8 pages.
Demers et al., "Three-Dimensional Electron Microscopy Simulation with the Casino Monte Carlo software", Scanning, vol. 33, No. 3, 2011, 21 pages.
Kaz et al., "Bright Cathodoluminescent Thin Films for Scanning Nano-Optical Excitation and Imaging", ACS Nano, vol. 7, No. 11, 2013, pp. 10397-10404.

CATHODOLUMINESCENCE-ACTIVATED NANOSCALE IMAGING

CROSS-REFERENCE TO RELATED APPLICATIONS

This application is a U.S. National Phase Patent Application of PCT/US2016/026685, filed Apr. 8, 2016, which claims priority to and the benefit of U.S. Provisional Patent Application No. 62/144,767, filed Apr. 8, 2015, each of which is incorporated herein by reference in its entirety.

STATEMENT REGARDING FEDERALLY-SPONSORED RESEARCH

This invention was made with government support under 1152656 awarded by the National Science Foundation and under DE-AC02-05CH11231 awarded by the U.S. Department of Energy. The government has certain rights in the invention.

FIELD

The present disclosure generally relates to nanoscale imaging, and more specifically to cathodoluminescence-activated nanoimaging of samples.

BACKGROUND

Near-field optical probes are valuable tools for the characterization of complex structures and processes in solid state materials, soft matter and biological samples that occur over length scales smaller than the wavelength of light. In variants of near-field scanning optical microscopy (NSOM), an optical probe is typically integrated with a scanning tip and rastered over a sample to form an image. Images acquired with NSOM typically require mechanical scanning and can contain artifacts from tip-sample interactions. Alternatively, in scanning electron microscopy (SEM), a focused electron beam is electronically scanned over a sample to obtain nanoscale images by correlating the detected scattered electrons with the position of the beam. Traditional electron microscopy does not use spectrally-specific excitation and can damage soft materials, such as biological samples.

Alternatively, cathodoluminescence (CL) may also be used for nanoscale imaging. Current CL methods typically detect the light generated in the sample by the application of an electron beam. CL has been used to investigate the nanoscale properties of solid luminescent materials and to characterize metallic nanostructures. Direct CL has also been used to image biological samples, but typically causes damage to the sample and can result in poor imaging quality. Methods which incorporate inorganic cathodoluminescent nanoparticle labels into a biological sample result in less sample damage, but imaging with nanoparticle labels requires the electron beam to penetrate into the sample, which precludes repeated measurements or observations of dynamics. Further, the structure of some samples, including biological and nonbiological samples, makes it difficult to attach fluorescent labels, limiting their ability to be imaged.

Thus, various methods are known in the art to image samples; however, capturing nanoscale sample dynamics is a challenge in the art. What is needed in the art are alternative methods that can achieve speed and is suitable for prolonged imaging. For example, what is needed is a method of nanoscale imaging in which electron beam damage to the sample is minimized, the sample can be imaged quickly, and the sample can be imaged multiple times.

BRIEF SUMMARY

Provided herein are cathodoluminescence-activated nanoimaging systems and methods that addresses the need in the art. The systems and methods provided can produce nanoscale images with high resolution, images of fragile samples that can be damaged by the direct electron beam contact in other methods, and be used for repeated imaging of a sample.

In one embodiment, provided is a system for imaging a sample, and the system includes:
 an illumination layer,
 a sample,
  wherein the sample is positioned below the illumination layer;
 an electron beam source,
  wherein the electron beam source is positioned above the illumination layer, and is configured to contact multiple locations of the illumination layer with an electron beam, and
  wherein the illumination layer is configured to become excited by contact with an electron beam and emit photons when excited;
 an optical detector,
  wherein the optical detector is configured to receive at least a portion of the photons emitted by the illumination layer,
   wherein the at least a portion of the photons emitted by the illumination layer and received by the optical detector are located above the illumination layer; and
 a signal correlation device,
  wherein the signal correlation device is connected to the optical detector and the electron beam source, and is configured to correlate the photons received by the optical detector with the multiple locations of the illumination layer contacted with the electron beam to produce an image of the sample.

In some variations, the illumination layer has an optical near-field of 10 nm or less, and the sample is located within the optical near-field of the illumination layer.

In some variations, the sample is configured to undergo resonant energy transfer with the excited illumination layer, and the sample emit photons. In one variation, the sample includes a biological molecule.

In certain variations, the optical detector is configured to receive at least a portion of the photons emitted by the sample; and the signal correlation device is configured to correlate the photons received by the optical detector with the multiple locations of the illumination layer contacted with the electron beam to produce the image. In other variations, the system further comprises an additional optical detector, wherein the additional optical detector is configured to receive at least a portion of the photons emitted by the sample; and the signal correlation device is connected to the additional optical detector and the electron beam source, and is configured to correlate the photons received by the additional optical detector with the multiple locations of the illumination layer contacted with the electron beam to produce an additional image of the sample.

In some variations, the electron beam source is configured to contact multiple locations of the illumination layer with an electron beam without contacting the sample with the electron beam. In certain variations, the illumination layer includes YAl$_3$O and Ce$^{3+}$. In some variations, the illumination layer is between 5 nm and 20 nm thick. In some variations, the system further includes a parabolic mirror to direct photons emitted by the illumination layer to be received by the optical detector.

Provided herein is a method for imaging a sample, and the method includes:

(i) producing an electron beam from an electron beam source;

(ii) contacting multiple locations of an illumination layer with the electron beam,
wherein the electron beam source is located above the illumination layer,
wherein a sample is located below the illumination layer,
wherein the contacting of the illumination layer with the electron beam excites least a portion of the illumination layer without exciting the sample, and
wherein at least a portion of the excited illumination layer emits photons;

(iii) detecting at least a portion of the photons emitted by the excited illumination layer,
wherein the detected photons are located above the illumination layer; and (iv) correlating at least a portion of the detected photons with the multiple locations of the illumination layer contacted with the electron beam to produce an image of the sample.

In some variations, at least a portion of the sample undergoes resonant energy transfer with the excited illumination layer, and the sample emits photons, and the method further includes collecting at least a portion of the photons emitted by the sample. In one variation, the sample includes a biological molecule.

In certain variations, steps (ii) through (iv) are repeated to produce one or more additional images of the sample over a period of time.

Provided herein is an imaging chip that includes:
an illumination layer,
wherein the illumination layer is configured to be contacted by an electron beam produced from an electron beam source positioned above the illumination layer, become excited by contact with the electron beam, and emit photons when excited;
a frame layer,
wherein the frame layer is configured to provide structural support, is positioned above the illumination layer, and has an imaging window through which an electron beam passes to contact the illumination layer without contacting the frame layer; and
a buffer layer,
wherein the buffer layer is positioned between the frame layer and the illumination layer.

In some variations, the imaging chip further includes a sample layer, wherein the sample layer is configured to hold a sample and is positioned below the illumination layer. In certain variations, the imaging chip further includes at least one additional frame layer.

Provided herein is an imaging chip that includes:
an illumination layer,
wherein the illumination layer is configured to be contacted by an electron beam produced from an electron beam source positioned above the illumination layer, become excited by contact with the electron beam, and emit photons when excited;
a sample layer,
wherein the sample layer is configured to hold a sample and is positioned below the illumination layer;
a frame layer,
wherein the frame layer is configured to provide structural support, is positioned above the illumination layer, and has an imaging window through which an electron beam passes to contact the illumination layer without contacting the frame layer;
a buffer layer,
wherein the buffer layer is positioned between the frame layer and the illumination layer.

In some variations, the illumination layer of the imaging chip includes Ce$^{3+}$ and YAlO$_3$. In certain variations, the illumination layer is between 5 nm and 20 nm thick. In other embodiments, the frame layer includes Si. In yet other variations, the imaging chip further includes an additional buffer layer, wherein the additional buffer layer is positioned between the buffer layer and the frame layer, the buffer layer includes LaAlO$_3$, and the additional buffer layer includes SrTiO$_3$. In some variations, the sample layer further includes a sample.

Provided herein is the image produced by any of the method described herein.

DESCRIPTION OF THE FIGURES

The present application can be understood by reference to the following description taken in conjunction with the accompanying figures.

DETAILED DESCRIPTION

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

Described herein are methods of cathodoluminescence-activated imaging to obtain a nanoscale image of a sample without directly contacting the sample with an electron beam. The damage caused by direct electron beam contact in other methods (e.g. scanning electron microscopy, cathodoluminescence imaging) may prevent imaging of fragile samples (e.g. biological molecules), repeated imaging of a sample, and/or observation of sample dynamics. In the cathodoluminescence-activated imaging methods described herein, an electron beam contacts the top side of an illumination layer positioned between the electron beam and the sample, without penetrating to the sample. The illumination layer is excited upon contact by the electron beam and emits photons. The photons emitted by the top side of illumination layer are collected and correlated with the location of electron beam contact with the illumination layer to produce the nanoscale image. Prior to photon emission, the excited illumination layer undergoes resonant energy transfer with the sample, which changes the rate of photon emission from the illumination layer resulting in the image contrast. Certain types of samples result in increased photon emission from the illumination layer. Other types of samples result in decreased photon emission from the illumination layer. In some embodiments, the sample also emits photons. For example, in certain embodiments, the electron beam excites the illumination layer without exciting the sample, the sample undergoes resonant energy transfer with the illumination layer, and both the sample and the illumination layer emit photons.

Figure 4:
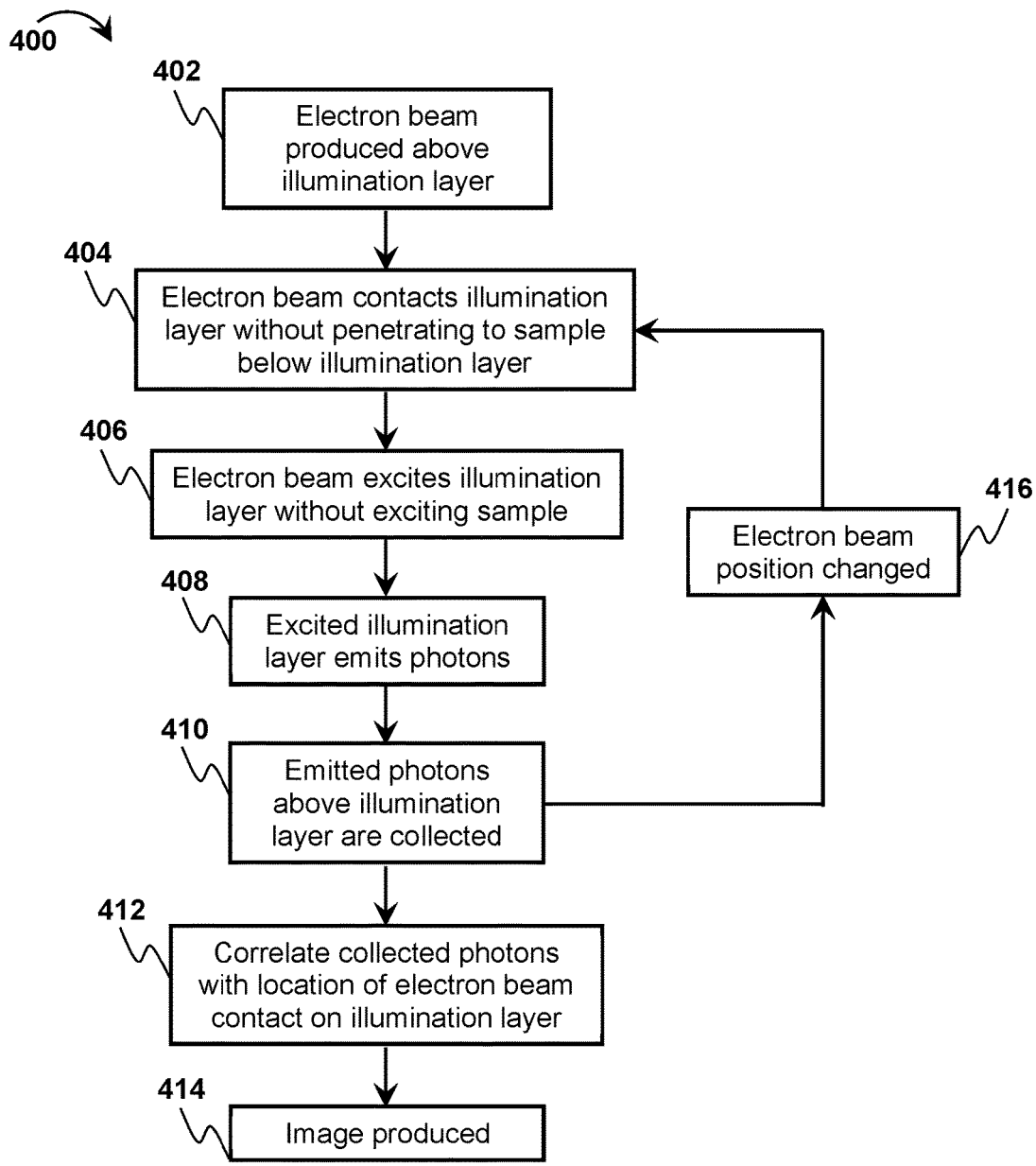
FIG. 4 is a flowchart for performing an exemplary embodiment of the imaging methods described herein.

Shown in FIG. 4 is a flowchart for performing an embodiment of the imaging methods described herein. In process 400, an electron beam is produced from a source positioned above an illumination layer in step 402. The electron beam then contacts the illumination layer in step 404 without penetrating to the sample located below the illumination layer. The electron beam excites the illumination in step 406 without exciting the sample. In step 408, the excited illumination layer emits photons, and a portion of the emitted photons above the illumination layer are collected in step 410. In step 412, the photons which were collected in step 410 are correlated with the location of electron beam contact with the illumination layer to produce the image in step 414.

To produce an image in one dimension (e.g. a linear image) or two dimensions (e.g., a square image), the position of the electron beam is changed in step 416, and steps 404 through 410 are repeated with a different part of the illumination layer. It should be understood that in certain variations, one or more steps may be added or removed from process 400.

In some variations of exemplary process 400, the process may include one or more additional steps. For example, in one variation, after step 406, the excited illumination layer excites the sample through resonant energy transfer, and the sample emits photons. In step 410, photons emitted from the illumination layer and/or the sample are collected. In such variations, the sample may be or include a biological molecule.

The cathodoluminescence-activated imaging methods described herein may be performed with an imaging chip comprising an illumination layer and one or more additional layers. For example, in certain variations, the imaging chip contains an illumination layer; one or more buffer layers positioned above the illumination layer; a frame layer to provide structural support positioned above the one or more buffer layers; and a sample layer configured to hold a sample positioned below the illumination layer. In certain embodiments, the frame layer includes an imaging window, through which the electron beam contacts the one or more buffer layers and the illumination layer without contacting the sample or the frame layer.

In some aspects, described herein are methods of nanoscale imaging of sample using an optical imaging system. In certain embodiments, the optical imaging system includes an illumination layer, a sample to be imaged and an electron beam source. The optical imaging system may further include other components, including, for example, one or more optical detectors, one or more signal correlation devices, one or more components to direct emitted photons (e.g., a parabolic mirror), or one or more optical filters (e.g., a dichroic filter), or any combinations thereof. In some embodiments, the illumination layer is included in an imaging chip.

In certain embodiments, the optical imaging system includes an illumination layer, a sample, an electron beam source, a parabolic mirror, an optical detector, and a signal correlation device. In one variation, the electron beam source is positioned above the illumination layer; the sample is positioned below the illumination layer; the parabolic mirror is positioned above the illumination layer to direct at least a portion of the emitted photons to the optical detector; and the signal correlation device is connected to the electron beam source and the optical detector. The illumination layer, sample, and electron beam source are used to perform steps 402 through 408 of process 400. Following emission of photons from the excited illumination layer in step 408, the emitted photons above the illumination layer contact the parabolic mirror and are directed to the optical detector, which collects the photons to generate a signal. The signal from the optical detector and the location of the electron beam contact with the illumination layer are correlated by the correlation device to produce the image.

Figure 3:
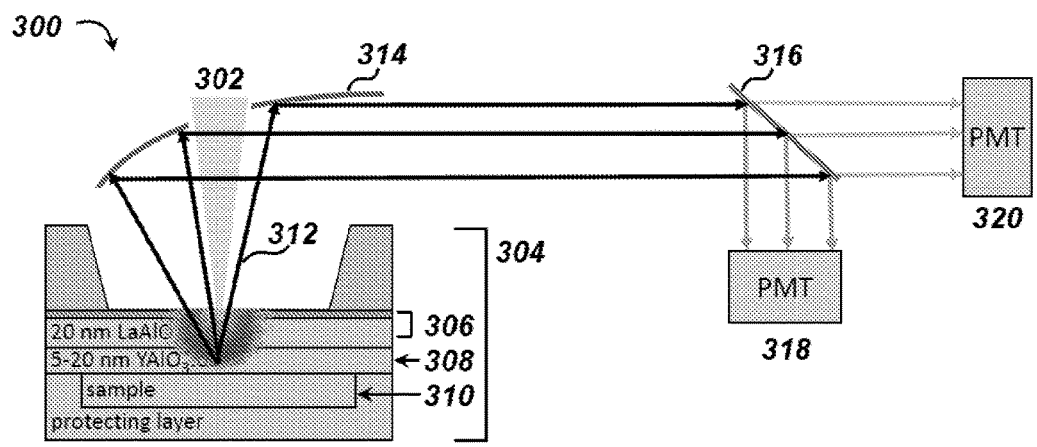
FIG. 3 is a scheme showing the use of an imaging chip with a YAP:Ce illumination layer and a sample in an optical imaging system.

FIG. 3 depicts exemplary optical system 300 which may be used in the nanoscale imaging methods described herein. In the optical system depicted, electron beam 302 is applied to imaging chip 304, which includes two buffer layers 306, illumination layer 308, and sample 310. The electron beam 302 penetrates through the buffer layers 306 and the illumination layer 308, and excites the illumination layer 308 without exciting sample 310. The illumination layer 308 undergoes resonant energy transfer with the sample 310.

Photons 312 emitted from the excited illumination layer and the sample are directed by parabolic mirror 314 to dichroic filter 316, an optical filter that transmits photons of a certain wavelength and deflects photons of other wavelengths. Dichroic filter 316 deflects photons emitted by the illumination layer to photomultiplier tube (PMT) 318. Dichroic filter 316 transmits photons emitted by the sample to PMT 320. Both PMT 318 and PMT 320 are optical detectors, which detect the photons emitted by the illumination layer and the sample, respectively.

The cathodoluminescence-activated imaging methods described herein can be used to acquire images at rates similar to other rapid imaging techniques (e.g. dark-field scattering microscopy, total internal reflection fluorescence microscopy) with higher resolution, and resolve nanoscale features in samples that cannot be imaged using traditional electron microscopy due to damage from direct electron excitation.

The systems, methods, chips, and images are described in further detail below.

Optical Imaging System

The methods described herein may be performed using an optical imaging system. In certain embodiments, the optical imaging system includes an illumination layer, a sample to be imaged and an electron beam source. The optical imaging system may further include other components, including, for example, one or more optical detectors, one or more signal correlation devices, one or more components to direct emitted photons (e.g., a parabolic mirror), or one or more optical filters (e.g., a dichroic filter), or any combinations thereof.

As described above, FIG. 3 depicts exemplary optical system 300 which may be used in the nanoscale imaging methods described herein. It should be understood that in other variations, exemplary optical system 300 may include additional components, fewer components, or different combinations of components. For example, in some variations, exemplary optical system 300 includes a signal correlation device connected to the electron beam source and the optical detectors, to correlate the location of electron beam contact with the illumination layer with the signal from each of optical detectors 318 and 320. In other variations, exemplary optical system 300 does not include dichroic filter 316. In some variations, exemplary optical system 300 does not have optical detector 320 to detect photons emitted by the sample. In certain variations, exemplary optical system 300 includes dichroic filter 316; optical detector 318, to detect photons emitted by the illumination layer; a signal correlation device connected to the electron beam source and the one optical detector 318, to correlate the location of electron beam contact with the illumination layer with the signal from optical detector 318; and does not include optical detector 320.

Electron Beam Source

Any suitable electron beam source capable of producing an electron beam to excite the illumination layer may be used in the methods described herein. In some variations, the electron beam source is capable of scanning the illumination layer with the electron beam. For example, in certain variations the electron beam source is capable of scanning the illumination layer with an electron beam in a two-dimensional pattern (e.g., a raster scan). In some variations, the electron beam source may include components necessary to condense and direct an electron beam to contact the illumination layer. For example, an electron beam source may include an electron gun, one or more condenser lenses, and one or more deflection coils.

In some variations, the electron beam source produces an electron beam with an accelerating voltage between 0.4 kV and 4.0 kV, between 1.0 kV and 3.6 kV, between 1.0 kV and 2.8 kV, or between 1.6 and 2.2 kV. In certain variations, the electron beam produced has an accelerating voltage of 0.8 kV, 1.0 kV, 1.2 kV, 1.4 kV, 1.6 kV, 1.8 kV, 2.0 kV, 2.2 kV, 2.4 kV, 2.6 kV, 2.8 kV, 3.0 kV, 3.2 kV, 3.4 kV, 3.6 kV, 3.8 kV, 4.0 kV, 4.2 kV, 4.4 kV, 4.6 kV, 4.8 kV, or 5.0 kV. In some variations, the accelerating voltage of the electron beam produced is selected such that the electron beam excites the illumination layer without penetrating to the sample. In some variations, the accelerating voltage of the electron beam produced is selected such that the electron beam excites the illumination layer without exciting the sample. In some variations, the accelerating voltage of the electron beam produced is selected such that the electron beam excites the illumination layer without damaging the sample. In certain variations, the accelerating voltage of the electron beam produced is selected based on the thickness of the illumination layer, the presence of one or more buffer layers the presence of one or more additional layers, the type of sample, the image contrast desired, or the image resolution desired, or any combinations thereof.

Optical Detector

Any suitable optical detector capable of detecting photons may be used in the methods described herein. In some variations the optical detector is a photomultiplier tube. In other variations, the optical detector is a spectrometer. In other variations, the optical detector is an avalanche photodiode. In certain embodiments, the optical imaging system includes one optical detector, while in other embodiments the optical imaging system includes more than one optical detector. In some embodiments, the optical imaging system includes a first optical detector configured to detect photons emitted by the illumination layer, and a second optical detector configured to detect photons emitted by the sample.

Signal Correlation Device

The signal correlation device is connected to the electron beam source and at least one optical detector, and is configured to correlate the signal from at least one optical detector with the location of electron beam contact with the illumination layer to produce a nanoscale image. In certain embodiments, the signal correlation device is connected to more than on optical detector, and is configured to correlate the signal from each optical detector to which it is connected with the location of electron beam contact with the illumination layer to produce at least one nanoscale image. In certain variations, a separate nanoscale image is produced for each optical detector to which the correlation device is connected. For example, referring to FIG. 3, the optical imaging system 300 includes optical detector 318 to detect photons emitted from the illumination layer, and optical detector 320 to detect photons emitted from the sample. In one variation, the optical imaging system 300 also contains a signal correlation device; the signal correlation device is connected to the electron beam source, optical detector 318, and optical detector 320; and the correlation device produces a first nanoscale image correlating the signal from optical detector 318 with the location of electron beam contact with the illumination layer, and a second nanoscale image correlating the signal from optical detector 320 with the location of electron beam contact with the illumination layer.

Component to Direct Emitted Photons

Any suitable component capable of directing emitted photons may be used in the methods described herein. In one embodiment, the component to direct emitted photons is a parabolic mirror. The parabolic mirror may be constructed from any appropriate material, including, for example, Al.

It is understood that any description of the optical imaging system for use in the methods described herein may be combined with any descriptions of the any other embodiments the same as if each and every combination were individually listed.

Imaging Chip

In certain embodiments, the illumination layer used in the methods described herein is part of an imaging chip, which may include one or more other layers. For example, in certain variations, the imaging chip contains an illumination layer; one or more buffer layers; one or more frame layers; and a sample layer. In some variations, the imaging chip includes one or more additional layers, including, for example, mask layers used during construction of the imaging chip.

Figure 1:
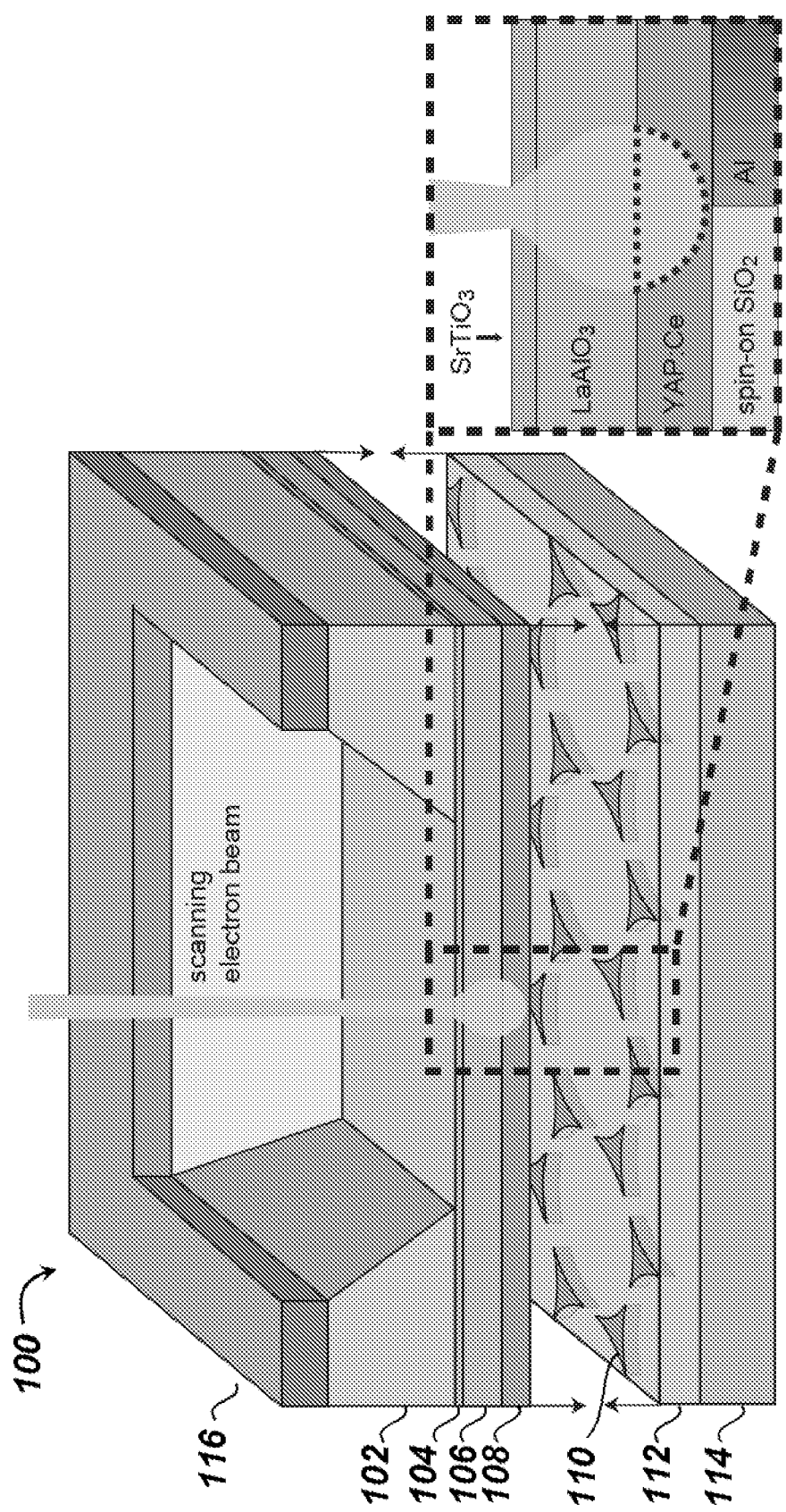
FIG. 1 is a diagram of an imaging chip including a cerium-doped yttrium aluminum perovskite (YAP:Ce) scintillator film illumination layer and a sample of Al nanostructures. The inset depicts penetration of an electron beam into the imaging chip.

Depicted in FIG. 1 is one exemplary embodiment of an imaging chip which may be used in the methods described herein, comprised of multiple layers, each with a top side and a bottom side. As depicted, imaging chip 100 includes illumination layer 108 comprising $YAlO_3$ with a perovskite structure and $Ce^{3+}$ dopants. In some embodiments, the illumination layer comprises 15 nm of $YAlO_3$ with a perovskite structure and $Ce^{3+}$ dopants. Contacting the top side of illumination layer 108 is a first buffer layer 106. In some embodiments, the first buffer layer comprises $LaAlO_3$. In certain embodiments, the first buffer layer comprises 20 nm of $LaAlO_3$. Contacting the top side of the first buffer layer 106 is a second buffer layer 104. In some embodiments, the second buffer layer comprises $SrTiO_3$. In certain embodiments, the second buffer layer comprises five unit cells of $SrTiO_3$. Contacting the top side of the second buffer 104 is frame layer 102, comprising Si. In some variations, the frame layer comprises 200 μm of Si. Frame layer 102 includes an imaging window through which an electron beam can pass to contact the one or more buffer layers and illumination layer without contacting the frame layer. Positioned below illumination layer 108 is imaging sample 110. In some variations, imaging sample 110 comprises Al nanoparticles. Imaging sample 110 is encased in sample layer 112. In certain variations, sample layer 112 comprises $SiO_2$. Imaging chip 100 also includes additional layers 114 and 116. Additional layer 114 contacts the bottom side of sample layer 112. In certain embodiments, additional layer 100 comprises ProTEK® B3 protective coating. Additional layer 116 contacts the top side of frame layer 102. In some embodiments, additional layer 116 comprises silicon nitride (e.g., $Si_3N_4$) used as a mask layer during construction of the imaging chip. In some variations, the additional layer comprises 1 μm of silicon nitride (e.g., $Si_3N_4$) used as a mask layer during construction of the imaging chip.

It should be understood that variations of the imaging chip depicted in FIG. 1 may include added layers or fewer layers in some embodiments. For example, some variations of imaging chip 100 may include one or more added buffer layers. In some variations of imaging chip 100, both buffer layers 104 and 106 are absent. In other variations, imaging chip 100 includes only one buffer layer. In yet other variations, frame layer 102 is absent. In one variation of the chip, sample 110 is absent. In certain variations, buffer layers 104 and 106 are absent, sample 110 is absent, sample layer 112 is absent, and additional layers 114 and 116 are absent, and a least a portion of illumination layer 108 is not contacted by any other layers.

Figure 20:
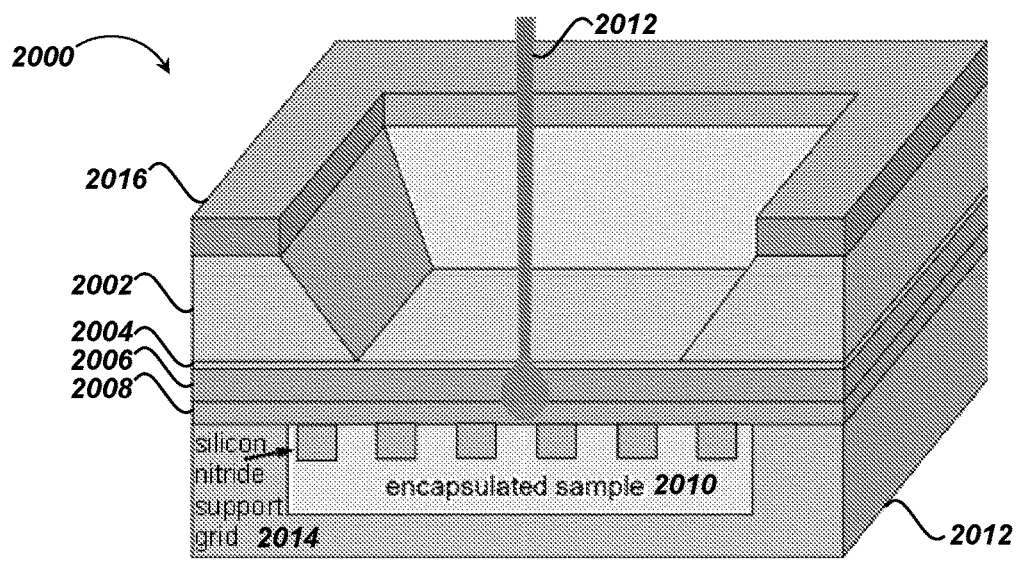
FIG. 20 is a diagram of an imaging chip produced using a wet-etch method with a YAP:Ce scintillator film illumination layer.

Depicted in FIG. 20 is another exemplary embodiment of an imaging chip which may be used in the methods described herein, wherein the encapsulated sample may be a liquid. As depicted, imaging chip is 2000 includes illumination layer 2008 comprising $YAlO_3$ with a perovskite structure and $Ce^{3+}$ dopants. In some embodiments, the illumination layer comprises 15 nm of $YAlO_3$ with a perovskite structure and $Ce^{3+}$ dopants. Contacting the top side of illumination layer 2008 is a first buffer layer 2006, comprising of $LaAlO_3$. In some embodiments, the first buffer layer comprises 20 nm of $LaAlO_3$. Contacting the top side of the first buffer layer 2006 is a second buffer layer 2004, comprising $SrTiO_3$. In some embodiments, the second buffer layer comprises five unit cells of $SrTiO_3$. Contacting the top side of the second buffer layer 2004 is frame layer 2002, comprising Si. In some embodiments, the frame layer comprises 200 μm of Si. Frame layer 2002 includes an imaging window through which an electron beam can pass to contact the one or more buffer layers and illumination layer without contacting the frame layer. Positioned below illumination layer 2008 is a second frame layer 2014, which contacts at least a portion of the illumination layer. In some embodiments, this second frame layer comprises silicon nitride. In certain embodiments, this second frame layer is a support grid. In some embodiments, the silicon nitride support grid 2014 has a structure wherein portions of the illumination layer are contacted by the support grid, while other portions are not contacted by the support grid, and these two portions occur in a regular pattern. For example, in some embodiments, the silicon nitride support grid 2014 comprises a periodic pattern of circular holes. In other variations, the additional frame layer 2014 is a support grid that does not comprise silicon nitride. Imaging sample 2010 contacts the illumination layer, and is encapsulated by polymer layer 2012. In some embodiments, imaging sample 2010 is a liquid. Imaging chip 2000 also includes additional layer 2016. Additional layer 2016 contacts the top side of frame layer 2002, and comprises 1 μm of silicon nitride (e.g., $Si_3N_4$) used as a mask layer during construction of the imaging chip.

In certain embodiments, at least a portion of the illumination layer is contacted by no other layers that are configured to provide support. Thus, in such embodiments, at least a portion of the illumination layer is free-standing. In certain embodiments, at least a portion of the illumination layer is free-standing, and a separate portion of the illumination layer is contacted by a sample layer. In still other embodiments, at least a portion of the illumination layer is free-standing, and a separate portion of the illumination layer is contacted by a frame layer and a sample layer. In certain embodiments, at least a portion of the illumination layer is free-standing, and a separate portion of the illumination layer is contacted by a sample. In certain embodiments, at least a portion of the illumination layer is free-standing, and the at least a portion of the free-standing illumination layer is contacted by a sample. In some embodiments, the free-standing illumination layer is able to withstand the pressure differential of being exposed to a vacuum environment (for example, in an SEM) on at least a portion of one side and contacting a sample on at least a portion of the other side without the illumination layer being damaged (e.g., breaking).

The imaging chip as described herein may be any thickness suitable to be used in the methods of imaging described herein. For example, in some embodiments the imaging chip is between 5 nm to 100 nm thick. In certain embodiments, the thickness of the imaging chip may be related to the accelerating voltage needed for the electron beam to excite the illumination layer without penetrating into the sample.

Using a higher accelerating voltage may, in some variations, impact the spatial resolution of the obtained image. Thus, in some embodiments, a thinner imaging chip may be used with a lower accelerating voltage. In certain embodiments, using a thinner imaging chip with a lower accelerating voltage achieves a better spatial resolution in the resulting image.

Illumination Layer

The illumination layer used in the methods described herein may be any suitable layer which can undergo photon emission upon activation by an electron beam. In some embodiments, the illumination layer is a scintillator film, wherein the scintillator film emits photons when excited by electrons from the application of an electron beam.

In certain embodiments, the sample is positioned below the illumination layer, and the electron beam source is above the illumination layer. In certain variations, the electron beam excites at least a portion of the illumination layer without penetrating the sample, and at least a portion of the excited illumination layer emits photons. In certain variations, the electron beam excites at least a portion of the illumination layer without exciting the sample, and at least a portion of the excited illumination layer emits photons. In yet other variations, the electron beam excites at least a portion of the illumination layer without damaging the sample, and at least a portion of the excited illumination layer emits photons.

At least a portion of the photons emitted by the illumination layer are detected to produce the nanoscale image of the sample. In certain variations, the sample is positioned below the illumination layer, at least a portion of the illumination layer emits photons, and at least a portion of the emitted photons are detected above the illumination layer to produce the nanoscale image of the sample.

In some variations, the illumination layer includes an alkali metal, an alkali earth metal, a transition metal, a lanthanide, or any combinations thereof. In certain variations, the illumination layer includes yttrium, aluminum, lithium, sodium, potassium, rubidium, cesium, beryllium, magnesium, calcium, strontium, barium, scandium, titanium, vanadium, chromium, manganese, iron, cobalt, nickel, copper, zinc, zirconium, niobium, molybdenum, technetium, ruthenium, rhodium, palladium, silver, cadmium, tungsten, iridium, platinum, aluminum, gallium, indium, tin, thallium, lead, bismuth, lanthanum, cerium, praseodymium, neodymium, samarium, europium, gadolinium, terbium, dysprosium, holmium, erbium, thulium, ytterbium, or lutetium, or any combinations thereof. In certain variations, the illumination layer includes yttrium and aluminum.

In some embodiments, the illumination layer includes a metal oxide. In certain variations, the illumination layer includes an aluminum oxide. In some variations, the illumination layer includes a yttrium aluminum oxide. In certain variations, the illumination layer includes $YAlO_3$.

In some embodiments, the illumination layer includes silicon, sulfur, nitrogen, oxygen, fluorine, chlorine, bromine, iodine, or any combination thereof. In certain embodiments, the illumination layer includes silicon nitride (e.g., $Si_3N_4$).

In some embodiments, the illumination layer further includes one or more dopants, which may alter the electrical or optical properties of the illumination layer. For example, in certain embodiments, the addition of one or more dopants to an illumination layer may alter the photon emission of the illumination layer, compared to an illumination layer without the one or more dopants. In some embodiments, the one or more dopants is selected from cerium, neodymium, chromium, erbium, ytterbium, holmium, thulium, dysprosium, samarium, terbium, and gadolinium. In certain embodiments of the methods described herein, the illumination layer further includes cerium dopants. In some embodiments, the illumination layer includes $Ce^{3+}$ dopants. In some embodiments, the illumination layer includes lumophores (e.g., $Ce^{3+}$ dopants).

In certain embodiments, the illumination layer includes $YAlO_3$ with a perovskite structure and $Ce^{3+}$ dopants.

In yet other embodiments, the illumination layer includes an organic scintillating compound.

In some embodiments, the illumination layer is a thin film, wherein the thin film is a layer of material from 1 nm to 10 μm thick. In certain embodiments, the illumination layer is between 1 nm to 100 nm thick, between 1 nm to 80 nm thick, between 1 nm to 60 nm thick, between 1 nm to 40 nm thick, between 1 nm to 20 nm thick, or between 5 nm to 20 nm thick. In certain embodiments, the illumination layer is 4.3 nm thick, 15 nm thick, 18 nm thick, or 46 nm thick. In one embodiment, the illumination layer is 18 nm thick. In certain embodiments, the illumination layer is from 1 nm to 500 nm thick. In certain embodiments, the illumination layer is from 15 nm to 20 nm thick. In one embodiment, the illumination layer is 15 nm thick.

In some embodiments, the illumination layer has a single photon emission peak, while in other embodiments, the illumination layer has more than one photon emission peak. In certain embodiments, the illumination layer has a single photon emission peak centered at about 370 nm.

In some embodiments, the illumination layer has a photoluminescence lifetime of at least 2 ns, at least 4 ns, 6 ns, at least 8 ns, at least 10 ns, at least 12 ns, at least 14 ns, at least 16 ns, at least 18 ns, at least 20 ns, at least 22 ns, at least 24 ns, at least 26 ns, at least 28 ns, or at least 30 ns. In some embodiments, the illumination layer has a photoluminescence lifetime between 1 ns and 1000 ns. In some embodiments, the illumination layer has a photoluminescence lifetime between 1 microsecond to 10 milliseconds, between 1 microsecond to 5 milliseconds, or between 1 microsecond to 1 millisecond.

In some embodiments, the illumination layer is spatially uniform. Spatial uniformity can be determined, for example, by activating the illumination layer with an electron beam in the absence of a sample, collecting at least a portion of the photons emitted from the illumination layer, converting the collected photons to an image, measuring the number of photons detected to produce each pixel of the image, and calculating the standard deviation of the average counts per pixel. In some variations, the standard deviation of the average counts per pixel is less than 20%, less than 15%, less than 10%, or less than 5%. In one variation, the standard deviation is less than 8%.

In some embodiments, at least a portion of the illumination layer is crystalline. In certain embodiments, at least a portion of the illumination layer is crystalline, and at least a portion of the crystalline region has a perovskite structure. In some variations, the illumination layer includes $YAlO_3$ with a perovskite structure.

The rate of photon emission from the illumination layer may depend on illumination layer thickness, crystallinity, the presence of dopants, the type of sample, and/or the accelerating voltage of the electron beam exciting the illumination layer.

Sample Layer

In some embodiments, a sample is introduced into a sample layer configured to hold the sample. In other embodiments, a sample can be introduced into the chip, and the sample layer is absent.

In some variations, the sample layer is configured to hold a single sample, while in other variations the sample layer is configured to hold multiple samples. For example, in certain variations, a single sample layer includes multiple segments, each of which is configured to hold a separate sample.

In some embodiments, at least a portion of the sample layer contacts at least a portion of the illumination layer. For example, referring to FIG. 1, at least a portion of the sample layer 112 contacts at least a portion of the illumination layer.

In other embodiments, the sample layer does not contact the illumination layer.

In some embodiments, at least a portion of the sample layer contacts at least a portion of the sample. For example, referring again to FIG. 1, in one embodiment, at least a portion of the sample 110 is contacted by the sample layer 112.

In other embodiments, the sample layer does not contact the sample. For example, in one variation, the sample is a polynucleotide bound to the surface of the illumination layer, the polynucleotide is in an aqueous solution, and the sample layer contacts the aqueous solution without contacting the bound polypeptide sample. In another variation, the sample includes polypeptides, the polypeptides are in an aqueous solution, the sample layer contacts the aqueous solution, and a portion of the polypeptides are contacted by the sample layer while a portion of the polypeptides are not contacted by the sample layer.

In certain variations, the sample layer is configured to sequentially hold more than one sample. For example, in some variations, a first sample is introduced into the sample layer, the first sample is imaged using the methods described herein, the first sample is removed from the sample layer, and a second sample is introduced into the sample layer.

In some variations, the sample layer is configured such that one or more samples are introduced into the sample layer in a continuous manner. For example, in certain variations, an aqueous solution including one or more samples is continuously flowed through the sample layer.

In some variations, the sample layer is configured to hold one or more samples while one or more additional samples are introduced into the sample layer in a continuous manner. For example, in certain variations, the sample layer holds one or more biological molecule samples and an aqueous solution including one or more additional biological molecule samples is continuously flowed through the sample layer.

The sample may be introduced into the sample layer using any appropriate methods known in the art, including, for example, spin coating, electron-beam evaporation, microfluidics, and/or injection.

Any suitable material may be used to construct the sample layer. For example, in some embodiments, the sample layer comprises $SiO_2$. In other embodiments, the sample layer comprises a polymer. In still other embodiments, the sample layer does not comprise a polymer.

Figure 26:
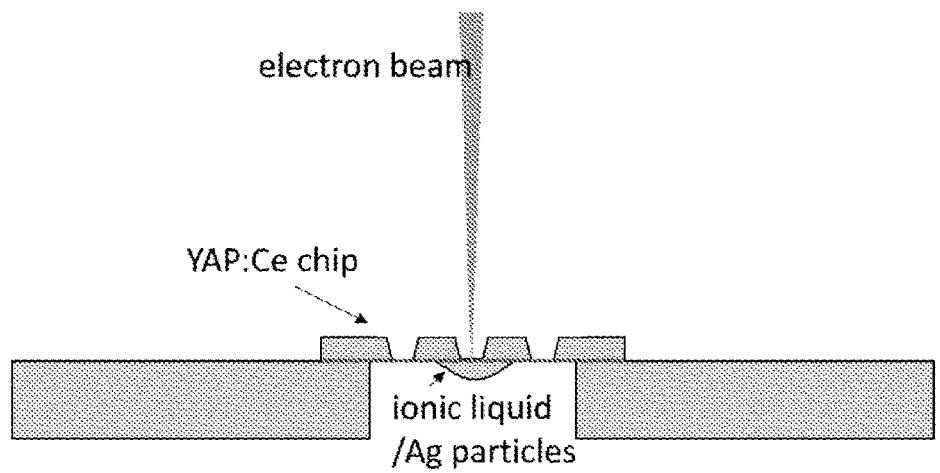
FIG. 26 depicts a schematic of the imaging configuration for metal particles in a droplet of liquid on the bottom face of a scintillating illumination layer, with the electron beam incident on a window in the imaging chip.

In some variations, the sample layer is absent. For example, shown in FIG. 26 is a scheme of the imaging configuration for an imaging chip comprising a sample of Ag particles suspended in an ionic liquid, wherein the imaging chip does not include a sample layer. In some embodiments, an imaging chip as described herein may be used to image a sample in a liquid, or a liquid sample, even when the liquid is not encapsulated (for example, is not surrounded by a sample layer or graphene).

Buffer Layer

The buffer layer is a layer that promotes the formation of the illumination layer. In some embodiments, the buffer layer promotes the formation of a crystalline illumination layer. In some embodiments, the buffer layer provides structural support for the illumination layer. In some embodiments, the buffer layer includes lanthanum, aluminum, oxygen, strontium, or titanium, or any combination thereof. In certain embodiments, the buffer layer includes $LaAlO_3$, while in other embodiments, the buffer layer includes $SrTiO_3$. In certain embodiments, there is more than one buffer layer, and the buffer layers include $LaAlO_3$ and $SrTiO_3$. In some embodiments, at least a portion of the buffer layer contacts at least a portion of the illumination layer. In other embodiments, the buffer layer does not contact the illumination layer. In yet other embodiments, there is more than one buffer layer, and at a least a portion of one buffer layer contacts at least a portion of the illumination layer, while another buffer layer does not contact the illumination layer. With reference to the imaging chip depicted in FIG. 1, in one embodiment a first buffer layer 106 comprising $LaAlO_3$ is positioned between the illumination layer 108 and a second buffer layer 104 comprising $SrTiO_3$. In the embodiment depicted in FIG. 1, the second buffer layer 104 does not contact the illumination layer.

Frame Layer

The frame layer is a layer that provides structural support to the illumination layer. The frame layer may include any suitable material that provides structural support. In one embodiment, the frame layer includes silicon. In another embodiment, the frame layer includes alumina. In another embodiment, the frame layer includes silicon nitride. In another embodiment, the frame layer comprises Si, $Al_2O_3$, or $Si_3N_4$, or any combinations thereof.

At least a portion of the frame layer may contact at least a portion of the illumination layer, sample layer, sample, buffer layer, or additional layer, or any combinations therein. In one variation, at least a portion of the frame layer contacts at least a portion of the illumination layer. In other variations, the frame layer does not contact the illumination layer. In some variations, the illumination layer is contacted by a buffer layer, and the frame layer contacts the buffer layer without contacting the illumination layer. In certain variations, the imaging chip comprises more than one frame layer. In some embodiments, the imaging chip comprises more than one frame layer, and at least a portion of the first frame layer contacts at least a portion of the second frame layer. In some embodiments, the imaging chip comprises a frame layer that is a grid. In certain embodiments, the imaging chip comprises a frame layer that is a support grid.

Referring again to FIG. 1, imaging chip 100 includes frame layer 102 which contacts at least a portion of a second buffer layer 104 and additional layer 116 without contacting illumination layer 108, sample 110, or sample layer 112.

In some variations, the frame layer includes an imaging window through which the electron beam passes to contact the illumination layer, without the electron beam contacting the frame layer. The frame layer may contain one or more imaging windows. In other variations, the frame layer does not contain an imaging window, and the frame layer is contacted by the electron beam. In yet other variations, the frame layer does not contain an imaging window, and the frame layer is not contacted by the electron beam. Referring again to FIG. 22, imaging chip 2222 includes a frame layer comprising silicon with a plurality of imaging windows etched in step 2212. In some embodiments, the imaging windows are 10 μm in diameter.

In some variations, the imaging chip comprises one or more frame layers. In one variation, the imaging chip comprises a frame layer that contacts at least a portion of the illumination layer and an additional frame layer that contacts at least a portion of a buffer layer. In certain variations, the imaging chip comprises a frame layer that contacts at least a portion of the illumination layer, a first additional frame layer that contacts at least a portion of a buffer layer, and a second additional frame layer that contacts at least a portion of the first additional frame layer. In some embodiments, at least one of the one or more frame layers comprises a periodic array of imaging windows. In certain embodiments, an imaging chip with a periodic array of imaging windows will have a greater total area of free-standing illumination layer than an imaging chip wherein the imaging windows are not in a periodic array. For example, in certain variations, the imaging chip comprises a frame layer that contacts at least a portion of a buffer layer, wherein the frame layer comprises a regular pattern of imaging windows. In some variations, the imaging windows are square, while in other variations the imaging windows are circular. In some embodiments, circular imaging windows result in less stress to the illumination layer than windows with corners (e.g., square or rectangular windows). Thus, in some variations, circular windows may result in greater mechanical stability of the illumination layer, and may reduce illumination layer breakage in a chip.

Figure 22:
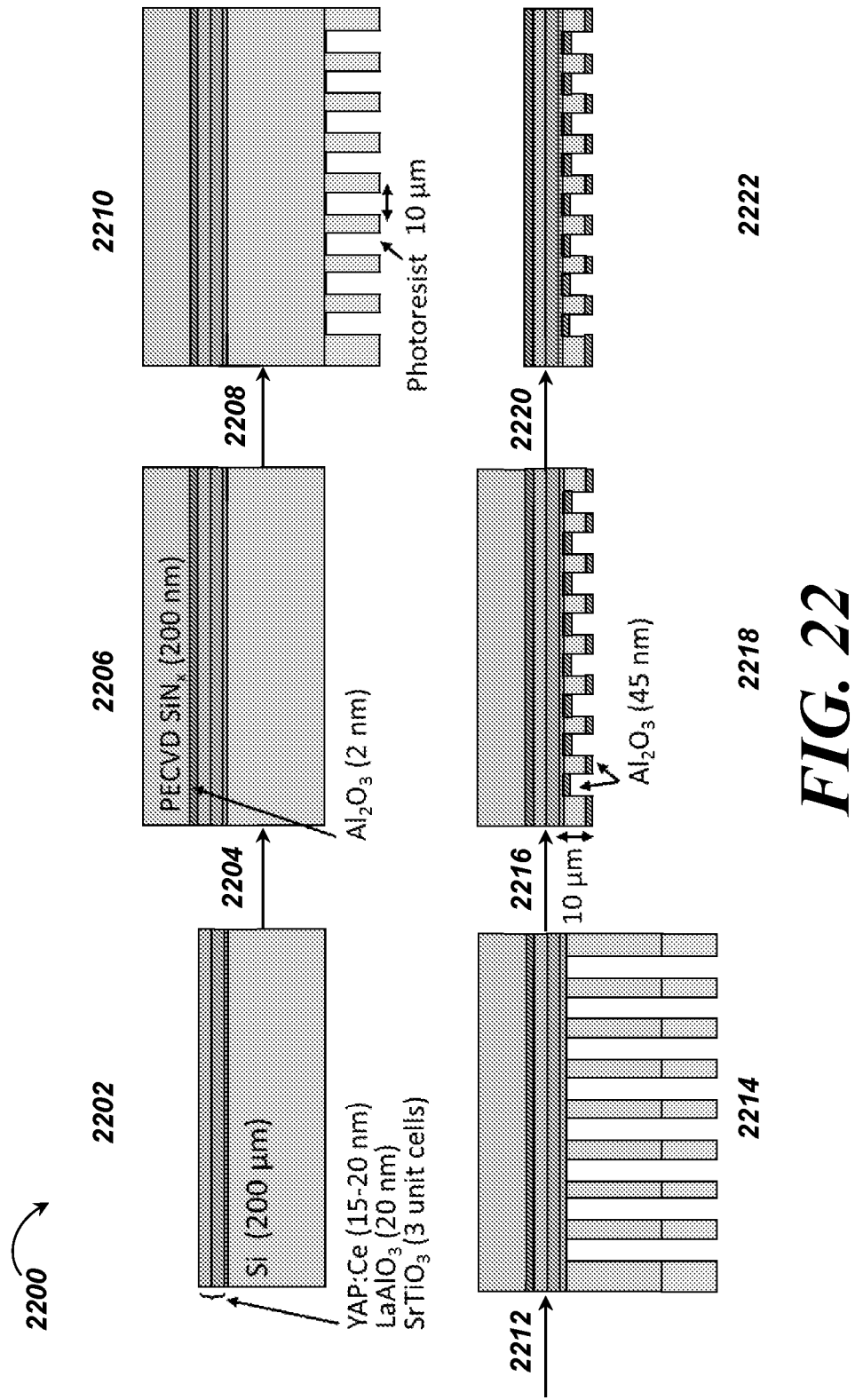
FIG. 22 is a scheme to construct an imaging chip with a YAP:Ce scintillator film illumination layer using a dry-etch method

For example, with reference to FIG. 22, imaging chip 2222 includes a frame layer of $Al_2O_3$ deposited on the YAP:Ce layer in step 2204, a frame layer of Si comprising imaging windows contacting the $SrTiO_3$ layer, and a frame layer of $Al_2O_3$ deposited on the Si layer and $SrTiO_3$ layers for structural support in step 2216. With reference to FIG. 20, imaging chip 2000 includes a frame layer 2014 comprising silicon nitride, wherein frame layer 2014 is a grid providing support.

Additional Layers

One or more additional layers may include, for example, a protective layer used in the production of the illumination layer and/or imaging chip. In some embodiments, an additional layer protects at least a portion of one or more layers from modification during the production of the illumination layer and/or imaging chip. For example, with reference to FIG. 1, imaging chip 100 includes a first additional layer 116 comprising silicon nitride (e.g., $Si_3N_4$) and a second additional layer 114 comprising ProTEK® B3.

Sample

Any suitable sample may be imaged using the methods described herein. The sample may include, for example, organic material or inorganic material, or a combination thereof.

In one embodiment, the sample comprises a soft material. In one embodiment, the sample includes organic material. In some embodiments, the soft material is an organic material (e.g., biological or an organic polymer). In some variations, the soft material is biological. In some variations, the soft material is a polymer. For example, in some variations the sample includes an organic polymer. In one variation, the sample includes polyfluorene (PFO) or poly(9,9-dioctylfluorene-alt-benzothiadiazole) (F8BT), or a combination thereof.

In other variations, the sample includes one or more biological molecules. For example, in some variations, the sample includes one or more polypeptides, one or more polynucleotides, one or more lipids, or one or more lipid membranes, or any combinations thereof. In one variation, the sample includes DNA. In another variation, the sample includes RNA. In another variation, the sample includes one or more enzymes. In yet another variation, the sample includes one or more membrane proteins. In some variations, the sample includes at least a portion of a chloroplast. For example, in one variation, the sample includes at least a portion of a thylakoid membrane. In another variation, the sample includes chlorophyll-containing lipid membrane grana stacks from chloroplasts. In yet another variation, the sample includes DNA and one or more enzymes. In yet another variation, the sample includes one or more lipid membranes and one or more membrane proteins. In certain variations, the sample includes one or more membrane proteins, and the one or more membrane proteins are enzymes.

In some embodiments, at least a portion of the one or more biological molecules has been modified. In some variations, at least a portion of the one or more biological molecules has been modified to include a synthetic tag, including, for example, one or more synthetic fluorophores (e.g., fluorescein-based tags, rhodamine-based tags) or one or more quantum dots. In other variations, at least a portion of the one or more biological molecules has been modified to include a biological tag, including, for example, a fluorescent protein (e.g., green fluorescent protein (GFP), yellow fluorescent protein (YFP)). In other variations, at least a portion of the one or more biological molecules has been modified to include a combination of one or more synthetic tags and one or more biological tags.

In another embodiment, the sample is an inorganic material. For example, in one variation the sample is Al. In another variation, the sample comprises Ag.

The sample may be a solid, a liquid, or a solution, or any combination thereof. For example, in some variations, the sample includes one or more solid Al nanostructures, while in other variations the sample includes one or more solid polymers. The sample may also be bound to a solid, suspended in a liquid, dissolved in a liquid, suspended in a solution, dissolved in a solution, or any combination thereof. For example, in some variations, the sample includes an aqueous solution containing one or more biological molecules. In one variation, the sample includes an aqueous solution containing one or more polypeptides and one or more polynucleotides. In another variation, the sample includes one or more biological molecules at least partially enclosed by an ionic liquid. In another variation, the sample includes one or more metal particles at least partially enclosed by an ionic liquid. In one variation, the sample includes one or more polymer particles suspended in oil. In another variation, the sample includes one or more polymer particles at least partially enclosed by oil. In other embodiments, the sample is at least partially enclosed by glass. For example, in some embodiments, sample is deposited on the illumination layer and glass is deposited on top of the sample. In certain embodiments, the sample is fully enclosed by glass. In some embodiments, the sample is exposed to a vacuum environment in the SEM.

In some embodiments, at least partially enclosing the sample in a liquid (for example, ionic liquid or an aqueous environment) or glass may assist in matching the index of refraction of the surroundings with that of the sample. In some embodiments, exposing the sample to vacuum may lead to a mismatch in indices of refraction, which may make it more difficult to observe via FRET contrast. In some embodiments, the sample is fully enclosed by an ionic liquid, aqueous environment, or an oil, or any combinations thereof.

Any suitable liquid may be used with the imaging chip as described herein. For example, in some embodiments, the sample is at least partially enclosed by a liquid comprising an ionic liquid, for example, sample suspended in ionic liquid or sample bound to the illumination layer and covered by an ionic liquid. In some variations, the ionic liquid does not display UV fluorescence. In certain variations, system is configured such that at least a portion of the ionic liquid remains liquid at the pressures used during imaging of the chip, for example in an SEM. A skilled artisan would recognize how to select an ionic liquid with a suitable vapor pressure to achieve this. In some variations, the ionic liquid is 1-butyl-3-methylimidazolium hexafluorophosphate, 1-butyl-3-methylimidazolium iodide, or 1-ethyl-3-methylimidazolium ethyl sulfate, 1-butyl-1-methylpyrrolidinium bis(trifluoromethylsulfonyl)imide, or 1-butyl-3-methylimidazolium acetate, or any combinations thereof. In certain variations, the ionic liquid is 1-butyl-3-methylimidazolium hexafluorophosphate, 1-butyl-3-methylimidazolium iodide, or 1-ethyl-3-methylimidazolium ethyl sulfate, or any combinations thereof. In one embodiment, the ionic liquid is 1-butyl-3-methylimidazolium hexafluorophosphate.

In some variations, the sample is at least partially enclosed by a liquid comprising an oil, for example a sample suspended in an oil or sample bound to the illumination layer and covered by an oil. In certain variations, the oil does not display UV fluorescence. In certain variations, system is configured such that at least a portion of the oil remains liquid at the pressures used during imaging of the chip, for example in an SEM. A skilled artisan would recognize how to select an ionic liquid with a suitable vapor pressure to achieve this. For example, in one variation, the oil has a vapor pressure of $1.0 \times 10^{-3}$ at 100° C., $1 \times 10^{-8}$ at 20° C., or less than $1 \times 10^{-6}$. In one variation, the oil is Edwards Ultragrade® 19.

In some variations, the sample is at least partially enclosed by an aqueous liquid, for example a sample suspended in an aqueous liquid or sample bound to the illumination layer and covered by an aqueous liquid. In certain variations, system is configured such that at least a portion of the aqueous liquid remains liquid at the pressures used during imaging of the chip, for example in an SEM. A skilled artisan would recognize how to select an aqueous liquid with a suitable vapor pressure to achieve this. For example, in certain embodiments, the aqueous liquid further comprises glycerol.

In certain variations, the sample is at least partially enclosed by an aqueous liquid, and the aqueous liquid is at least partially enclosed by an encapsulant. In some variations, the sample comprises an aqueous liquid, and the aqueous liquid is at least partially enclosed by an encapsulant. Any suitable encapsulant may be used, for example, such that at least a portion of the aqueous liquid remains liquid at the pressures used during imaging of the chip. In some variations, the encapsulant is a non-aqueous liquid. For example, in certain embodiments, the sample is deposited on the illumination layer, an aqueous liquid is applied to the sample, and then an ionic liquid encapsulant is applied to the aqueous liquid. In some variations, the encapsulant is an ionic liquid or an oil. In other variations, the encapsulant is a solid. For example, in certain embodiments, a sample comprising an aqueous liquid is deposited on the illumination layer and a graphene encapsulant is applied to the aqueous liquid such that at least a portion of the aqueous liquid is at least partially enclosed by the graphene. In some embodiments, the encapsulant is graphene, a polymer (such as polydimethylsiloxane (PDMS)), or a microfluidic structure.

In some variations, at least a portion of the sample is bound to the illumination layer. For example, in some variations, the sample includes one or more polynucleotides which are bound to the illumination layer. In one variation, the sample includes one or more polynucleotides which are bound to the illumination layer, one or more polypeptides which are not bound to the illumination layer, and an aqueous solution. In one variation, the sample includes one or more grana stacks isolated from chloroplasts, deposited on the illumination layer.

In certain embodiments, proximity to the sample will result an increase in photon emission from the illumination layer, compared to the illumination layer further from the sample. In certain embodiments, the presence of the sample will result an increase in photon emission from the illumination layer, compared to the illumination layer in the absence of the sample. For example, in some variations, at least a portion of the sample undergoes resonant optical near-field interactions with at least a portion of the illumination layer, and the emission rate and/or amplitude of at least a portion of the illumination layer are increased, compared to the illumination layer further from the sample. Without wishing to be bound by any theory, in some embodiments the increase in photon emission is a result of surface plasmon resonance between the illumination layer and the sample. In some embodiments, the increase in photon emission is a result of electro-magnetic field enhancement between the sample and the illumination layer.

For example, in certain embodiments the imaging chip includes an illumination layer and a sample layer, wherein the sample layer is configured to hold the sample. In other embodiments, the imaging chip includes an illumination layer, a sample layer, one or more buffer layers, and a frame layer, wherein the sample layer is configured to hold the sample. In other embodiments, the imaging chip includes an illumination layer, a sample layer, a buffer layer, and one or more additional layers. In some embodiments, the imaging chip includes one or more samples. In other embodiments, the imaging chip and one or more samples are provided separately, and the one or more samples are combined with the imaging chip prior to imaging. In still other embodiments, the imaging chip does not comprise a sample layer.

In some embodiments of the methods described herein, the sample is positioned within the optical near-field of the illumination layer. One of skill in the art would appreciate that the optical near-field of an object is the electromagnetic field that oscillates at optical frequencies less than one wavelength from the source. In some embodiments, the sample is positioned within 10 nm of the illumination layer. In certain embodiments, an electron beam is applied to the illumination layer, the illumination layer is excited, there are resonant optical near-field interactions between the illumination layer and the sample, and the illumination layer emits photons. In some variations, the resonant optical near-field interactions decrease photon emission, compared to an illumination layer without the same interactions with the sample. In other embodiments, the resonant optical near-field interactions increase photon emission, compared to an illumination layer without the same interactions. These differences in photon emission from the illumination layer provide contrast in the nanoscale image. In certain embodiments, the choice of sample will affect whether photon emission from the illumination layer will be increased or decreased through resonant optical near-field interactions.

In certain embodiments, the photon emission from the illumination layer as a result of sample proximity increases by a factor of between 1.0 and 3.0, between 1.2 and 2.4, or between 1.4 and 2.2, compared to photon emission from the illumination layer further from the sample. In some variations, the photon emission from the illumination layer as a result of sample proximity increases by a factor of 1.2, a factor of 1.4, a factor of 1.6, a factor of 1.8, a factor of 2.0, a factor of 2.2, a factor of 2.4, a factor of 2.6, or a factor of 2.8, compared to photon emission from the illumination layer further from the sample.

In certain embodiments, the photon emission from the illumination layer in the presence of the sample increases by a factor of between 1.0 and 3.0, between 1.2 and 2.4, or between 1.4 and 2.2, compared to photon emission from the illumination layer in the absence of the sample. In some variations, the photon emission from the illumination layer in the presence of the sample increases by a factor of 1.2, a factor of 1.4, a factor of 1.6, a factor of 1.8, a factor of 2.0, a factor of 2.2, a factor of 2.4, a factor of 2.6, or a factor of 2.8, compared to photon emission from the illumination layer in the absence of the sample.

In certain embodiments, the increase in photon emission from the illumination layer as result of sample proximity depends on distance between the sample and the illumination layer, illumination layer thickness, the presence of any other layers, the thickness of any other layers, and/or electron beam accelerating voltage.

In certain embodiments, proximity to the sample will result in a decrease in photon emission from the illumination layer, compared to the illumination layer further from the sample. In certain embodiments, the presence of the sample will result a decrease in photon emission from the illumination layer, compared to the illumination layer in the absence of the sample. For example, in some variations, at least a portion of the sample undergoes resonant optical near-field interactions with at least a portion of the illumination layer, and the emission rate and/or amplitude of at least a portion of the illumination layer are decreased, compared to the illumination layer without the sample. Without wishing to be bound by any theory, this decrease in emission rate and/or amplitude may be a result of near-field, non-radiative transfer of energy from at least a portion of the illumination layer to at least a portion of the sample. For example, in one variation, the sample is a mixture of organic polymers, and there is a decrease in photon emission from at least a portion of the illumination layer in close proximity to the sample, compared to the illumination layer further from the sample. In some embodiments, the sample has an optical transition energy resonant with the optical emission spectrum of the illumination layer.

Without wishing to be bound by any theory, this transfer of energy may be Förster resonance energy transfer (FRET). The transfer of energy may depend on the distance between the illumination layer and the sample. In some variations at least a portion of the illumination layer emission spectrum overlaps with at least a portion of the sample absorption spectrum, and the transfer of energy may depend on the magnitude of spectral overlap. In certain variations, the decrease in photon emission from the illumination layer may correspond to an increase in photon emission from the sample.

The sample used in the methods described herein may be obtained from any commercially available source, obtained from any naturally available source, isolated from any recombinant organisms, synthetically produced according to any known methods, and/or be produced in situ by combining the suitable components prior to or during imaging. For example, a polynucleotide-polypeptide complex may be produced in situ by adding a polypeptide to a polynucleotide bound to the illumination layer during imaging.

It should be understood that any descriptions of the sample for use in the methods described herein may be combined with any descriptions of the illumination layer, buffer layer, frame layer, sample layer, and/or additional layer the same as if each and every combination were individually listed.

It should be understood that while the imaging system is described with the sample positioned below the illumination layer and the electron beam source positioned above the illumination layer, the imaging system may be oriented in any other equivalent configuration. For example, in one embodiment, the imaging system includes a sample positioned above the illumination layer and an electron beam source positioned below the illumination layer, and at least a portion of the emitted photons below the illumination layer are collected to produce the nanoscale image.

Methods of Nanoscale Imaging

The cathodoluminescence-activated imaging methods may be used with the optical imaging system described herein to obtain a nanoscale image of a sample without directly contacting the sample with an electron beam.

Referring again to FIG. 4, depicted is a flowchart for process 400 to image a sample using an illumination layer and an electron beam source, without contacting the sample with the electron beam produced from the electron beam source. As depicted, process 400 includes a sample positioned below an illumination layer and electron beam source positioned above the illumination layer. In certain variations, the illumination layer and the sample are in an imaging chip.

In process 400, an electron beam is produced from the electron beam source positioned above the illumination layer in step 402. The electron beam contacts at least a portion of the illumination layer in step 404 without penetrating to the sample located below the illumination layer. At least a portion of the illumination layer contacted by the electron beam is excited by the electron beam in step 406, without the sample being excited. In step 408, at least a portion of the excited illumination layer emits photons, and a portion of the emitted photons above the illumination layer are collected in step 410. In step 412, the photons which were collected in step 410 are correlated with the location of electron beam contact with the illumination layer to produce the image in step 414. To produce an image in one dimension (e.g. a linear image) or two dimensions (e.g., a square image), the position of the electron beam is changed in step 416, and steps 404 through 410 are repeated with a different part of the illumination layer.

As described above, in certain embodiments, prior to photon emission the excited illumination layer undergoes resonant energy transfer with the sample, which changes the rate of photon emission from the illumination layer resulting in the image contrast. The type of sample being imaged will determine whether photon emission from the illumination layer is increased or decreased. In certain embodiments, resonant energy transfer between the illumination layer and the sample also results in at least a portion of the sample emitting photons, without the sample being contacted by the electron beam. In some embodiments, the methods described herein further include detecting at least a portion of the photons emitted by the sample, correlating the photons emitted from the sample with the location of electron beam contact with the illumination layer, and producing a nanoscale image of the sample.

Nanoscale Image

The cathodoluminescence-activated imaging methods described herein may be used to produce a nanoscale image using an acquisition rate similar to other rapid imaging techniques (e.g. dark-field scattering microscopy, total internal reflection fluorescence microscopy), with high spatial resolution, and may be used to resolve features of samples that otherwise cannot be imaged using other electron beam methods because of the sample damage incurred. In addition, the methods described herein may be used to obtain multiple images of a sample without electron beam damage to the sample, which can be used for observation of sample dynamics. Thus, in one aspect, provided are nanoscale images produced using any of the methods described herein.

In certain embodiments, the image frame acquisition time is 25.6 seconds. In some embodiments, the image acquisition rate is at least a video frame rate. In some embodiments, the image frame rate is between 20 and 40 frames per second, between 25 and 35 frames per second, or is 30 frames per second. In some embodiments, the time between successive frames is less than 40 seconds, less than 35 seconds, less than 30 seconds, less than 25 seconds, less than 20 seconds, less than 15 seconds, less than 10 seconds, less than 5 seconds, less than 1 second, less than 0.5 seconds, or less than 0.1 seconds. In some embodiments, the time between successive frames is between 1 and 40 seconds, between 1 and 20 seconds, between 1 and 5 seconds, between 25 and 40 seconds, or between 29 and 32 seconds. In other embodiments, the pixel dwell time is between 1 µs and 100 µs, between 1 µs and 50 µs, between 1 µs and 25 µs, or between 1 µs and 10 µs. In certain embodiments, the pixel dwell time is 100 µs or less, or 20 µs or less. In some embodiments, the pixels are between 5 nm and 100 nm. In certain embodiments, the pixels are between 20 nm and 50 nm. In certain embodiments the magnification is between 1,000× to 100,000×. In still other embodiments, the frame is between 128×128 pixels to 1024×1024 pixels. In some embodiments, the frame is 512×512 pixels. It should be understood that in certain embodiments, an image or plurality of images may be acquired using any combination of the embodiments described above. For example, in one embodiment, an image is acquired with a frame of 512×512 pixels, at 10 ms/line. In another embodiment, a plurality of images is acquired with a frame of 512×512 pixels, at 50 ms/line, wherein the pixels are between 20 nm and 50 nm.

It should be understood that in some embodiments, the time that it takes to form an image is different than the process of recording a sequence of images. For example, in some embodiments, a single frame is captured within 30 ms, for example if the sample is moving on a slower time scale, so that there is no blurring of moving features during the capture period. However, separately and additionally, a sequence of such frames may be captured, for example to provide information about the sequence of events. Thus, in some embodiments, a series of images is captured to observe a dynamic process, rather than extracting a snapshot from a single instant during the dynamic process.

In certain embodiments, the spatial resolution of the imaging methods described herein is a nanoscale resolution. In certain embodiments, the spatial resolution of the imaging methods described herein is between 1 nm and 100 nm, between 10 nm and 100 nm, between 10 nm and 90 nm, between 10 nm and 80 nm, between 20 nm and 80 nm, between 30 nm and 80 nm, between 30 nm and 70 nm, between 40 nm and 70 nm, between 40 nm and 60 nm, between 1 nm and 20 nm, between 10 nm and 20 nm, between 10 nm and 30 nm, or between 60 nm and 70 nm. In one variation the spatial resolution is 46 nm. In another variation, the spatial resolution is 68 nm. In yet another variation the spatial resolution is 18 nm. In certain embodiments, the spatial resolution is at least 18 nm, at least 46 nm, or at least 68 nm. In still another variation, the spatial resolution is less than 70 nm, less than 50 nm, less than 20 nm, less than 15 nm, less than 10 nm, or less than 5 nm. The spatial resolution of the imaging methods described herein may be determined by any known method in the art. For example, spatial resolution may be determined by measuring the distance between two points across a feature of the image (e.g. an edge) corresponding to 80% and 20% of the detected maximum intensity of photons emitted from illumination layer.

In certain embodiments, the image produced may resolve features of a sample that otherwise cannot be imaged using other electron beam methods because of the sample damage incurred with those methods. For example, in certain embodiments, a nanoscale image is produced of one or more biological molecules which could not be imaged using other electron beam techniques (e.g., scanning electron microscopy, cathodoluminescence imaging) because of electron beam damage to the sample.

In certain embodiments, multiple images of a sample are produced sequentially. These images may be used, for example, to observe dynamic interactions of the sample. In some embodiments, the sample is dynamic (e.g., undergoes a change in position or conformation over time, or evolves as a function of time).

For example, in one variation, the sample includes a polynucleotide bound to the surface of the illumination layer and a polypeptide bound to the polynucleotide, and multiple images are produced of the sample to observe movement of the polypeptide relative to the polynucleotide. In another variation, the sample includes a phospholipid bilayer and multiple polypeptides, and multiple images are produced of the sample to observe movement of the polypeptides through the phospholipid bilayer. In some variations, multiple images are produced as one or more proteins changes protein conformation. In certain variations, multiple images are produced as one or more molecules is added or removed from the sample. In one variation, the sample includes one or more nanoparticles suspended in ionic liquid, and multiple images are produced of the sample to observe the movement of one or more nanoparticles through the ionic liquid. In one variation, the sample includes one or more nanoparticles deposited on the illumination layer, an ionic liquid is applied to the illumination layer to at least partially enclose the one or more nanoparticles, and multiple images are produced of the sample to observe the movement of one or more nanoparticles through the ionic liquid. In another variation, the sample includes one or more fluorescent polymer particles suspended in oil, and multiple images are produced of the sample to observe the movement of one or more polymer particles through the oil.

Methods of Constructing the Imaging Chip

Any suitable methods known in the art may be used to construct the illumination layer and one or more other layers for use in the imaging methods described herein. Suitable methods may include, for example, photolithography, spin coating, plasma-enhanced chemical vapor deposition (PECVD), pulsed laser deposition, molecular beam epitaxy (MBE), nanosphere lithography, or etching (e.g. wet etching, dry etching, reactive ion etching), or any combinations thereof.

Generally, the imaging chips described herein may be made by forming a free-standing thin scintillating illumination film, either by deposition on a substrate or by thinning of bulk scintillator. The free-standing thin scintillator film is mechanically supported so that the sample can be placed on one side and the electron beam can excite the scintillator film from the other side.

The imaging chips described herein may be made beginning with a substrate material, which may comprise, for example, silicon. In some embodiments, the substrate material is a silicon wafer. The substrate material (e.g., silicon wafer or chip) may then be subjected to a series of deposition and/or etching steps to produce an imaging chip. Any combination of deposition and/or etching steps described herein may be used. In some embodiments, the substrate material is a wafer (e.g., a silicon wafer), and the wafer is diced into smaller chips following the series of deposition and/or etching steps. For example, in one embodiment, the substrate material is a wafer (e.g., a silicon wafer), and the wafer is diced into smaller chips following the formation of an illumination layer. It should be understood that any of the layers described herein, including, for example, illumination layer, frame layer, buffer layer, additional layers, may be independently formed by any of the methods described herein, including, for example, physical deposition, chemical vapor deposition, liquid deposition, wet etching, dry etching, reactive ion etching, or photolithography, or any combinations thereof.

The luminescent dopants of the illumination layer may be provided by ion implantation. In some variations, the thickness of the illumination layer is between 1 nm to 500 nm, between 1 nm to 100 nm, or between 5 nm to 20 nm. In some variations, as described above, a bulk scintillating material is thinned to form the illumination layer. In certain variations, the bulk scintillating material is YAP:Ce. In some variations, etching (e.g., wet etching, dry etching, or reactive ion etching) or photolithography, or a combination thereof, is used to thin the bulk scintillating material to produce the illumination layer.

In other variations, the illumination layer is formed by deposition on a substrate, for example deposition on a silicon wafer or a silicon chip. In certain variations, the illumination layer is deposited on the substrate, and at least a portion of the substrate is removed. Removal of at least a portion of the substrate may include, for example, etching (e.g., wet etching, dry etching, or reactive ion etching) or photolithography, or a combination thereof.

A layer intended for illumination could be deposited first without any lumophores, but where these could be added a posteriori, e.g. as mentioned before: Various forms of ion implantation could in principle be used to provide the luminescent dopants of an illumination layer.

In some embodiments, the methods include physical deposition, chemical vapor deposition, or liquid deposition. In certain embodiments, physical deposition comprises vapor deposition, pulsed laser deposition, or sputtering, or any combinations thereof. In some embodiments, chemical vapor deposition (CVD) comprises plasma enhanced CVD, low pressure CVD, atomic layer deposition, or any combinations thereof. In other embodiments, the liquid deposition comprises sol-gel deposition, solution casting, spin casting, or a combination thereof. It should be understood that any of these methods may be used to deposit or otherwise produce any of the layers described herein, including, for example, the illumination layer, one or more frame layers, one or more buffer layers, or one or more additional layers. The sequence and choice of methods may vary depending, for example, on what layers are being formed and/or on the sample to be imaged.

In some embodiments, the methods include wet etching. In other embodiments, the methods include dry etching. In yet other embodiments, the methods include reactive ion etching. In still other embodiments, the methods include solution casting (e.g., sol-gel spin casting).

Figure 2:
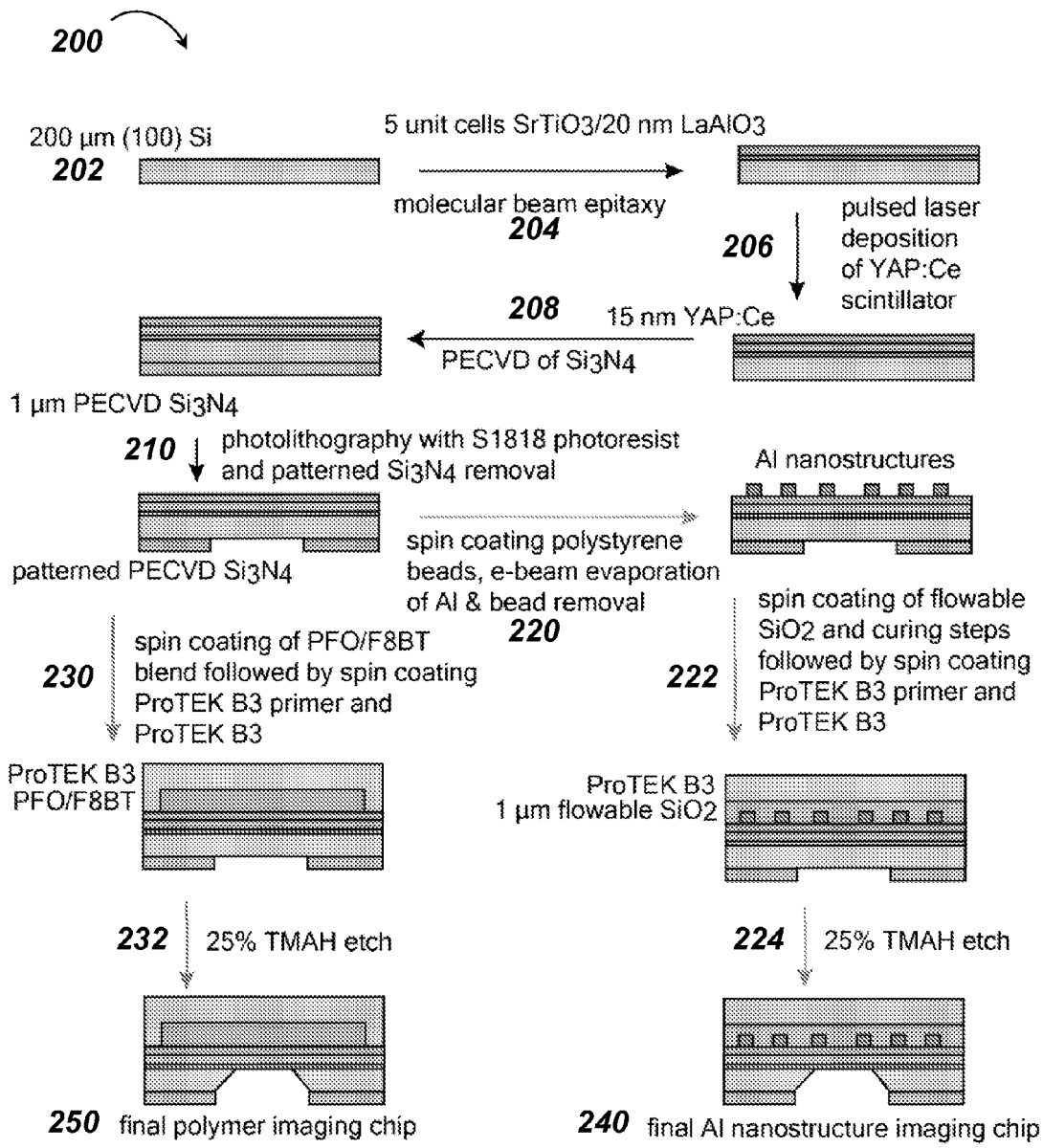
FIG. 2 is a scheme to construct an imaging chip containing an organic polymer sample, and an imaging chip containing an Al nanostructure sample.

Depicted in FIG. 2 is exemplary process 200 for constructing imaging chips containing an illumination layer and a sample. Process 200 may be used to construct imaging chip 240 containing an imaging sample of Al nanostructures, or imaging chip 250 containing an imaging sample of polymer. Process 200 begins with a substrate material, Si wafer 202, which has a top side and a bottom side. In one embodiment, process 200 begins with a 200 μm Si wafer 202, which has a top side and a bottom side. Molecular beam epitaxy 204 deposits two buffer layers onto the top side of wafer 202. The first buffer layer consists of $SrTiO_3$ deposited on the top side of the Si wafer. In one embodiment, 5 unit cells of $SrTiO_3$ is deposited onto the top side of the Si wafer. The second buffer layer consists of $LaAlO_3$ deposited onto the first buffer layer. In one embodiment, 20 nm of $LaAlO_3$ is deposited onto the first buffer layer. Pulsed laser deposition 206 forms an illumination layer of $YAlO_3$ doped with $Ce^{3+}$ (YAP:Ce) on the $LaAlO_3$ buffer layer. In one embodiment, 15 nm $YAlO_3$ doped with $Ce^{3+}$ (YAP:Ce) is deposited on the $LaAlO_3$ buffer layer. Plasma enhanced chemical vapor deposition (PECVD) 208 deposits silicon nitride (e.g., $Si_3N_4$) onto the bottom side of the Si wafer. In one embodiment, 1 μm of silicon nitride (e.g., $Si_3N_4$) is deposited onto the bottom side of the Si wafer. A portion of the silicon nitride (e.g., $Si_3N_4$) is removed with photolithography 210 to expose a portion of the bottom side of the Si wafer. In the embodiment depicted in FIG. 2, the procedures for construction of chips 240 and 250 diverge after step 210.

To fabricate the imaging chip 240, Al nanostructures are constructed on the YAP:Ce illumination layer in 220 by spin coating the illumination layer with polystyrene beads, depositing Al over the spin coated polystyrene beads with electron beam (e-beam) evaporation, and then removing the polystyrene beads. The remaining Al nanostructures are spin coated in step 222 with flowable $SiO_2$, followed by layers of ProTEK® B3 primer and ProTEK® B3. Then, a portion of the exposed bottom side of the Si wafer is etched with tetramethylammonium hydroxide (TMAH) 224 to produce the final imaging chip 240. The final imaging chip 240 contains a Si frame, a buffer layer of $SrTiO_3$, a buffer layer of $LaAlO_3$, a YAP:Ce illumination layer, a sample layer including the Al nanoparticles to be imaged, and other layers of silicon nitride (e.g., $Si_3Ni_4$), ProTEK® B3 primer and ProTEK® B3.

To fabricate the imaging chip 250, the illumination layer is spin coated in step 230 with a combination of polyfluorene (PFO) and poly(9,9-dioctylfluorene-alt-benzothiadiazole) (F8BT), followed by layers of ProTEK® B3 primer and ProTEK® B3. A portion of the exposed bottom side of the Si wafer is etched in step 232 with TMAH to produce the final imaging chip 250. The final imaging chip 250 contains a Si frame, a buffer layer of $SrTiO_3$, a buffer layer of $LaAlO_3$, a YAP:Ce illumination layer, a sample layer including the PFO and F8BT polymer blend to be imaged, and other layers of silicon nitride (e.g., $Si_3Ni_4$), ProTEK® B3 primer and ProTEK® B3.

It should be understood that in other variations, exemplary process 200 may involve one or more added steps. For example, process 200 may involve depositing one or more added buffer layers, depositing one or more added frame layers, and/or removing one or more layers from the imaging chip. It should also be understood that in other variations, one or more steps may be removed from exemplary process 200. For example, in some variations of process 200, only one buffer layer is deposited, no buffer layers are deposited, and/or no frame layer is deposited. In certain variations of process 200, a sample is not included in the sample layer. For example, in some variations of process 200, a sample layer is included which is configured to hold an imaging sample, and the imaging sample is inserted into the sample layer after the conclusion of process 200.

Figure 21:
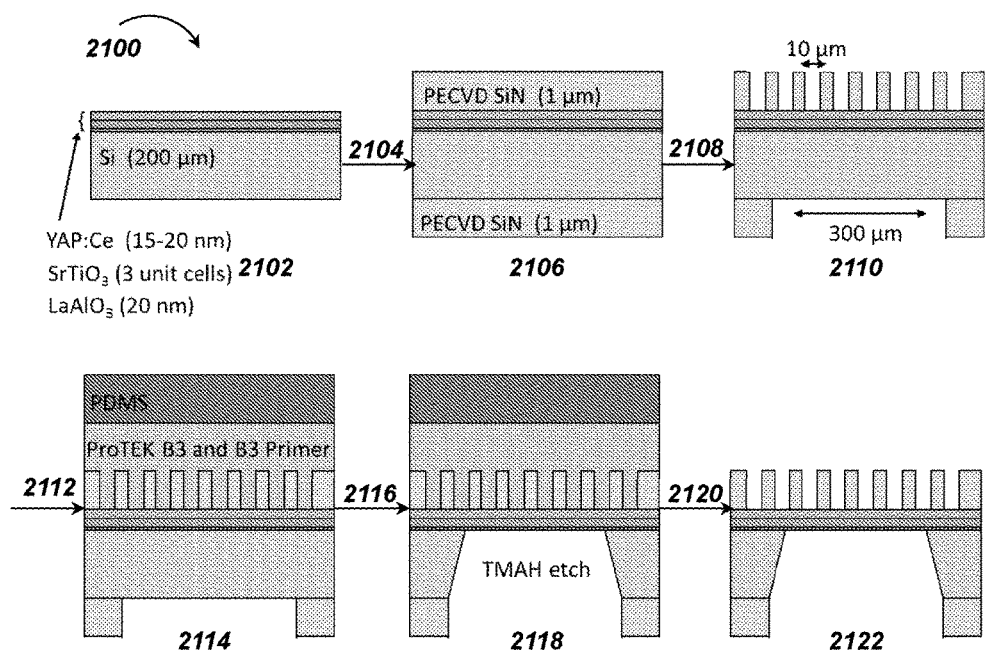
FIG. 21 is a scheme to construct an imaging chip with a YAP:Ce scintillator film illumination layer using a wet-etch method.

Depicted in FIG. 21 is exemplary wet-etch process 2100 for constructing an imaging chip containing an illumination layer and sample wells, in which a sample may be added to the imaging chip after construction. Process 2100 begins with depositing $SrTiO_3$, $LaAlO_3$, and YAP:Ce layers onto a silicon substrate material following process 200 described above through step 206, to produce chip 2102.

Plasma enhanced chemical vapor deposition (PECVD) 2104 deposits silicon nitride onto both sides of chip 2102 to form chip 2106. In one embodiment, 1 μm of silicon nitride (e.g., $Si_3N_4$) is deposited. A portion of the silicon nitride is removed from both sides with photolithography 2108 to expose a portion of the bottom side of the Si wafer and a portion of the top side of the YAP:Ce layer and produce chip 2110. In some embodiments, the photolithography 2108 includes spinning on positive photoresist, masking an area of the film with a chromium mask, exposing with UV light, and developing to remove the photoresist in exposed regions. Following removal of the photoresist, the exposed silicon nitride layer is etched with $O_2/CF_4$ plasma, and the remaining photoresist is removed. The YAP:Ce side of the chip and the Si side of the ship may be patterned with different patterns or the same pattern. For example, in some embodiments, the YAP:Ce side of the chip is patterned with an array of circles. In one embodiment, the YAP:Ce side of the chip is patterned with an array of circles 10 μm in diameter. In another embodiment, the Si side of the chip is patterned with square features. In certain embodiment, the Si side of the chip is patterned with square features 300 μm on a side.

Next, ProTEK® B3 Primer and ProTEK® B3 are deposited on the YAP:Ce side of the chip in step 2112, and a layer of polydimethylsiloxane (PDMS) is deposited on top of the ProTEK® layer to produce chip 2114. A portion of the exposed bottom side of the Si wafer is etched in step 2116 with TMAH to form chip with an imaging window 2118. The ProTEK® B3 and PDMS layers are removed in step 2120 to produce the finished chip 2122. The final imaging chip 2122 contains a Si frame, a buffer layer of $SrTiO_3$, a buffer layer of $LaAlO_3$, a YAP:Ce illumination layer, and a support grid of silicon nitride contacting the YAP:Ce illumination layer.

Depicted in FIG. 22 is exemplary dry-etch process 2200 for constructing an imaging chip containing an illumination layer but without sample wells, in which the sample may be added to the imaging chip after construction. Process 2200 begins with depositing $SrTiO_3$, $LaAlO_3$, and YAP:Ce layers onto a silicon substrate material following process 200 described above through step 206, to produce chip 2202.

In step 2204, alumina ($Al_2O_3$) is deposited on the YAP:Ce layer by atomic layer deposition, and low-stress silicon nitride is deposited by plasma enhanced chemical vapor deposition on top of the alumina. In some variations, the silicon nitride is $Si_3N_4$. Using photolithography 2208, part of the silicon side of the chip is patterned to produce chip 2210 with photoresist contacting portions of the silicon layer, and portions of the silicon layer exposed. In some embodiments, the silicon side of the photoresist is patterned with an array of square crosses. The exposed silicon layer is then dry etched to exhaustion in 2212 with $O_2/SF_6$ plasma in a deep reactive ion etcher using a Bosch process. The remaining photoresist is removed in 2216 and descummed with $H_2/O_2$ plasma in a reactive ion etcher, and the silicon layer is again dry etched so that the depth of the silicon wells is reduced, exposing the $SrTiO_3/LaAlO_3/YAP$:Ce film. An additional alumina layer is deposited on the silicon side of the chip for structural support. In step 2220, the silicon nitride layer is removed using with $O_2/CF_4$ plasma by reactive ion etching to reveal the $SrTiO_3/LaAlO_3/YAP$:Ce film surface that is not contacted by sample wells.

It should be understood that in other variations, exemplary processes 2100 and 2200 may involve one or more added steps. For example, process 2100 or 2200 may involve depositing one or more added buffer layers, depositing one or more sample layers, depositing one or more added frame layers, and/or removing one or more layers from the imaging chip. It should also be understood that in other variations, one or more steps may be removed from exemplary processes 2100 and 2200. For example, in some variations of process 2100 or 2200, only one buffer layer is deposited, no buffer layers are deposited, and/or no frame layer is deposited.

It should be understood that one or more samples may be added to the chips produced by processes 2100 and 2200. In some embodiments, one or more imaging samples are added to a chip produced by process 2100 or 2200, and then a sample layer is added to the chip. For example, in some embodiments, a sample is deposited on the alumina (e.g., $Al_2O_3$) layer above the YAP:Ce layer in the chip produced by process 2200. In certain variations, an imaging sample is deposited and a liquid is applied (for example, an ionic liquid or an oil). In other variations, an imaging sample is deposited in one or more of the sample wells produced by the silicon nitride support grid in the chip produced by process 2100. In certain variations, the imaging sample in one or more wells is continuous (e.g., the imaging sample extends over the top of one or more sections of the support grid). In other variations, the imaging sample in one or more wells is discontinuous (e.g., the imaging sample in a given well does not contact the imaging sample in any other wells).

In some variations of process 2100 or process 2200, the sample is deposited on the imaging chip, and a sample layer is added to the imaging chip to hold the imaging sample. For example, in one embodiment of process 2100, an imaging sample is added to one or more of the sample wells formed by the silicon nitride support layer, and a sample layer is added to the chip contacting at least a portion of the silicon nitride support layer such that one or more sample wells is sealed by the sample layer. In another embodiment of process 2100, an imaging sample is added to one or more of the sample wells formed by the silicon nitride support layer, and a sample layer is added to the chip that does not contact at least a portion of the silicon nitride support layer such that the imaging sample in one or more sample wells is continuous.

In yet other embodiments, which may be combined with any preceding embodiments, the illumination layer is constructed by providing a bulk scintillator and then removing and/or thinning at least a portion of the bulk scintillator to produce an illumination layer. In some variations, the bulk scintillator comprises $YAlO_3$. In some variations, the bulk scintillator further comprises $Ce^{3+}$. Removing and/or thinning at least a portion of the bulk scintillator may be done using any suitable methods as described herein, including, for example, wet etching, dry etching, reactive ion etching, photolithography, or any combinations thereof.

In certain embodiments, which may be combined with any preceding embodiments, dopants may be added to the illumination layer at any point during the construction of an imaging chip. These dopants may be added using any appropriate method known in the art, including, for example, ion implantation. In certain embodiments, the dopants comprise $Ce^{3+}$. For example, in one embodiment, an imaging chip is constructed wherein the illumination layer consists of $YAlO_3$, and then $Ce^{3+}$ dopants are added through ion implantation.

In certain embodiments, depending on the type of imaging sample, different methods of producing an imaging chip may be employed. For example, in some embodiments, the wet-etch process described herein and shown in FIG. 21 may be used with samples that are sensitive to temperature, sensitive to pressure, or unstable over time. In other embodiments, the dry-etch process described herein and shown in FIG. 22 may be used with samples that are sensitive to temperature, sensitive to pressure, or unstable over time. Such samples may include, for example, proteins, DNA, RNA, lipid membranes, plastics, liquids, or organic semiconductors. In some variations, the sample is a soft sample (e.g., organic semiconductors, such as those used in photovoltaics, lighting and/or displays, or flexible circuitry). Using process 2100 or 2200, in which the imaging sample is added to the imaging chip after the TMAH etching of the frame layer, may reduce damage to certain imaging samples than using process 200, in which the sample is added to the imaging chip prior to TMAH etching of the frame layer. In other variations, the method of producing the imaging chip has no effect on the imaging sample.

ENUMERATED EMBODIMENTS

The following enumerated embodiments are representative of some aspects of the invention.

1. A system for imaging a sample, the system comprising:
   an illumination layer;
   a sample,
      wherein the sample is positioned below the illumination layer;
   an electron beam source,
      wherein the electron beam source is positioned above the illumination layer, and is configured to contact multiple locations of the illumination layer with an electron beam, and
      wherein the illumination layer is configured to emit photons when excited by contact with the electron beam;
   an optical detector,
      wherein the optical detector is configured to receive at least a portion of the photons emitted by the illumination layer,
         wherein the at least a portion of the photons emitted by the illumination layer and received by the optical detector are located above the illumination layer; and
   a signal correlation device,
      wherein the signal correlation device is connected to the optical detector and the electron beam source, and is configured to correlate the photons received by the optical detector with the multiple locations of the illumination layer contacted with the electron beam to produce an image of the sample.
2. The system of embodiment 1, wherein the electron beam source is configured to contact multiple locations of the illumination layer with an electron beam without contacting the sample with the electron beam.
3. The system of embodiment 1, wherein the illumination layer has an optical near-field of 10 nm or less, and wherein the sample is located within the optical near-field of the illumination layer.
4. The system of any one of embodiments 1 to 3, further comprising a parabolic mirror to direct the at least a portion of the photons emitted by the illumination layer to be received by the optical detector.
5. The system of any one of embodiments 1 to 4, wherein the illumination layer comprises $YAl_3O$ and $Ce^{3+}$.
6. The system of embodiment 5, wherein the illumination layer is between 5 nm and 20 nm thick.
7. The system of embodiment 5, wherein the illumination layer is between 15 nm and 20 nm thick.
8. The system of any one of embodiments 1 to 7, wherein the sample comprises a biological molecule.
9. A method for imaging a sample, comprising:
   (i) producing an electron beam from an electron beam source;
   (ii) contacting multiple locations of an illumination layer with the electron beam,
      wherein the electron beam source is located above the illumination layer,
      wherein a sample is located below the illumination layer,
      wherein the contacting of the illumination layer with the electron beam excites least a portion of the illumination layer without exciting the sample, and
      wherein at least a portion of the excited illumination layer emits photons;
   (iii) detecting at least a portion of the photons emitted by the excited illumination layer,
      wherein the detected photons are located above the illumination layer; and
   (iv) correlating at least a portion of the detected photons with the multiple locations of the illumination layer contacted with the electron beam to produce an image of the sample.
10. The method of embodiment 9, wherein the illumination layer comprises $YAl_3O$ and $Ce^{3+}$.
11. The method of embodiment 10, wherein the illumination layer is between 5 nm and 20 nm thick.
12. The method of embodiment 10, wherein the illumination layer is between 15 nm and 20 nm thick.
13. The method of any one of embodiments 9 to 12, wherein the sample comprises a biological molecule.
14. The method of any one of embodiments 9 to 13, wherein (ii) through (iv) are repeated to produce one or more additional images of the sample sequentially over a period of time.
15. An imaging chip comprising:
   an illumination layer,
      wherein the illumination layer is configured to be contacted by an electron beam produced from an electron beam source positioned above the illumination layer, become excited by contact with the electron beam, and emit photons when excited;
   a sample layer,
      wherein the sample layer is configured to hold a sample and is positioned below the illumination layer;
   a frame layer,
      wherein the frame layer is configured to provide structural support, is positioned above the illumination layer, and has an imaging window through which an electron beam passes to contact the illumination layer without contacting the frame layer; and a buffer layer, wherein the buffer layer is positioned between the frame layer and the illumination layer.

16. The imaging chip of embodiment 15, wherein the illumination layer comprises $Ce^{3+}$ and $YAlO_3$.

17. The imaging chip of embodiment 16, wherein the illumination layer is between 5 nm and 20 nm thick.

18. The imaging chip of embodiment 16, wherein the illumination layer is between 15 nm and 20 nm thick.

19. The imaging chip of any one of embodiments 15 to 18, wherein the frame layer comprises Si.

20. The imaging chip of any one of embodiments 15 to 19, further comprising an additional buffer layer, wherein the additional buffer layer is positioned between the buffer layer and the frame layer, the buffer layer comprises $LaAlO_3$, and the additional buffer layer comprises $SrTiO_3$.

21. The imaging chip of any one of embodiments 15 to 20, further comprising at least one additional frame layer configured to provide structural support.

22. The imaging chip of embodiment 21, wherein the at least one additional frame layer is a support grid.

23. The imaging chip of embodiment 22, wherein the support grid is positioned between the illumination layer and the sample layer.

24. The imaging chip of embodiment 22 or 23, wherein the support grid comprises silicon nitride.

25. The imaging chip of any one of embodiments 15 to 24, wherein the sample layer further comprises a sample.

26. An image produced by the method of any one of embodiments 8 to 14.

27. The image of embodiment 26, wherein the image has a spatial resolution, and the spatial resolution is at least 46 nm.

28. An imaging chip comprising:

an illumination layer, wherein the illumination layer is configured to be contacted by an electron beam produced from an electron beam source positioned above the illumination layer, become excited by contact with the electron beam, and emit photons when excited;

a frame layer, wherein the frame layer is configured to provide structural support, is positioned above the illumination layer, and has at least one imaging window through which an electron beam passes to contact the illumination layer without contacting the frame layer; and a buffer layer, wherein the buffer layer is positioned between the frame layer and the illumination layer.

29. The imaging chip of embodiment 28, wherein the illumination layer comprises $Ce^{3+}$ and $YAlO_3$.

30. The imaging chip of embodiment 28 or 29, wherein the illumination layer is between 5 nm and 20 nm thick.

31. The imaging chip of embodiment 28 or 29, wherein the illumination layer is between 15 nm and 20 nm thick.

32. The imaging chip of any one of embodiments 28 to 31, wherein the frame layer comprises Si.

33. The imaging chip of any one of embodiments 28 to 32, further comprising an additional buffer layer.

34. The imaging chip of embodiment 33, wherein the additional buffer layer is positioned between the buffer layer and the frame layer.

35. The imaging chip of embodiment 34, wherein the additional buffer layer comprises $SrTiO_3$.

36. The imaging chip of any one of embodiment 28 to 35, wherein the buffer layer comprises $LaAlO_3$.

37. The imaging chip of any one of embodiments 28 to 36, further comprising at least one additional frame layer, wherein the at least one additional frame layer is configured to provide support.

38. The imaging chip of embodiment 37, wherein the at least one additional frame layer is a support grid.

39. The imaging chip of embodiment 38, wherein the support grid is positioned below the illumination layer.

40. The imaging chip of any one of embodiments 28 to 39, further comprising a sample layer, wherein the sample layer is configured to hold a sample.

41. The imaging chip of embodiment 40, wherein the sample layer is positioned below the illumination layer.

42. The imaging chip of embodiment 40 or 41, wherein the sample layer comprises $SiO_2$, a polymer, or any combinations thereof.

43. The imaging chip of any one of embodiments 40 to 42, further comprising at least one additional frame layer, wherein the at least one additional frame layer is positioned between the illumination layer and the sample layer and is configured to provide support.

44. The imaging chip of embodiment 43, wherein the at least one additional frame layer is a support grid.

45. The imaging chip of any one of embodiments 38 to 44, wherein the support grid comprises silicon nitride.

46. The imaging chip of any one of embodiments 37 or 40 to 42, wherein the at least one additional frame layer is positioned below the illumination layer, below the frame layer, or above the illumination layer, or any combinations thereof.

47. The imaging chip of embodiment 46, wherein at least one additional frame layer comprises $Al_2O_3$.

48. The imaging chip of any one of embodiments 28 to 47, further comprising an imaging sample.

49. The imaging chip of embodiment 48, wherein the imaging sample comprises a liquid.

50. The imaging chip of embodiment 49, wherein the imaging sample is at least partially enclosed by liquid.

51. The imaging chip of embodiment 49 or 50, wherein the liquid is an aqueous liquid, an ionic liquid, or an oil, or any combinations thereof.

52. The imaging chip of embodiment 49 or 51, wherein the liquid is an ionic liquid.

53. The imaging chip of embodiment 51 or 52, wherein the ionic liquid is 1-butyl-3-methylimidazolium hexafluorophosphate, 1-butyl-3-methylimidazolium iodide, or 1-ethyl-3-methylimidazolium ethyl sulfate, or any combinations thereof.

54. The imaging chip of any one of embodiments 48 to 53, wherein the sample comprises a biological sample.

55. The imaging chip of embodiment 54, wherein the biological sample comprises a protein, DNA, RNA, a lipid membrane, or any combinations thereof.

56. The imaging chip of any one of embodiments 48 to 55, wherein the sample comprises a polymer.

57. The imaging chip of any one of embodiments 48 to 56, wherein the sample comprises a nanoparticle.

58. The imaging chip of any one of embodiments 48 to 57, wherein the sample comprises a metal.

59. The imaging chip of any one of embodiments 40 to 58, wherein the sample layer is configured to hold more than one sample.

60. The imaging chip of any one of embodiments 28 to 59, wherein the frame layer comprises a plurality of imaging windows.
61. The imaging chip of any one of embodiments 43 to 60, wherein the at least one additional frame layer comprises at least one imaging window.
62. The imaging chip of embodiment 61, wherein the at least one additional frame layer comprises a plurality of imaging windows.
63. The imaging chip of any one of embodiments 51 or 54 to 62, wherein the liquid is an aqueous liquid.
64. The imaging chip of embodiment 63, wherein the aqueous liquid is at least partially enclosed by an encapsulant.
65. The imaging chip of embodiment 64, wherein the encapsulant is an ionic liquid, an oil, graphene, or a polymer, or any combinations thereof.
66. The imaging chip of embodiment 65, wherein the polymer is polydimethylsiloxane.
67. The imaging chip of any one of embodiments 28 to 66, wherein (a) at least a portion of the illumination layer is not contacted by the frame layer, or (b) at least a portion of the illumination layer is not contacted by the frame layer or the buffer layer, or (c) at least a portion of the illumination layer is not contacted by any other layers, or (d) at least a portion of the illumination layer is not contacted by any other layers, and is contacted by a sample.
68. The imaging chip of any one of embodiments 48 to 67, wherein the imaging sample comprises a biological molecule, a liquid, a soft material, or any combinations thereof.
69. The imaging chip of any one of embodiments 48 to 68, wherein the imaging sample is dynamic.
70. A plurality of images produced by the method of any one of embodiments 9 to 14, wherein the rate of acquisition is about 30 frames per second.
71. The plurality of images of embodiment 70, wherein the plurality of images depicts an imaging sample changing over time.
72. A method of producing an imaging chip, comprising:
    (a) providing a substrate material, comprising a top face and a bottom face;
    (b) depositing a first buffer layer on the top face of the substrate material;
    (c) depositing a second buffer layer on top of the first buffer layer;
    (d) depositing an illumination layer on top of the second buffer layer; and
    (e) removing at least a portion of the substrate material to expose at least a portion of the first buffer layer.
73. The method of embodiment 72, wherein the deposition of steps (b) through (d) independently comprises physical deposition, chemical vapor deposition, or liquid deposition, or any combinations thereof.
74. The method of embodiment 72 or 73, wherein the removing of step (e) comprises photolithography, wet etching, or a combination thereof.
75. The method of embodiment 74, wherein the wet etching comprises etching with tetramethylammonium hydroxide (TMAH).
76. The method of any one of embodiments 72 to 75, wherein depositing the illumination layer comprises pulsed laser deposition.
77. The method of any one of embodiments 72 to 76, wherein the illumination layer comprises $YAlO_3$ doped with $Ce^{3+}$.
78. The method of any one of embodiments 72 to 77, wherein the illumination layer comprises 15 nm of $YAlO_3$ doped with $Ce^{3+}$.
79. The method of any one of embodiments 72 to 78, wherein depositing the first buffer layer comprises molecular beam epitaxy.
80. The method of any one of embodiments 72 to 79, wherein depositing the second buffer layer comprises molecular beam epitaxy.
81. The method of any one of embodiments 72 to 80, wherein the first buffer layer comprises $SrTiO_3$.
82. The method of any one of embodiments 72 to 81, wherein the first buffer layer comprises 5 unit cells of $SrTiO_3$.
83. The method of any one of embodiments 72 to 82, wherein the second buffer layer comprises $LaAlO_3$.
84. The method of any one of embodiments 72 to 83, wherein the second buffer layer comprises 20 nm of $LaAlO_3$.
85. The method of any one of embodiments 73 to 84, wherein the physical deposition comprises vapor deposition, pulsed laser deposition, or sputtering, or any combinations thereof.
86. The method of any one of embodiments 73 to 85, wherein the chemical vapor deposition (CVD) comprises plasma enhanced CVD, low pressure CVD, atomic layer deposition, or any combinations thereof.
87. The method of any one of embodiments 73 to 86, wherein the liquid deposition comprises sol-gel deposition, spin casting, or a combination thereof.
88. The method of any one of embodiments 72 to 87, further comprising depositing silicon nitride onto the bottom face of the substrate material after step (d) and prior to step (e).
89. The method of embodiment 88, wherein the silicon nitride is deposited by plasma enhanced chemical vapor deposition (PECVD).
90. The method of embodiment 88 or 89, wherein 1 µm of silicon nitride is deposited onto the bottom face of the substrate material.
91. The method of any one of embodiments 88 to 91, wherein at least a portion of the silicon nitride is removed to expose at least a portion of the bottom face of the substrate material prior to step (e).
92. The method of embodiment 91, wherein the silicon nitride is removed using photolithography.
93. The method of any one of embodiments 72 to 92, further comprising depositing a sample on the illumination layer prior to step (e).
94. The method of embodiment 93, further comprising depositing a sample layer on the sample prior to step (e).
95. The method of embodiment 93 or 94, wherein the sample is deposited by spin coating, electron beam evaporation, or a combination thereof.
96. The method of any one of embodiments 72 to 87, further comprising depositing silicon nitride onto the bottom face of the substrate material and onto the illumination layer after step (d) and prior to step (e).
97. The method of embodiment 96, wherein the silicon nitride is deposited by plasma enhanced chemical vapor deposition (PECVD).
98. The method of embodiment 96 or 97, wherein 1 µm of silicon nitride is deposited onto the bottom face of the substrate material and onto the illumination layer.
99. The method of any one of embodiments 96 to 98, wherein at least a portion of the silicon nitride is removed to expose at least a portion of the bottom face of the substrate material prior to step (e).

100. The method of any one of embodiments 96 to 98, wherein at least a portion of the silicon nitride is removed to expose at least a portion of the illumination layer prior to step (e).
101. The method of embodiment 99 or 100, wherein the silicon nitride is removed using photolithography.
102. The method of any one of embodiments 72 to 87, further comprising depositing alumina onto the illumination layer after step (d) and prior to step (e).
103. The method of embodiment 102, wherein the alumina is deposited by atomic layer deposition.
104. The method of embodiment 102 or 103, further comprising depositing silicon nitride on top of the alumina.
105. The method of embodiment 104, wherein the silicon nitride is deposited by plasma enhanced chemical vapor deposition (PECVD).
106. The method of any one of embodiments 102 to 105, wherein photoresist is deposited on at least a portion of the bottom face of the substrate material prior to step (e).
107. The method of any one of embodiments 102 to 106, wherein step (e) comprises dry etching with $O_2/SF_6$ to remove at least a portion of the substrate material to expose at least a portion of the first buffer layer.
108. The method of any one of embodiments 102 to 107, further comprising depositing alumina onto at least a portion of the bottom face of the substrate material after step (e).
109. The method of embodiment 108, wherein depositing alumina onto at least a portion of the bottom face of the substrate material after step (e) also deposits alumina onto at least a portion of the exposed first buffer layer.
110. The method of any one of embodiments 104 to 109, further comprising removing at least a portion of the silicon nitride to expose at least a portion of the alumina.
111. The method of embodiment 110, wherein the silicon nitride is removed using reactive ion etching.
112. The method of any one of embodiments 72 to 111, wherein the substrate material is silicon.
113. The method of embodiment 112, wherein the substrate material is a silicon wafer.
114. The method of embodiment 112 or 113, wherein the substrate material is 200 μm-thick Si.
115. The method of any one of embodiments 72 to 114, further comprising dividing the imaging chip into a plurality of imaging chips.
116. An image produced by the method of any one of embodiments 9 to 14, wherein:
    (a) the pixel dwell time is between 1 μs and 100 μs;
    (b) the magnification is between 1000× to 100,000×;
    (c) the frame is between 128×128 pixels to 1024×1024 pixels; or
    (d) the pixels are between 5 nm to 100 nm;
    or any combination of (a) to (d).
117. The image of embodiment 116, wherein the pixel dwell time is 20 μs or less.
118. The image of embodiment 116 or 117, wherein the acquisition time is 50 ms/line or less.
119. The image of any one of embodiments 116 to 118, wherein the pixels are between 20 nm to 50 nm.
120. The image of any one of embodiments 116 to 119, wherein the acquisition time is 10 ms/line or less.
121. A plurality of images produced by the method of any one of embodiments 9 to 14, wherein:
    (a) the pixel dwell time is between 1 μs and 100 μs;
    (b) the magnification is between 1000× to 100,000×;
    (c) the frame is between 128×128 pixels to 1024×1024 pixels; or
    (d) the pixels are between 5 nm to 100 nm;
    or any combination of (a) to (d).
122. The plurality of images of embodiment 121, wherein the pixel dwell time is 20 μs or less.
123. The plurality of images of embodiment 121 or 122, wherein the acquisition time is 50 ms/line or less.
124. The plurality of images of any one of embodiments 121 to 123, wherein the pixels are between 20 nm to 50 nm.
125. The plurality of images of any one of embodiments 121 to 124, wherein the acquisition time is 10 ms/line or less.
126. The plurality of images of any one of embodiments 121 to 125, wherein the acquisition rate is 30 frames per second.
127. The plurality of images of any one of embodiments 121 to 126, wherein the plurality of images depicts an imaging sample changing over time.
128. A method of producing an imaging chip, comprising:
    providing a frame layer configured to provide support, wherein the frame layer has a top side and a bottom side; and
    depositing an illumination layer above the top side of the frame layer to produce the imaging chip.
129. The method of embodiment 128, wherein at least a portion of the illumination layer contacts the frame layer.
130. The method of embodiment 128 or 129, wherein at least a portion of the illumination layer is not contacted the frame layer.
131. The method of any one of embodiments 128 to 130, further comprising removing at least a portion of the frame layer so that at least a portion of the illumination layer is not contacted by the frame layer.
132. A method of producing an imaging chip, comprising:
    providing a bulk scintillator; and
    removing a portion of the bulk scintillator to form an illumination layer and a frame layer to produce the imaging chip,
        wherein the frame layer is the portion of the bulk scintillator that is not removed, and
        wherein the illumination layer is supported by the frame layer.
133. The method of any one of embodiments 128 to 132, wherein the illumination layer is between 1 nm to 500 nm thick, or between 5 nm to 20 nm thick.
134. The method of any one of embodiments 128 to 131, wherein the deposition of the illumination layer comprises physical deposition, chemical vapor deposition, or liquid deposition, or any combinations thereof.
135. The method of embodiment 134, wherein the physical deposition comprises vapor deposition, pulsed laser deposition, or sputtering, or any combinations thereof.
136. The method of embodiment 134 or 135, wherein the chemical vapor deposition (CVD) comprises plasma enhanced CVD, low pressure CVD, or atomic layer deposition, or any combinations thereof.
137. The method of any one of embodiments 134 to 136, wherein the liquid deposition comprises solution casting, sol-gel deposition, or spin casting, or a combination thereof.
138. The method of embodiment 131, wherein removing the at least a portion of the frame layer comprises photolithography or wet etching, or a combination thereof.
139. The method of embodiment 132 or 133, wherein the removing of the at least a portion of the bulk scintillator comprises photolithography or wet etching, or a combination thereof.

140. The method of any one of embodiments 132, 133, or 139, wherein the bulk scintillator comprises $YAlO_3$.
141. The method of embodiment 140, wherein the bulk scintillator further comprises $Ce^{3+}$.
142. The method of any one of embodiments 128 to 137, wherein depositing the illumination layer comprises pulsed laser deposition.
143. The method of any one of embodiments 128 to 142, wherein the illumination layer comprises $YAlO_3$ doped with $Ce^{3+}$.
144. The method of any one of embodiments 128 to 142, wherein the illumination layer comprises $YAlO_3$.
145. The method of embodiment 144, further comprising adding dopants to the illumination layer.
146. The method of embodiment 145, wherein the dopants comprise $Ce^{3+}$.
147. The method of embodiment 145 or 146, wherein the dopants are added by ion implantation.
148. The method any one of embodiments 128 to 131, 133 to 137, or 142 to 147, further comprising depositing a buffer layer above the frame layer, wherein the illumination layer is deposited above the buffer layer.
149. The method of embodiment 148, wherein depositing the buffer layer comprises molecular beam epitaxy.
150. The method any one of embodiments 128 to 131, 133 to 137, or 142 to 147, further comprising depositing a first buffer layer above the frame layer and depositing a second buffer layer above the first buffer layer, wherein the illumination layer is deposited above the second buffer layer.
151. The method of embodiment 150, wherein depositing the first buffer layer comprises molecular beam epitaxy.
152. The method of embodiment 150 or 151, wherein depositing the second buffer layer comprises molecular beam epitaxy.
153. The method of any one of embodiments 150 to 152, wherein the first buffer layer comprises $SrTiO_3$.
154. The method of any one of embodiments 150 to 153, wherein the first buffer layer comprises 5 unit cells of $SrTiO_3$.
155. The method of any one of embodiments 150 to 154, wherein the second buffer layer comprises $LaAlO_3$.
156. The method of any one of embodiments 150 to 155, wherein the second buffer layer comprises 20 nm of $LaAlO_3$.
157. The method of any one of embodiments 128 to 156, further comprising depositing a sample on the illumination layer.
158. The method of embodiment 157, further comprising depositing a sample layer on the sample.
159. The method of embodiment 157 or 158, wherein the sample is deposited by spin coating, electron beam evaporation, or a combination thereof.
160. The method of any one of embodiments 128 to 159, further comprising depositing a layer configured to provide support above the illumination layer, wherein at least a portion of the layer configured to provide support contacts the illumination layer.
161. The method of any one of embodiments 128 to 160, further comprising depositing a layer configured to provide support below the illumination layer, wherein at least a portion of the layer configured to provide support contacts the illumination layer.
162. The method of embodiment 160 or 162, wherein the layer configured to provide support comprises silicon nitride or alumina, or a combination thereof.
163. The method of any one of embodiments 128 to 132, 133 to 137, 142 to 162, wherein the frame layer is silicon.
164. The method of embodiment 163, wherein the frame layer is a silicon wafer.
165. The method of embodiment 163 or 164, wherein the frame layer is 200 μm-thick Si.
166. The method of any one of embodiments 128 to 165, further comprising dividing the imaging chip into a plurality of imaging chips.
167. The image of embodiment 26, wherein the image has a spatial resolution, and the spatial resolution is less than 70 nm, less than 50 nm, less than 20 nm, less than 18 nm, less than 10 nm, or less than 5 nm.
168. The system of any one of embodiments 1 to 8, wherein the system is configured to produce a plurality of images of the sample.
169. The system of embodiment 168, wherein the system is configured to produce a plurality of images of the sample over time.
170. The system of any one of embodiments 1 to 8, 168, or 169, wherein the system is configured to image the sample over time, and produce a plurality of images of the sample sequentially over a period of time.
171. The system of any one of embodiments 1 to 7 or 168 to 170, wherein the sample (a) comprises a biological molecule, a liquid, a soft material, or any combinations thereof, or (b) is dynamic, or a combination of (a) and (b).
172. The system of any one of embodiments 1 to 8 or 168 to 171, wherein the sample is dynamic.

EXAMPLES

The following Examples are merely illustrative and are not meant to limit any aspects of the present disclosure in any way.

Cathodoluminescence (CL) emission spectra were measured with a modified Zeiss Gemini SUPRA 55 Scanning Electron Microscope (SEM) fitted with a spectrometer consisting of an Acton 2300i monochromator (150 line/mm, 500-nm blazed grating) and an Andor Newton electron-multiplied CCD. An aluminum parabolic reflector was positioned above the same sample in order to couple a 1.3π solid angle of emission into a photomultiplier tube (Hamamatsu, H7360-01) outside of the vacuum chamber. For Examples 12 through 14, additional photomultiplier tubes were used (Hamamatsu H7421-40 and H7421-50), and an Ocean Optics QE65PRO spectrometer was used. All images for Examples 1 through 9 were acquired with 512×512 pixels and a scanning rate of 50 ms/line. Images for Examples 12 through 14 were acquired using a scanning rate of about 10 ms/line and frame averaging.

Atomic force microscopy (AFM) of Al nanostructures was performed using an MFP-3D-BIO (Asylum Research) using Multi75Al Budget Sensors probes (Ted Pella).

Photoluminescence lifetime measurements were collected with a Horiba Jobin Yvon Fluorolog-3 Spectrofluorometer at a repetition rate of 1 MHz and a typical pulse width of <1.2 ns using an attached 310 nm NanoLED (Horiba Scientific) as the time-correlated single-photon counting (TCSPC) source. Using the Horiba Scientific Decay Analysis Software, DAS6, the lifetime data for YAP:Ce was fit to a single exponential with a characteristic lifetime of 16.1 ns and the lifetime data for YAP:Ce with Al nanostructures was fit to two exponentials with lifetimes of 7.8 and 16.1 ns after taking into account the instrument response function. The same procedure was used to fit the lifetime data of YAP:Ce with PFO, which was fit to a single exponential with a characteristic lifetime of 10.2 ns.

Monte Carlo simulations of electron trajectories were performed using the CASINO v3.2 program. See Demers H, Poirier-Demers N, Couture A R, Joly D, Guilmain M, de Jonge N, Drouin D, Three-dimensional electron microscopy simulation with the CASINO Monte Carlo software, Scanning, (2011), 33: pg 135-146. For each computation, 10,000 electrons were simulated in an environment consisting of 2 nm $SrTiO_3$, 20 nm $LaAlO_3$, 15 nm $YAlO_3$, 50 nm Al and 1.0 μm $SiO_2$. Finite-difference time-domain (FDTD) calculations using Maxwell's equations to calculate the enhancement of dipoles in the vicinity of the Al nanostructure were performed using FDTD Solutions by Lumerical Solutions, Inc. The $Ce^{3+}$ dopants were modeled as a time-windowed dipole source that radiates between 320 and 450 nm using a grid size of 1.0 nm. The calculations were performed in an environment identical to the imaging chip. Al nanostructures were constructed using the height obtained from the AFM image and using lateral dimensions obtained from the SE image.

Example 1

Preparation of an Imaging Chip with a $YAlO_3$:Ce Illumination Layer

This Example demonstrates the preparation of an imaging chip with a $YAlO_3$ illumination layer containing $Ce^{3+}$ (YAP:Ce).

Onto one side of a 3-inch, 200-μm-thick Si wafer (001) (Virginia Semiconductor) was deposited 5 unit cells of (100)-oriented $SrTiO_3$ followed by 20 nm of (001) $LaAlO_3$ via molecular beam epitaxy (MBE). The (001) and (100) indicate the lattice planes denoted by Miller indices. The wafer was then diced into 5×8 mm chips using a Disco DAD3240 Automatic Dicing Saw in Marvell Nanofabrication Laboratory. Pulsed laser deposition (PLD) was used to deposit 15 nm of YAP:Ce onto the $LaAlO_3$ layer. The PLD source material was a disk of single-crystal YAP:Ce (0.55 wt % Ce, SEMicro), and the laser pulses were generated by a Lambda Physik KrF excimer source operating at a wavelength of 248 nm and pulse-rate of 6 Hz, with a fluence of approximately 0.7 $J/cm^2$. The substrates were held at 750° C. in a 1.0 mTorr $O_2$ atmosphere during the growth and subsequently cooled at a rate of 10° C./min.

After PLD, onto the opposite side of the Si wafer was deposited 1 μm of silicon nitride (e.g. $Si_3N_4$) via plasma enhanced chemical vapor deposition (PECVD) using an Oxford Plasmalab 80plus PECVD System in Marvell Nanofabrication Laboratory. A layer of S1818 photoresist (Shipley) was spun onto the PECVD silicon nitride (e.g., $Si_3N_4$) side of the chip using a WS-650Mz-23NPP spin coater (Laurell Technologies Corporation) for 1 min at 2500 rpm with a 2000 rpm/s acceleration. After coating, the chip was baked on a hotplate at 95° C. for 2 min. The chip was then placed under a plastic mask (ARTNET 4 Pro) containing a 4×4 grid of transparent ~300 μm×300 μm squares on a black background and exposed for 10 sec in a 365 nm UV lamp at 15 $MW/cm^3$. Afterward, the chip was placed in Microposit MF-319 developer (Shipley) for approximately 1 min and rinsed with deionized water. The chip was then placed in a reactive ion etcher (RIE) (PETS, Inc.) for approximately 5 min (400 W, 16 sccm $CF_4$, 4 sccm $O_2$, ~600 mTorr) to remove the silicon nitride (e.g., $Si_3N_4$). The S1818 photoresist was then removed by soaking in Remover PG (MicroChem), acetone, and isopropyl alcohol for 5 min each and drying with $N_2$. The chip was again placed in the RIE for 1 min (200 W, 10 sccm $O_2$, ~150 mTorr) for a final cleaning.

Example 2

Modification of an Imaging Chip to Include a Sample Layer Containing an Aluminum Nanostructure Sample and Imaging Windows This Example demonstrates the addition of an Al nanostructure sample and a sample layer to an imaging chip with a YAP:Ce scintillator film, and the construction of imaging windows in the imaging chip.

The imaging chip was prepared according to the procedure set forth in Example 1.

To add the sample to the chip, nanosphere lithography was used to fabricate Al nanostructures on the YAP:Ce film surface of the imaging chip. A 26 mg/ml solution consisting of polystyrene (PS) beads (Bangs Laboratories Inc.) with a 1.0 μm diameter in 8:1 water/methanol with 1% Triton X-100 (Aldrich) were spun onto the YAP:Ce side of the chip. The sequence for the spin coating was 800 rpm/2000 rpm/s for 10 s, 500 rpm/2000 rpm/s for 2 min, 2400 rpm/2000 rpm/s for 20 s, and 6000 rpm/5000 rpm/s for 6 s. The PS beads formed an incomplete monolayer.

Using a Semicore SC600 electron beam evaporator, 50 nm of Al was deposited on the YAP:Ce film surface and the PS beads were removed in toluene.

The Al nanostructures were then encapsulated in $SiO_2$ by spinning on FOX-16 flowable $SiO_2$ (Dow Corning) at 4000 rpm/2000 rpm/s for 1 min. To cure the $SiO_2$, the chip was baked at 150° C., 200° C., and 350° C. on hotplates for 1 min each. The chip was then placed in a quartz tube oven at 400° C. for 1 hr while flowing Ar. An adhesion layer of ProTEK® B3 primer (Brewer Science) was spun onto the $SiO_2$ side of the chip at 2500 rpm/2000 rpm/s and baked on a hotplate for 3 min at 220° C. ProTEK® B3 was then applied at 6000 rpm/5000 rpm/s for 6 s, 2500 rpm/2000 rpm/s for 1 min, and 6000 rpm/5000 rpm/s. It was then baked on a hotplate at 110° C. for 5 min and 220° C. for 20 min. After baking, the chip was placed in 25% tetramethylammonium hydroxide (TMAH) (Spectrum Chemicals) at 50° C. overnight and then cleaned with spectroscopic grade methanol (Aldrich) and deionized water. The chip was then attached to an Al SEM stub (Ted Pella) with carbon tape for imaging.

Figure 6A:
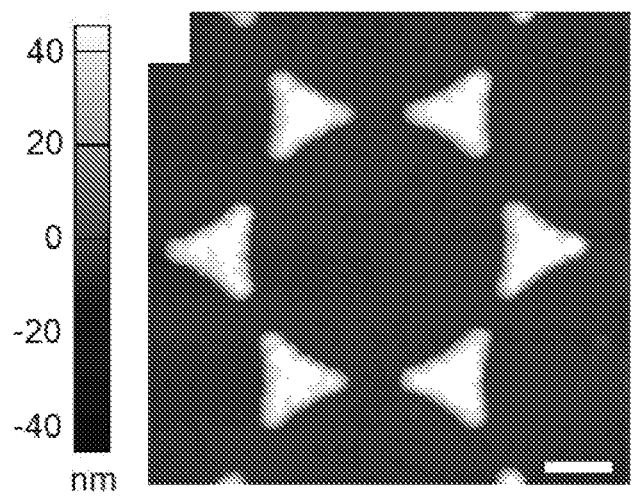
FIG. 6A is an atomic force microscopy (AFM) image of Al nanostructures deposited on a YAP:Ce scintillator film. The scale bar represents 250 nm.
Figure 6B:
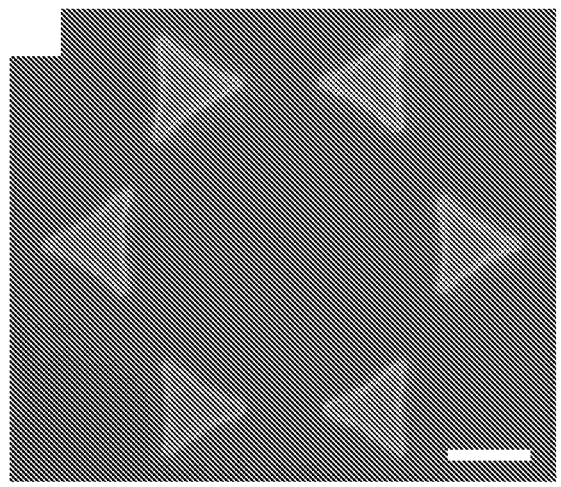
FIG. 6B is a scanning electron microscopy (SEM) image of Al nanostructures deposited on a YAP:Ce scintillator film. The scale bar represents 250 nm.
Figure 6C:
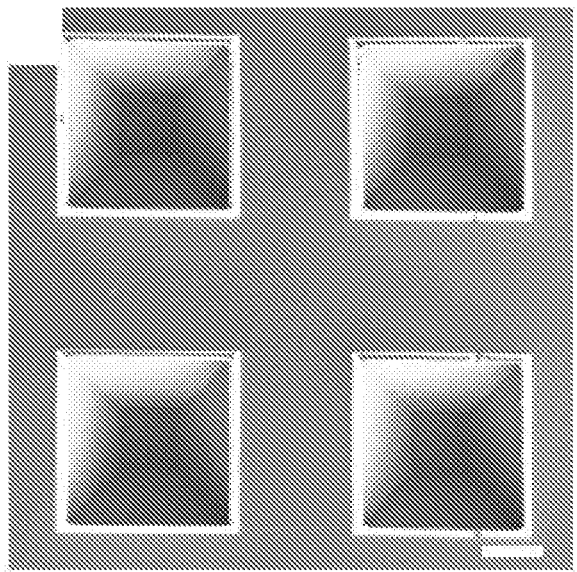
FIG. 6C depicts an SEM image of four imaging windows formed on an imaging chip containing a YAP:Ce scintillator film and Al nanostructure sample. The scale bar indicates 100 μm.

A schematic of the chip preparation and Al nanostructure loading is shown in FIG. 2. A schematic of the completed imaging chip containing Al nanostructures is shown in FIG. 1. FIG. 6A is the AFM image of the Al nanostructures deposited on the YAP:Ce film prior to encapsulation with $SiO_2$. The scale bar in the lower right represents 250 nm. FIG. 6B is SEM image of the Al nanostructures deposited on the YAP:Ce film prior to encapsulation with $SiO_2$. The scale bar in the lower right represents 250 nm. The images indicate the Al nanostructures are 50 nm thick with a point-to-edge distance of approximately 270 nm. FIG. 6C depicts an SEM image of four of the imaging windows formed on the chip during the wet etch in TMAH. The scale bar indicates 100 μm.

Example 3

Modification of an Imaging Chip to Include a Sample Layer Containing an Organic Polymer Sample and Imaging Windows This Example demonstrates the addition of a sample of a conjugated polymer blend of polyfluorene (PFO) and poly (9,9-dioctylfluorene-alt-benzothiadiazole) (F8BT) and a sample layer to an imaging chip with a YAP:Ce scintillator film, and the construction of imaging windows in the imaging chip.

The imaging chip was prepared according to the procedure set forth in Example 1.

A solution comprising 0.5% PFO (H. W. Sands) and 0.5% F8BT (Solaris Inc.) by weight in o-xylene (Aldrich) was prepared in a glovebox and then filtered through a 0.45 µm syringe filter. The solution was then spun onto the YAP:Ce layer of the imaging chip at 1000 rpm/2000 rpm/s for 1 minute. Next, polymer was removed with a razor blade from the outer 1 mm of the chip to allow for direct contact between the YAP:Ce chip and the ProTEK® B3 layer and to prevent the PFO/F8BT film from coming into contact with the TMAH in a later step.

An adhesion layer of ProTEK® B3 primer (Brewer Science) was then spun onto the polymer sample side of the chip at 2500 rpm/2000 rpm/s and baked on a hotplate for 3 min at 220° C. ProTEK® B3 was then applied at 6000 rpm/5000 rpm/s for 6 s, 2500 rpm/2000 rpm/s for 1 min, and 6000 rpm/5000 rpm/s. It was then baked on a hotplate at 110° C. for 5 min and 220° C. for 20 min. After baking, the chip was placed in 25% TMAH (Spectrum Chemicals) at 50° C. overnight and then cleaned with spectroscopic grade methanol (Aldrich) and deionized water. The chip was then attached to an Al SEM stub (Ted Pella) with carbon tape for imaging. A schematic the chip preparation and polymer sample loading is shown in FIG. 2.

Example 4

Spatial Uniformity of a YAP:Ce Scintillator Film

This Example demonstrates quantification of the spatial uniformity of a YAP:Ce scintillator film. The YAP:Ce thin film was produced according to the procedure described in Example 1.

Figure 5A:
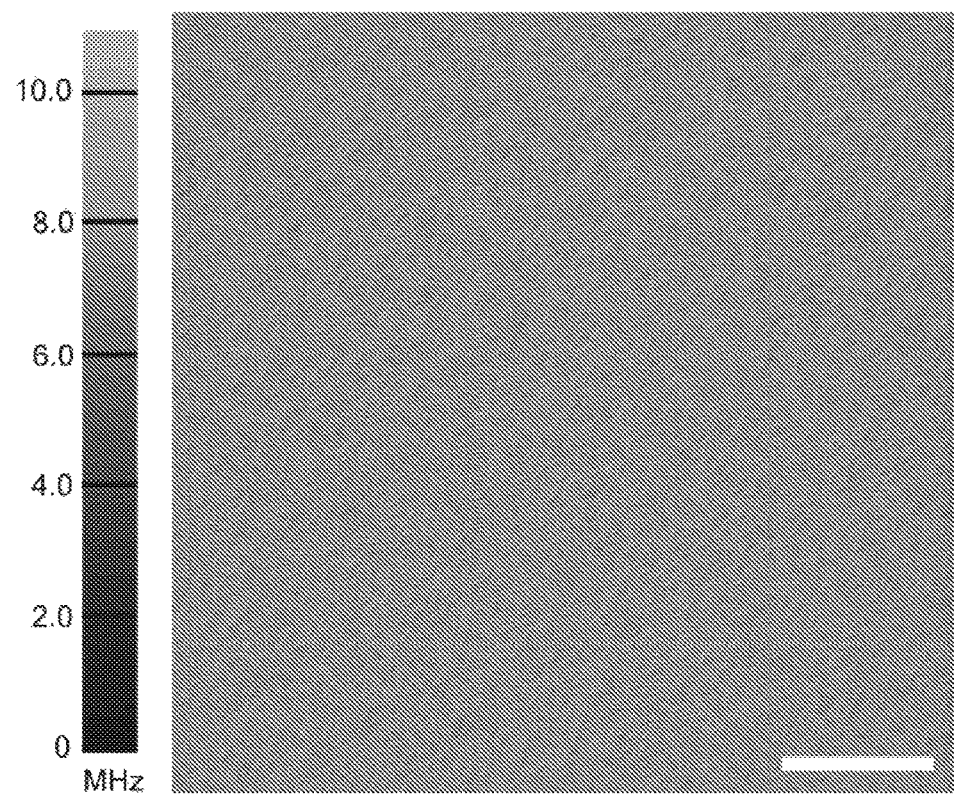
FIG. 5A is a cathodoluminescence (CL) image of a YAP:Ce scintillator film without a sample. The scale bar represents 1 μm.
Figure 5B:
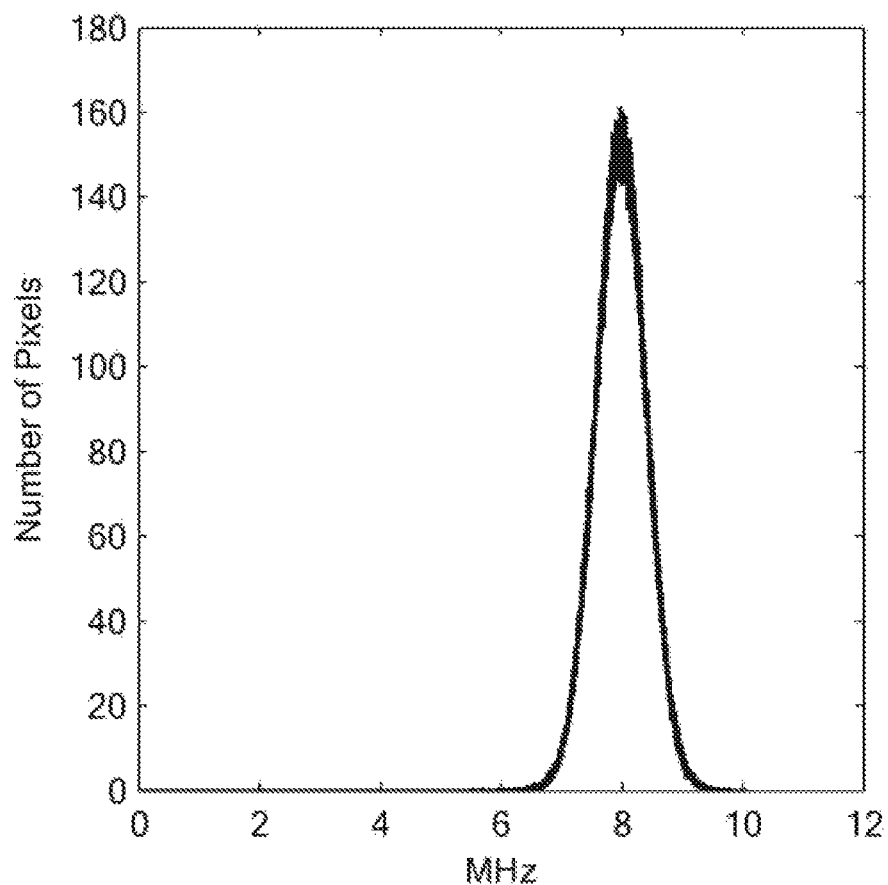
FIG. 5B is a histogram of emission intensity per pixel from a CL image of a YAP:Ce scintillator film without a sample.

The luminescence uniformity of the YAP:Ce scintillator film was measured by generating a CL image of the film, as shown in FIG. 5A (scale bar represents 1 µm). A histogram of the counts per pixel shown in FIG. 5B shows that the distribution of intensities is quite narrow. The average counts per pixel is 7.99 MHz and the standard deviation is 0.67 MHz, which represents a uniformity of CL to within 8%. The distribution of intensities is smaller than the variations observed in the presence of an imaging sample.

To determine the relative contributions to the 8% variation from shot noise at a given pixel and to true film variations as a function of position, these two sources of variation are added in quadrature, and other potential noise sources are neglected. Similar to other images obtained in the Examples described herein, the 512×512 image FIG. 5A was obtained at a rate of 50 ms per line, such that the average number of counts per pixel at the 7.99 MHz count rate is 780 counts. As a result of isolating the corresponding 4% variation in counts per pixel due to shot noise, a 7% variation in brightness as a function of pixel location is obtained.

Example 5

Nanoscale Imaging of Al Nanostructures

This Example demonstrates nanoscale imaging of an Al nanostructure sample using an imaging chip with a YAP:Ce scintillator film, and characterization of the YAP:Ce film in the presence and absence of the Al nanostructures.

The imaging chip was prepared according to the procedure described in Example 1, and modified to contain Al nanostructures, a sample layer, and imaging windows according to the procedure described in Example 2. A "control imaging chip" without a YAlO$_3$:Ce scintillator film was also constructed following the same procedure, but omitting the PLD of YAlO$_3$:Ce.

Figure 7:
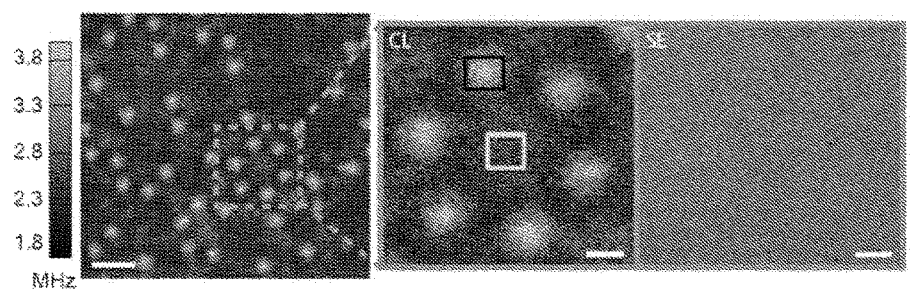
FIG. 7 is a nanoscale image of a sample of Al nanostructures obtained using an imaging chip with a YAP:Ce scintillator film. The scale bar represents 1.0 μm. The inset shows a CL image of a cluster of six Al nanostructures (left) and a secondary electron (SE) image of the same cluster (right). The scale bars represent 250 nm.

The sample of Al nanostructures was imaged using an optical imaging system with a scanning electron microscope, spectrometer, and parabolic mirror as described above, with a 1.8 kV, 1.2 nA electron beam. The orientation of the electron beam relative to the imaging chip, Al nanostructure sample, and parabolic mirror is depicted in FIG. 1. The nanoscale image obtained is depicted in FIG. 7 (left; scale bar represents 1 µm), with an inset showing a cluster of six Al nanostructures (middle; scale bar represents 250 nm). The upper black box indicates an area with an Al nanostructure, and the lower white box indicates an area without an Al nanostructure. Also shown is the secondary electron image (right; scale bar represents 250 nm) corresponding to the inset image.

Figure 8:
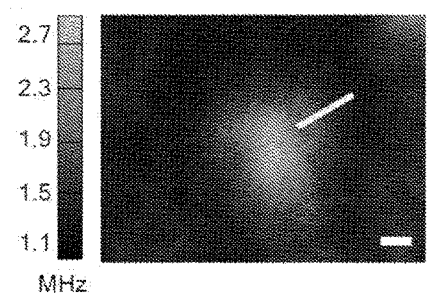
FIG. 8 is a nanoscale image of a single Al nanostructure obtained using an imaging chip with a YAP:Ce scintillator film. The scale bar represents 50 nm.
Figure 10:
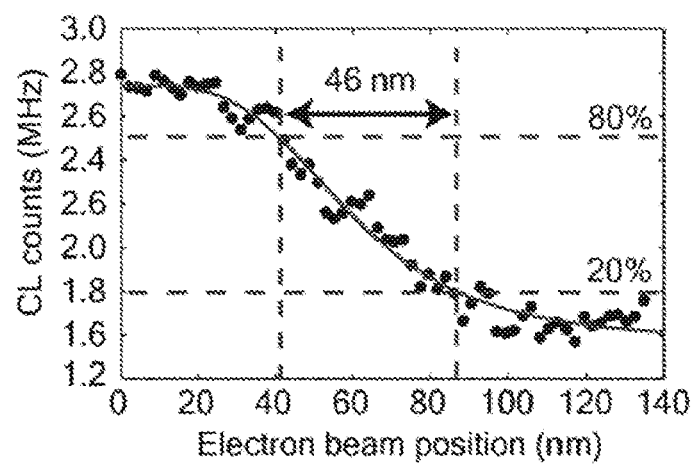
FIG. 10 is a graph of the CL emission detected across a line-cut of a nanoscale image of an Al nanostructure sample.

The spatial resolution of the YAP:Ce film at an electron beam acceleration of 1.8 kV was quantified by measuring the YAP:Ce luminescence of a line-cut spanning the edge of one Al nanostructure. FIG. 8 depicts the image of the single Al nanostructure obtained, and the diagonal white line indicates the line-cut path along which luminescence was measured. FIG. 10 depicts a graph showing the luminescence measured compared to the position of the electron beam, with levels at 80% and 20% of the maximum measured luminescence indicated. The difference between the electron beam positions at 80% and 20% of the maximum luminescence provides a spatial resolution of 46 nm.

Figure 9:
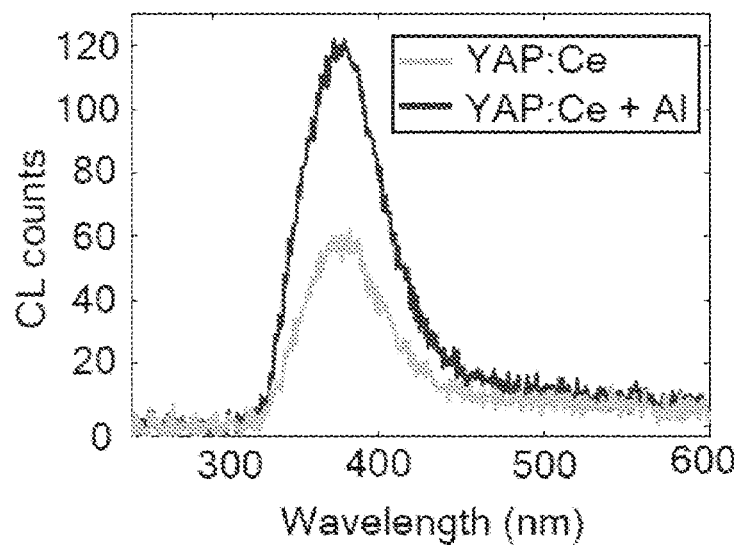
FIG. 9 is a graph comparing the CL spectrum of a YAP:Ce scintillator film in the presence and absence of an Al nanostructure sample.

FIG. 9 depicts the CL spectrum obtained when the electron beam was positioned above the illumination layer and an Al nanostructure, compared to the spectrum obtained when the electron beam was positioned above the illumination layer without an Al nanostructure. As shown by the graph, the luminescence from YAP:Ce approximately doubles when in the presence of an Al nanostructure, compared to the YAP:Ce film alone.

Figure 11:
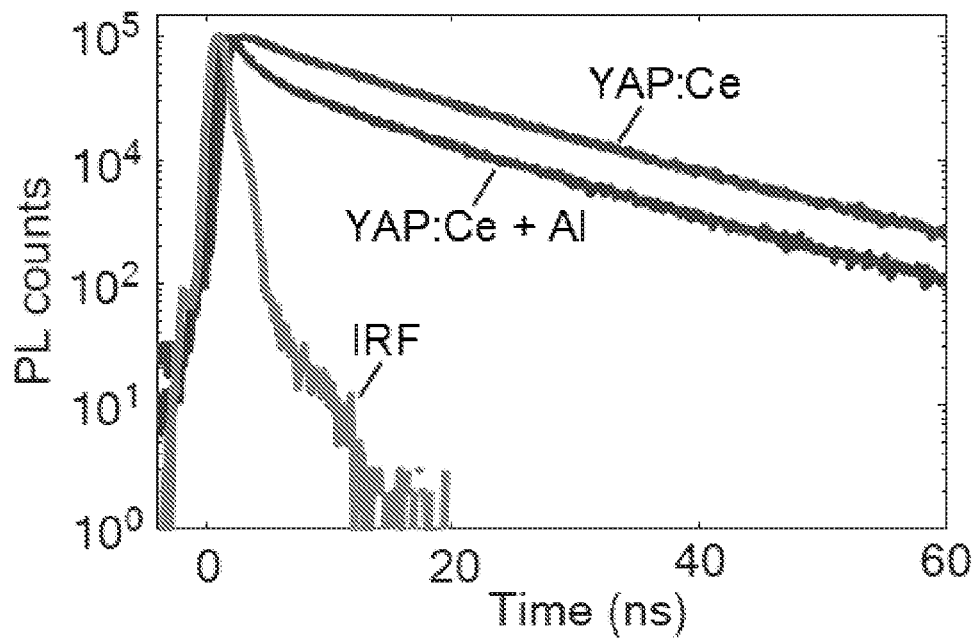
FIG. 11 is a graph of fluorescence lifetime of a YAP:Ce scintillator film in the presence and absence of an Al nanostructure sample.

The effect that Al nanostructures had on photoluminescence (PL) decay of the YAP:Ce illumination layer was also studied. As shown in FIG. 11, the presence of Al contributes about 7.8 ns to the PL decay of YAP:Ce, compared to a decay in the absence of Al of about 16.1 ns. This decrease in the PL lifetime of Ce$^{3+}$ in the presence of Al is consistent with the approximately doubled luminescence observed in the presence of Al, as discussed above.

The control imaging chip prepared without YAP:Ce was also studied. No detectable luminescence form the Al nanostructures was observed up to an accelerating voltage of 5.0 kV, indicating the observed luminescence enhancement discussed above was not caused by direct electron excitation of the Al.

The differences in YAP:Ce luminescence observed in the presence and absence of the Al nanostructures indicates near-field interactions between the Ce$^{3+}$ dopants in the illumination layer and the Al nanostructures.

The per-pixel count rates of the Al images are very similar to those of the CL image of the YAP:Ce film in FIG. 5A, as described in Example 4.

Example 6

Comparison Experimental and Computational Model Data for Imaging of Al Nanostructures This Example demonstrates the development of a computational model for imaging of Al nanostructures, comparison of that model with experimental imaging data, and how the electron beam can be configured to penetrate the illumination layer to cause photon emission without exciting the sample below.

The experimental imaging data was obtained as described in Example 5.

Figure 12A:
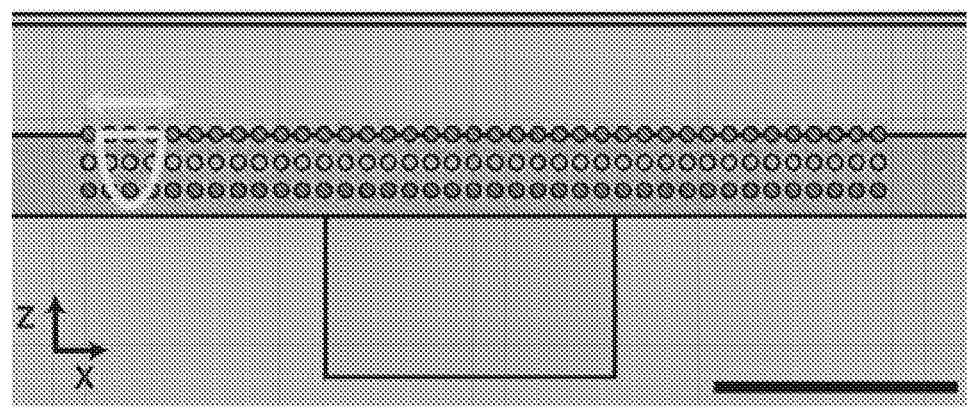
FIG. 12A is a side-view schematic of the geometry used in finite-different time-domain (FDTD) simulations of imaging Al nanostructures with a YAP:Ce scintillator film.
Figure 12B:
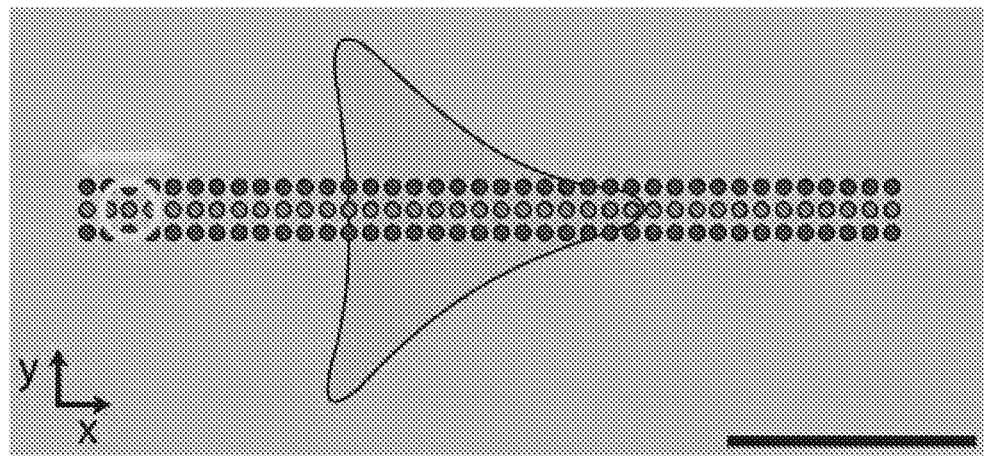
FIG. 12B is a top-view schematic of the geometry used in FDTD simulations of imaging Al nanostructures with a YAP:Ce scintillator film.

Finite-difference time-domain (FDTD) calculations: The FDTD simulations were performed using FDTD Solutions from Lumerical Solutions Inc. The $Ce^{3+}$ luminescent center was modeled as a time-windowed, oscillating point source for the electric field with a line shape (320-450 nm) that mimicked the experimental CL spectrum of $Ce^{3+}$ in $YAlO_3$:Ce, obtained as described above. The spatial extent of the simulated Al nanostructure was determined experimentally from the SE image as shown in FIG. 6B for the x and y dimensions and the AFM image as shown in FIG. 6A for the z dimension. FIGS. 12A and 12B depict schematics of the simulation geometry (scale bars represent 250 nm). Each circle in both images represents an FDTD simulation of an individual dipole. FIG. 12A depicts a side view, with each horizontal row of circles, beginning at the top, representing dipole positions 15 nm, 10 nm, and 5 nm from the interface between YAP:Ce and Al or $SiO_2$. The box in the lower middle of the figure represents the Al nanostructure. FIG. 12B depicts a top view, with the outside horizontal rows of circles representing dipoles positioned along the center of the nanostructure, and the center row of circles representing dipoles displaced 20 nm from the other rows. The shape in the middle of the figure represents the Al nanostructure.

The calculations used a Al nanostructure placed in an environment of $SiO_2$ (n=1.4) with layers of 15 nm YAP:Ce (n=1.93), 20 nm $LaAlO_3$ (n=2.0), 2 nm $SrTiO3$ (n=2.41), and vacuum (n=1.0) above the nanostructure.

To start, simulations of a single $Ce^{3+}$ dipole at many different locations within the YAP:Ce film above the nanostructure were performed. The modeled $Ce^{3+}$ dipole in the YAP:Ce layer was positioned above the surface of the nanostructure, and simulations were performed for a dipole placed in 20 nm increments along a 750-nm-long line running through the edge, center and tip of the nanostructure at distances of 5 nm, 10 nm, and 15 nm from the YAP:Ce/Al interface in the z direction. At each point, the enhancement of the total radiated power was calculated for three orthogonal dipole orientations oriented along the x, y, and z axes.

Figure 12C:
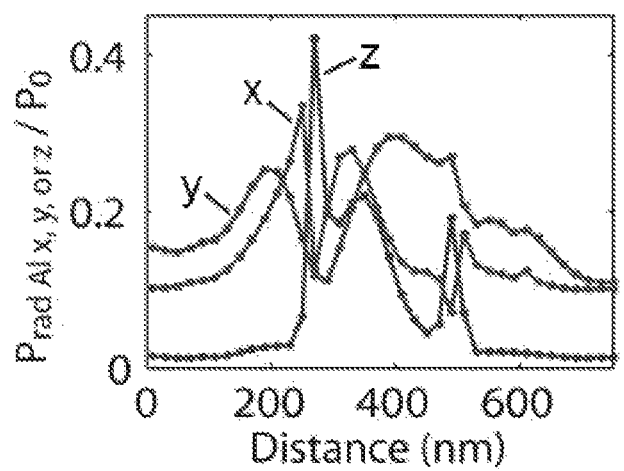
FIG. 12C is a plot of enhancement factor versus distance in FDTD simulations of imaging Al nanostructures with a YAP:Ce scintillator film, for dipoles oriented in the x, y, and z directions.

Enhancement of the radiated power was calculated by integrating the radiative power flux passing through a surface above the nanostructure and adjacent layers. The radiated power was only considered in this direction because this was also the direction in which light was collected with the parabolic mirror in the experimental setup. The value calculated was a ratio between the power radiated in the presence of the Al nanoparticle and device layers ($P_{rad\ Al}$) and the power radiated if the dipole were in vacuum ($P_0$). FIG. 12C depicts a plot of $P_{rad\ Al}/P_0$ versus distance for dipoles oriented in x, y, and z, demonstrating the dipole orientation dependence of the enhancement.

Figure 12D:
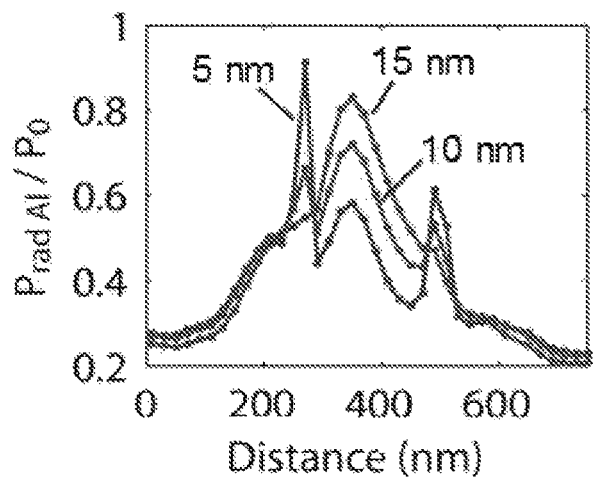
FIG. 12D is a plot of enhancement factor versus distance in FDTD simulations of imaging Al nanostructures with a YAP:Ce scintillator film, for averaged dipole orientations located 5 nm, 10 nm, or 15 nm from the YAP:Ce—Al interface.

A more direct comparison between theoretical system and data from the experimental set-up is a ratio of Prad Al and the power radiated by a $Ce^{3+}$ dipole in an imaging chip that lacks the Al nanostructures ($P_{rad\ no\ Al}$). This value was calculated using the same method as above, but with the Al nanostructure removed. Therefore, if the dipoles in YAP:Ce are oriented isotropically due to multiple allowed 4f to 5d transitions, the enhancement factor at each point is equal to:

$$\eta_{rad} = \frac{P_{radAlx} + P_{radAly} + P_{radAlz}}{P_{radnoAlx} + P_{radnoAly} + P_{radnoAlz}} = \frac{P_{radAl}}{P_{radnoAl}},$$

where $P_{rad\ Al\ x}$, $P_{rad\ Al\ y}$, and $P_{rad\ Al\ z}$ are the radiative power flux calculated in the configuration of (with Al present) for dipoles oriented in x, y, and z, respectively, and $P_{rad\ no\ Al\ x}$, $P_{rad\ no\ Al\ y}$, and $P_{rad\ no\ Al\ z}$ are the radiative power flux calculated with no Al present for dipoles oriented in x, y, and z, respectively. Radiative enhancement occurs when $P_{rad\ Al}/P_{rad\ no\ Al} > 1$. FIG. 12D depicts the respective plots for $P_{rad\ Al}/P_{rad\ no\ Al}$ for dipoles at 15 nm, 10 nm, and 5 nm from the surface.

Figure 12E:
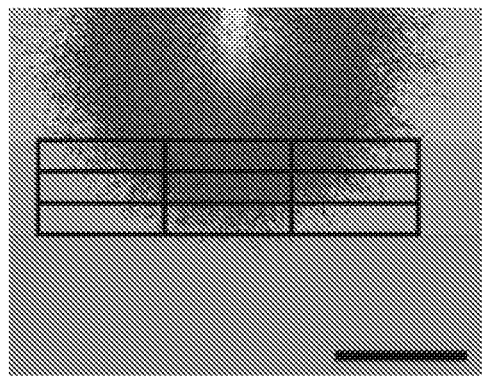
FIG. 12E is a side-view schematic showing electron trajectories of a Monte Carlo simulation of imaging Al nanostructures with a YAP:Ce scintillator film. The scale bar represents 250 nm.
Figure 12F:
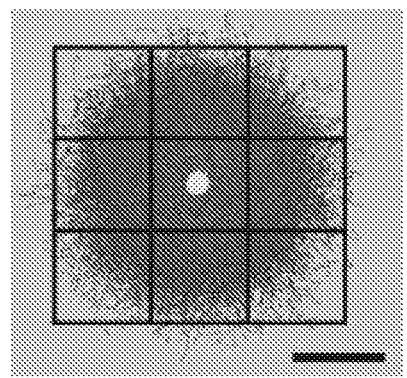
FIG. 12F is a top-view schematic showing electron trajectories of a Monte Carlo simulation of imaging Al nanostructures with a YAP:Ce scintillator film. The scale bar represents 250 nm.

During imaging, the electrons scatter within YAP:Ce and excite a distribution of $Ce^{3+}$ in x, y and z. To account for the extent of electron scatter within the material, simulations were performed at points along an additional cross-section displaced by 20 nm from the original cross-section at distances of 5 nm, 10 nm, and 15 nm from the metal surface in the z direction. Electron trajectories were calculated using Monte Carlo CASINO simulations to determine how many dipole locations to include to mimic a pixel's signal in the experimental CL-activated image. The light half-ovoid and circle shapes in FIGS. 12A and 12B, respectively, indicate the bounds of the extent of electron scattering within the material for a particular electron beam position. The corresponding volume includes the locations of 27 different single dipole calculations. The enhancement factor of each of these dipoles was computed the result weighted based on the number of electron collisions in the vicinity of each dipole. FIGS. 12E and 12F show the electron trajectories of a Monte Carlo simulation, with the black grid demonstrating how the electron collisions are partitioned into a 3×3×3 array totaling 27 different areas. The enhancement factor for the CL-activated volume centered on a given circle along the center row of circles in FIG. 12B, $\eta_{CL}$, is written as a sum of the contributing enhancement factors from surrounding modeled dipoles, each multiplied by the relative number of electron collisions in the vicinity of each of these dipoles:

$$\eta_{CL} = \frac{\sum_{i=1}^{27} \frac{N_i P_{radAl,i}}{N_{total} P_{0,i}}}{\sum_{i=1}^{27} \frac{N_i P_{radnoAl,i}}{N_{total} P_{0,i}}},$$

where $\eta_{CL}$ is the computed theoretical enhancement factor for the $Ce^{3+}$ dipoles activated by the electron beam, i is an index associated with the dipole corresponding to one of the 27 partitions of the electron scattering volume, $N_i$ is the number of electron collisions in the volume represented by the ith dipole, $N_{total}$ is the total number of electron collisions in all 27 regions combined, $P_{rad\ Al,\ i}$ is the radiative power calculated when Al is present for dipole i, $P_{0,i}$ is the radiative power calculated in vacuum for dipole i, and $P_{rad\ no\ Al,\ i}$ is the radiative power calculated when no Al is present for dipole i.

Figure 13:
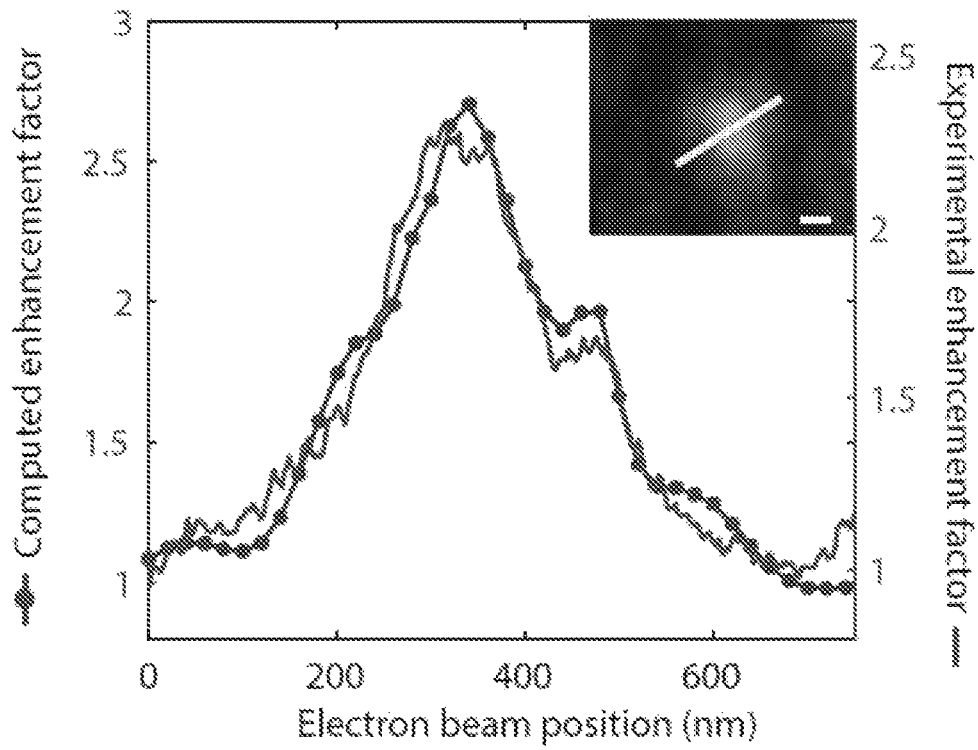
FIG. 13 is a graph of the enhancement factor of a line-cut across an Al nanostructure imaged with a YAP:Ce scintillator film, from experimental and FDTD simulations. The inset is the experimental image with the line-cut across the Al nanostructure indicated by the diagonal line. The scale bar represents 50 nm.

This procedure was repeated for each electron beam location along the x-axis in our simulation geometry in order to generate a model for the experimental line-cut across a single Al nanostructure that was performed as described in Example 5. A comparison of a line-cut from experimental data and the computed enhancement factor ($\eta_{CL}$) versus electron beam position is shown in FIG. 13. The dots of the simulated trace indicate the location of the center of the modeled dipole distribution for each position of the line-cut. The resulting line-cut from the FDTD simulations matches both the width and the shape of the experimental line-cut.

Without wishing to be bound by any theory, the experimental and theoretical observations suggest that the total $Ce^{3+}$ luminescence collected over the course of a pixel dwell-time is altered in proximity to the Al nanostructures because a $Ce^{3+}$ transition dipole induces a macroscopic polarization in the nearby metal nanostructure. The in-phase contribution to this polarization increases the $Ce^{3+}$ emission rate and amplitude, which corresponds to the shortened lifetime component, increased CL emission, and the FDTD simulations.

Example 7

Effect of Electron Beam Accelerating Voltage on Image Contrast and Resolution

This Example demonstrates how changing the electron beam accelerating voltage affects the contrast and resolution of nanoscale images of an Al nanostructure sample.

The imaging chip was prepared as described in Examples 1 and 2.

Images of the Al nanostructures were acquired at accelerating voltages ranging from 1.0 to 3.0 kV. FIGS. 15A-D are representative images taken at 1.0 kV, 1.6 kV, 2.2 kV and 2.8 kV, respectively. The scale bars in the lower right corner represent 1.0 µm.

Figure 16:
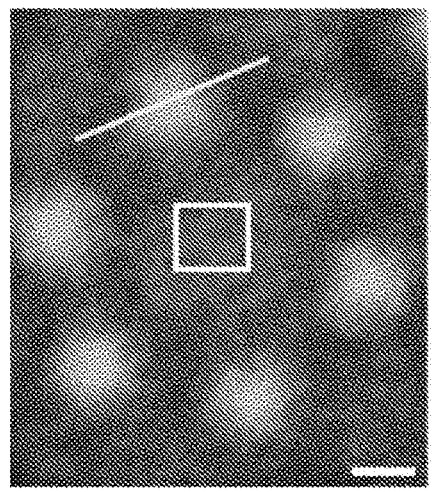
FIG. 16 is a nanoscale image of Al nanostructures acquired using a YAP:Ce scintillator film, with a line-cut across a single Al nanostructure indicated by the diagonal line, and a white box indicating the absence of Al.

To calculate the enhancement factor, a line-cut of the same nanostructure was taken at each accelerating voltage (1.0, 1.2, 1.4, 1.6, 1.8, 2.0, 2.2, 2.4, 2.6, 2.8, 3.0, and 3.2 kV). FIG. 16 depicts a representative image with the line-cut indicated by the diagonal white line spanning one of the Al nanostructures. The white outlined box indicates an area with no Al present. Each line-cut was from edge to edge of the nanostructure going through the center, so that the line-cut is symmetric and encompasses the peak enhancement of the nanostructure. Each line-cut was corrected for the non-linearity of the photomultiplier tube (PMT) response and fit to the Gaussian function:

$$f(x) = a\exp\left(-\frac{(x-b)^2}{2c^2}\right) + d.$$

Figure 17:
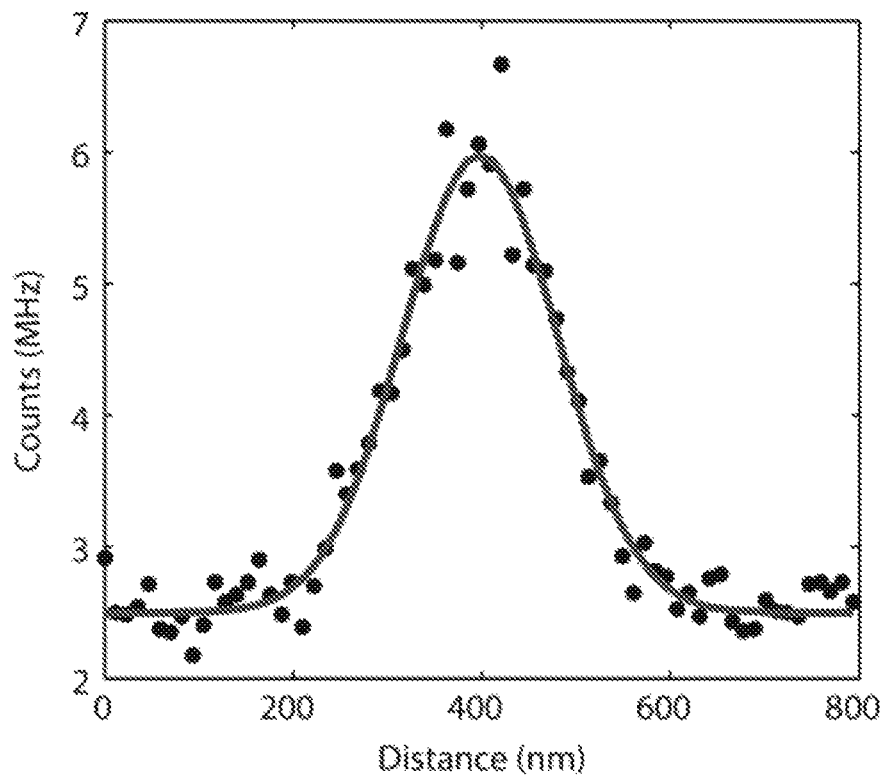
FIG. 17 is a graph of a Gaussian fit for the experimentally acquired enhancement factor of a line-cut across a single Al nanostructure imaged with a YAP:Ce scintillator film.

A representative Gaussian fit is depicted in FIG. 17, for a 2.2 kV image. The peak value of the Gaussian function was found in units of MHz and then divided by the average counts per pixel in a neighboring region with no Al present, which was also corrected for the non-linearity of the PMT. Error bars were calculated based on the standard deviation of the background CL with no Al present and the 95% confidence bounds of the Gaussian fit coefficient a.

Figure 14A:
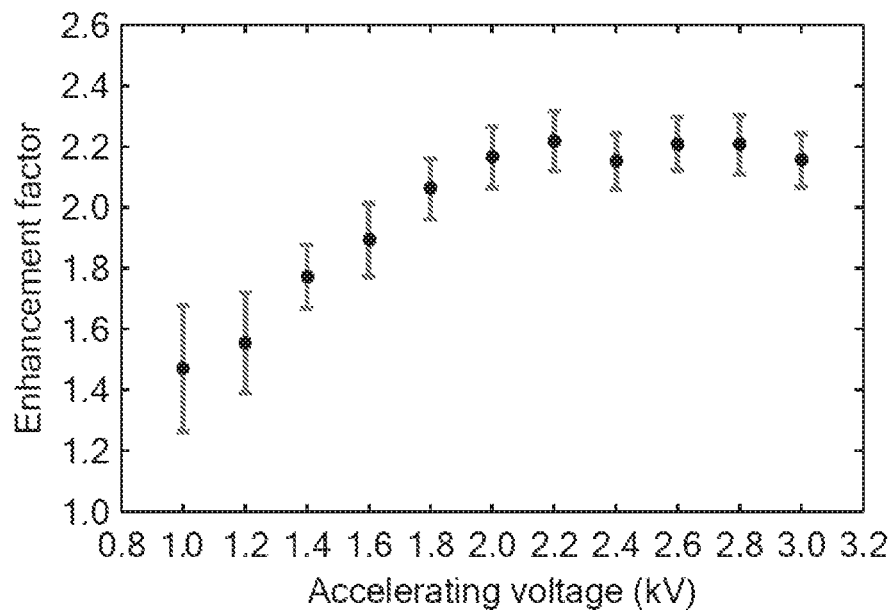
FIG. 14A is a plot of the CL enhancement factor at different electron beam accelerating voltages, obtained experimentally, for a YAP:Ce scintillator film in the presence of Al nanostructures.
Figure 14B:
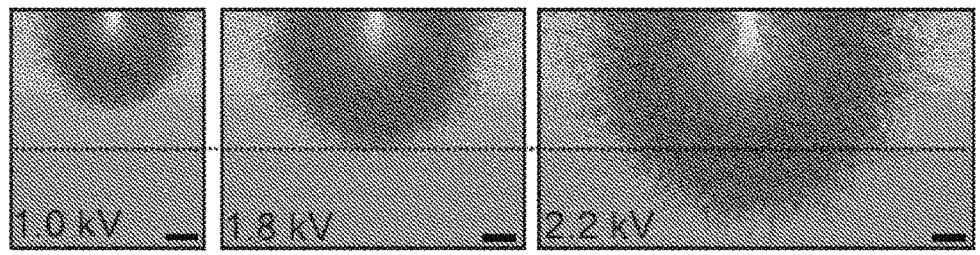
FIG. 14B is a side-view schematic of Monte Carlo simulations of imaging Al nanostructures with a YAP:Ce scintillator film at different electron beam accelerating voltages. The scale bars represent 10 nm.
Figure 15A:
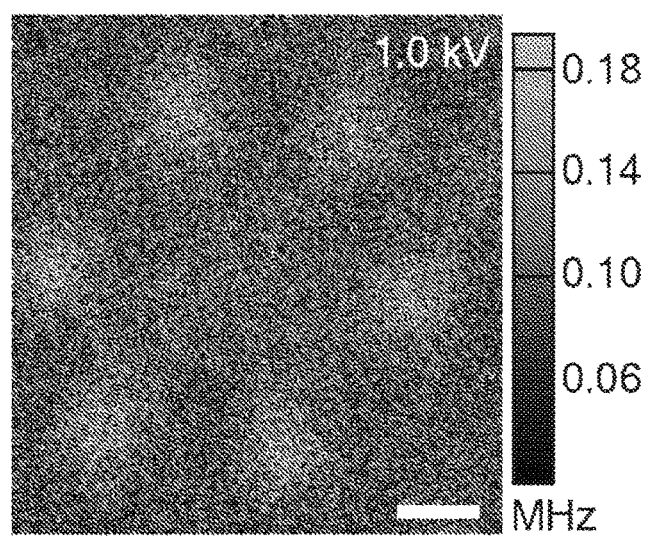
FIG. 15A is a nanoscale image of Al nanostructures acquired with an electron beam accelerating voltage of 1.0 kV, using a YAP:Ce scintillator film. The scale bar represents 1.0 µm.
Figure 15B:
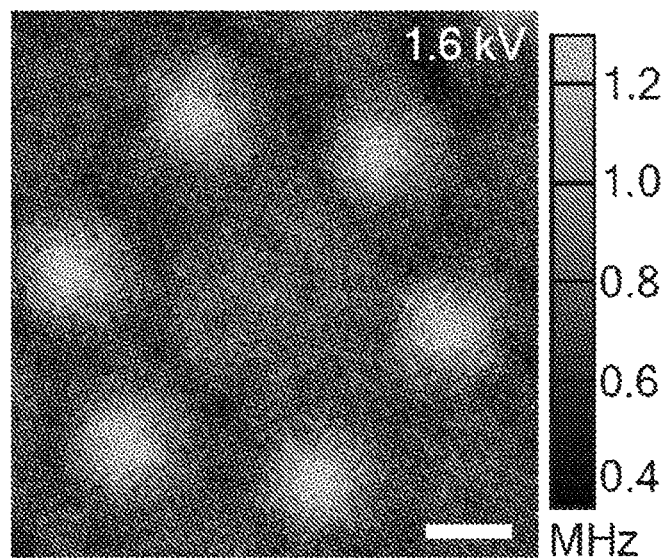
FIG. 15B is a nanoscale image of Al nanostructures acquired with an electron beam accelerating voltage of 1.6 kV, using a YAP:Ce scintillator film. The scale bar represents 1.0 µm.
Figure 15C:
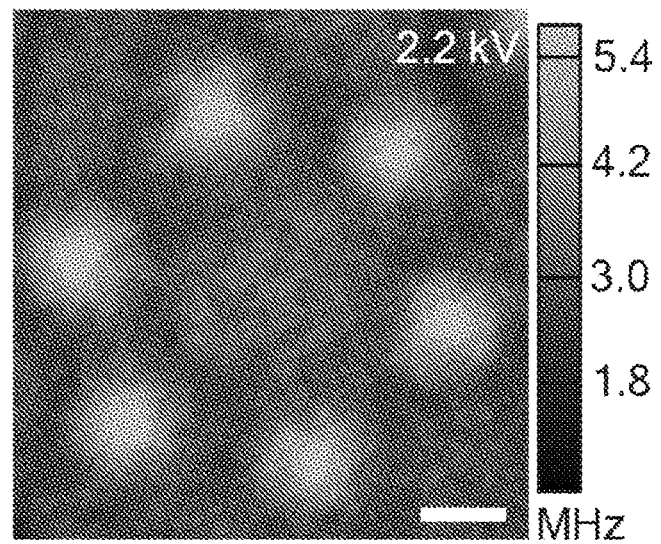
FIG. 15C is a nanoscale image of Al nanostructures acquired with an electron beam accelerating voltage of 2.2 kV, using a YAP:Ce scintillator film. The scale bar represents 1.0 µm.
Figure 15D:
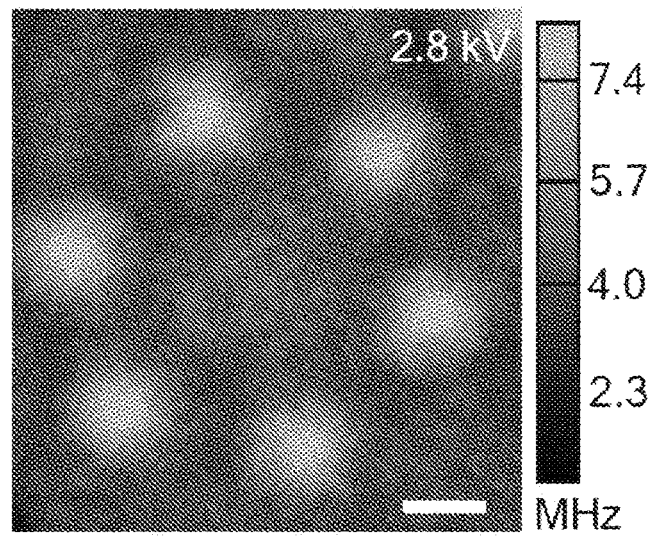
FIG. 15D is a nanoscale image of Al nanostructures acquired with an electron beam accelerating voltage of 2.8 kV, using a YAP:Ce scintillator film. The scale bar represents 1.0 µm.

Depicted in FIG. 14A is a plot of the CL enhancement factor versus accelerating voltage, obtained experimentally. The enhancement factor increases linearly as the accelerating voltage increases from 1.0 to 2.0 kV, and it plateaus beyond 2.0 kV. FIG. 14B is a schematic showing Monte Carlo simulations of electron trajectories at 1.0 kV, 1.8 kV, and 2.2 kV. The dotted line represents the interface between the sample (bottom) and the scintillator layer (top). The scale bars represent 10 nm.

The Monte Carlo simulations performed as described above suggest the linear increase is due to a progressive increase in the number of activated $Ce^{3+}$ emitters located close enough to the Al nanostructure to be enhanced. Between 1.0 and 2.0 kV, the signal-to-noise ratio and enhancement factor both improve. Beyond 2.0 kV, the enhancement factor plateaus because there are no additional $Ce^{3+}$ to be excited. The Monte Carlo simulation previously showed that at 1.8 kV, very few electrons reach the Al even though they approach the interface. This suggests an accelerative voltage of 1.8 kV at this film thickness maximizes near-field interaction with the sample while maintaining a low probability of electrons interacting directly with the sample.

Example 8

Nanoscale Imaging of an Organic Polymer Blend

This Example demonstrates nanoscale imaging of a sample of polyfluorene (PFO) blended with poly(9,9-dioctylfluorene-alt-benzothiadiazole) (F8BT), using an imaging chip with a YAP:Ce scintillator.

The imaging chip containing the polymer blend sample was prepared as described in Example 1 and Example 3.

Figure 18A:
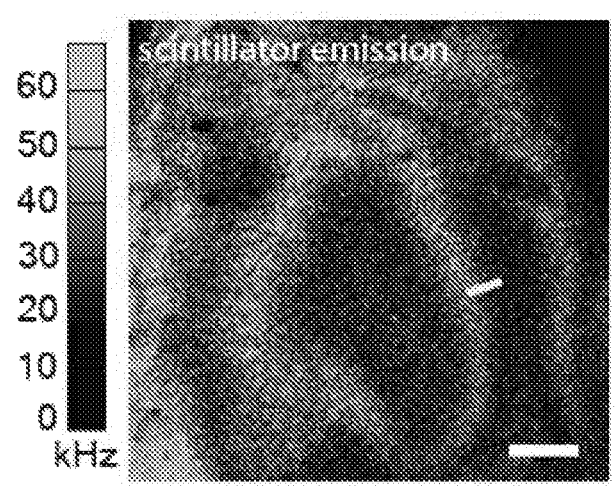
FIG. 18A is a nanoscale image of an organic polymer sample, generated from YAP:Ce CL emission. The diagonal line indicates a line-cut across the image. The scale bar represents 1.0 µm.
Figure 18B:
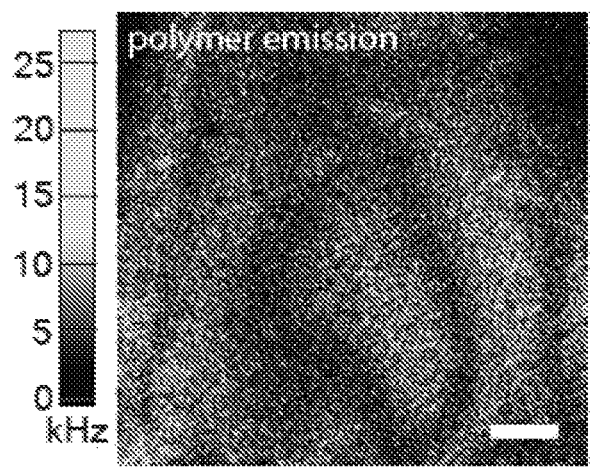
FIG. 18B is a nanoscale image of an organic polymer sample, generated from polymer luminescence. The scale bar represents 1.0 µm.

Imaging of the polymer sample was performed as described above. The emission from PFO was recorded in parallel. The image obtained from CL of the YAP:Ce illumination layer is shown in FIG. 18A. The scale bar in the lower right corner represents 1.0 µm. The diagonal white line represents a line-cut of the image. The image obtained from PFO emission is shown in FIG. 18B. The scale bar in the lower right corner represents 1.0 µm.

Figure 18C:
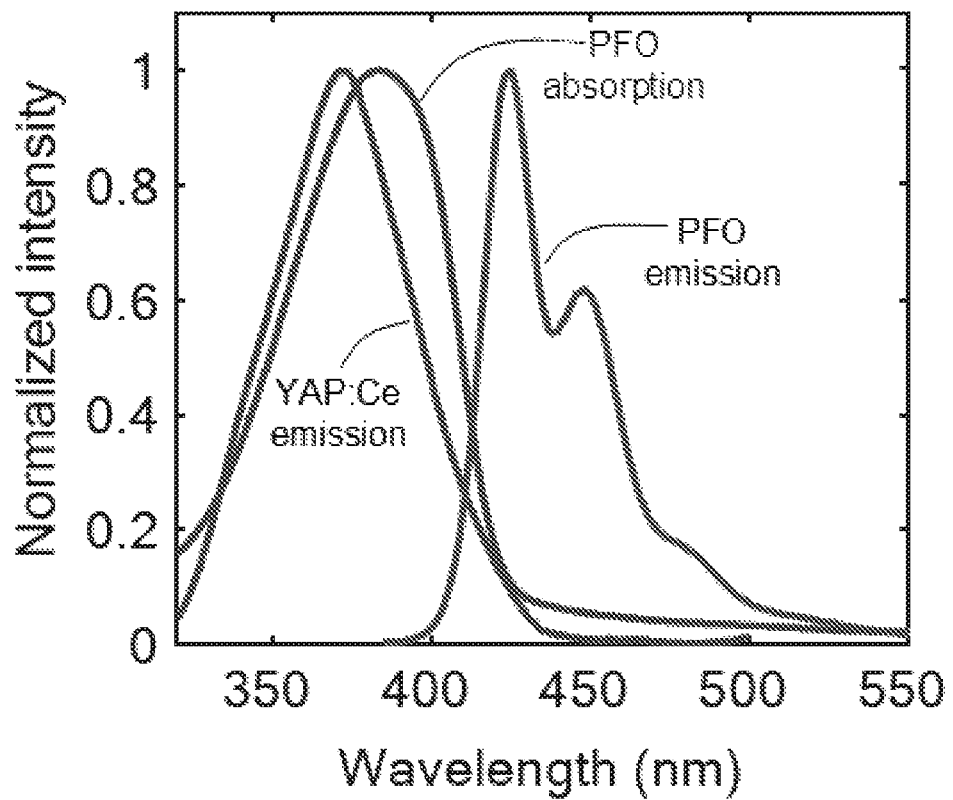
FIG. 18C is a graph depicting the CL emission spectrum of a YAP:Ce scintillator film, the phospholuminescence (PL) emission spectrum of polyfluorene (PFO), and the absorption spectrum of PFO.

Shown in FIG. 18C is a graph depicting the CL emission spectrum of the YAP:Ce scintillating layer, the phospholuminescence emission spectrum of the PFO polymer included in the polymer blend sample, and the absorption spectrum of the PFO polymer. As depicted, there is strong spectral overlap between the CL emission spectrum of the YAP:Ce film and the absorption spectrum of the PFO polymer, which may facilitate Förster resonance energy transfer (FRET) between the YAP:Ce film and PFO polymer.

As seen by comparing FIGS. 18A and 18B, the spatial maps of polymer and scintillator emission are anti-correlated in intensity, which is consistent with energy transfer via FRET. Areas of low CL emission in FIG. 18A appear where the scintillator film can transfer significant excitation energy to nearby PFO; the corresponding regions in the image of PFO in FIG. 18B are very bright. In contrast, high intensity YAP:Ce luminescence areas show that PFO is too far from the YAP:Ce surface for significant amounts of energy transfer to occur, and correspond to regions of low intensity in FIG. 18A.

Figure 18D:
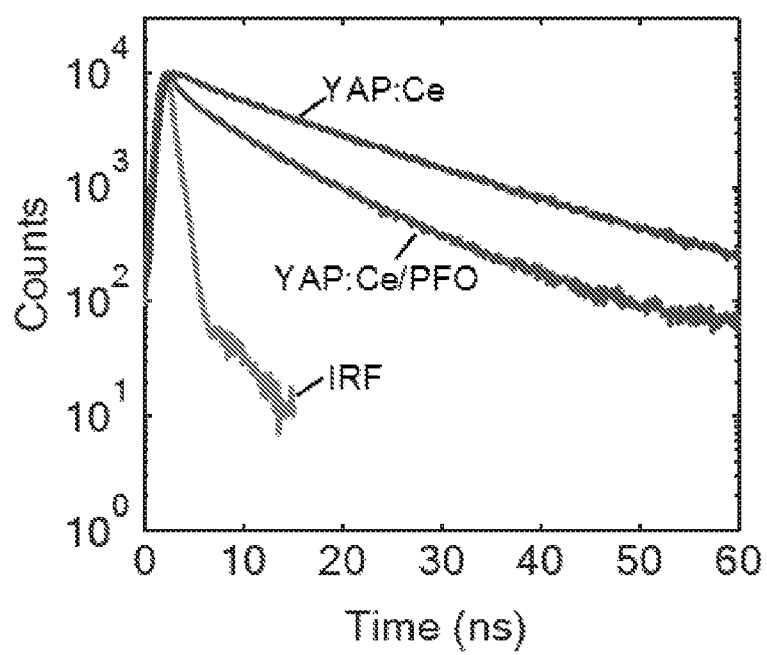
FIG. 18D is a graph of the fluorescence lifetime of a YAP:Ce scintillator film in the presence and absence of an organic polymer sample containing PFO.

Depicted in FIG. 18D is a graph of fluorescence lifetime of the YAP:Ce scintillator film in the presence and absence of the PFO polymer. The YAP:Ce lifetime is reduced from 16.5 ns to 10.2 ns when PFO is applied to the surface.

Figure 18E:
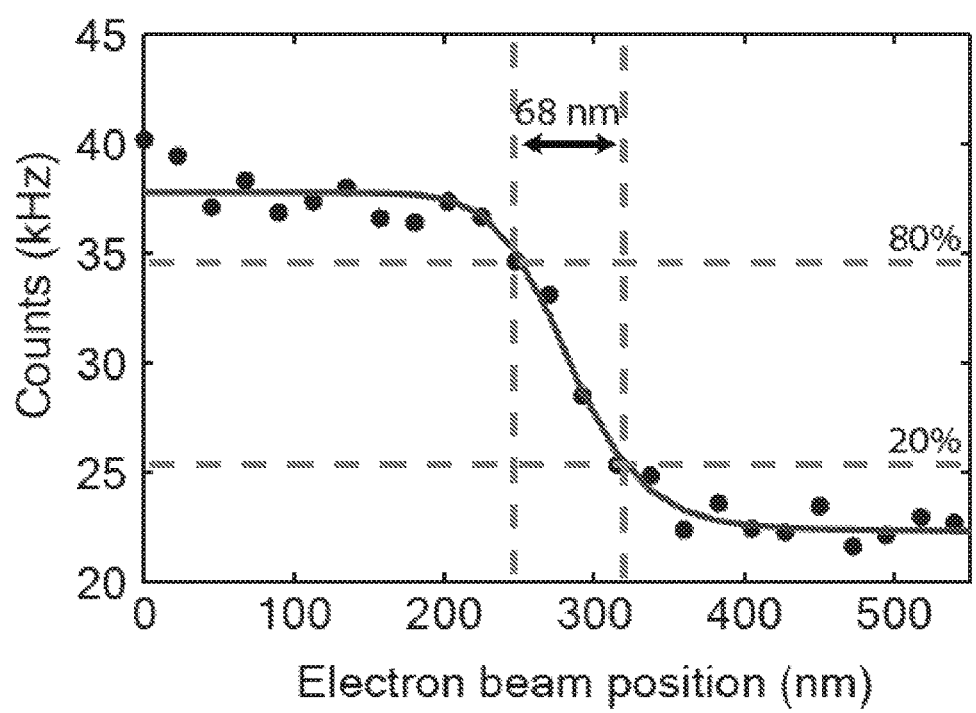
FIG. 18E is a graph of the CL emission detected across a line-cut of a nanoscale image of an organic polymer sample.

Depicted in FIG. 18E is a graph of the emission detected across the line-cut shown in the middle right-hand side of the image in FIG. 18A. The difference in electron beam position when 80% of the maximum luminescence was detected compared to 20% is 68 nm, which is below the diffraction limit and consistent with a near-field interaction between the scintillator and the polymer film.

In the CL-activated imaging of the luminescent polymer, typical count rates indicated in the scale bars for images in FIGS. 18A and 18B are approximately 50 kHz and 15 kHz, respectively. Assuming the same 7% variation in counts per pixel obtained by the image analysis described in Example 4, the shot noise in FIGS. 18A and 18B is estimated to be approximately 40% and 80%, respectively, with respective detected counts per pixel of approximately 5 and 1.5. Therefore in these images, the shot noise ultimately limits the signal-to-noise ratio. Because the dwell time per pixel used in these images was 0.1 ms, scanning more slowly may improve the signal-to-noise ratio and improve the resolution. The overall frame rate of imaging could also be maintained by selecting a smaller region of interest.

Example 9

Determining Relationship Between Image Brightness, Sample Damage, and Image Resolution This Example demonstrates how the optimal range of electron beam accelerating voltage for imaging with a YAP:Ce film can be quantitatively determined by measuring the electron current leaking through the illumination layer in relation to scintillator brightness saturation limit.

A $SrTiO_3/LaAlO_3$/YAP:Ce film was prepared following a similar procedure to the one described in Example 1.

Figure 19A:
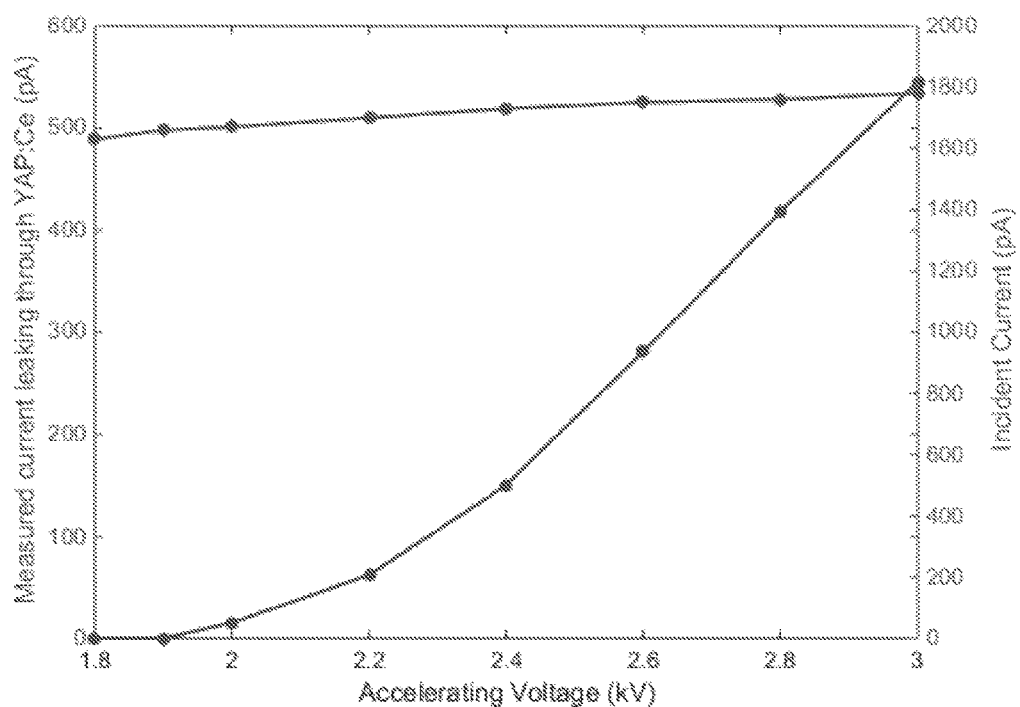
FIG. 19A is a plot of the electron current measured through a free-standing $SrTiO_3/LaAlO_3/YAP:Ce$ film (bottom trace) and the incident current (top trace) as a function of the accelerating voltage.

The electron current leaking through a free-standing $SrTiO_3/LaAlO_3$/YAP:Ce film for a range of accelerating voltages was measured using an incident beam current analogous to that used during CL-activated imaging, as shown by the bottom line in FIG. 19A. At each value of the accelerating voltage, the current was monitored through the stage of the SEM while the YAP:Ce imaging chip was deliberately not grounded to the stage. As the accelerating voltage was decreased, the incident current also decreased slightly, as shown by the upper line in FIG. 19A. The number of electrons that penetrate through the scintillator film decreases as the accelerating voltage is decreased. No current was detectable below 2.0 kV. At the imaging conditions used for imaging the luminescent polymer film (1.8 kV and 1.6 nA) the leakage current through the YAP:Ce film is well below the 2 pA detection limit of the SEM current probe. Therefore, the corresponding fraction of electrons penetrating through the YAP:Ce scintillator film is smaller than the corresponding upper bound of 0.12% of the incident beam current.

Figure 19B:
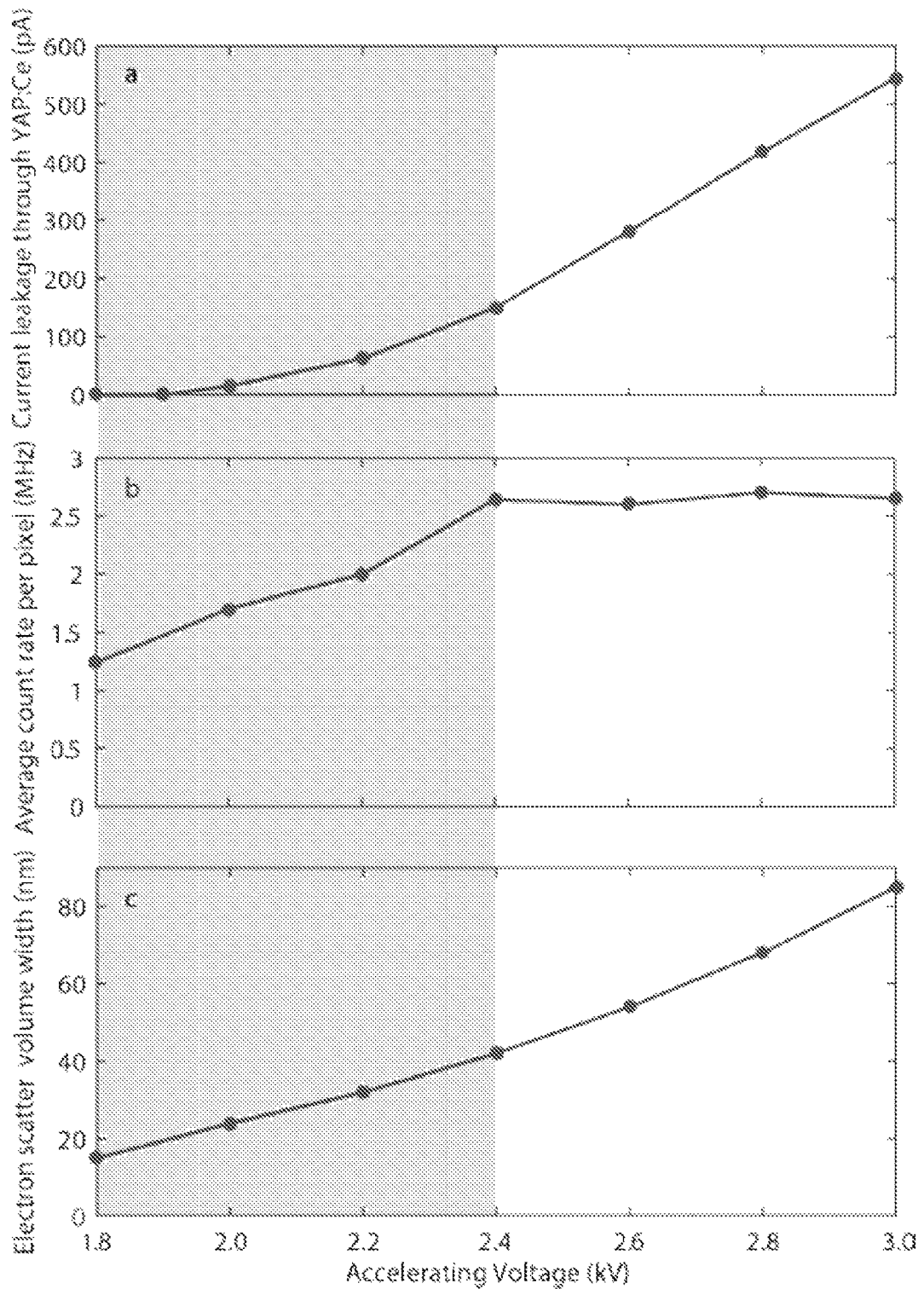
FIG. 19B are plots of the current leakage measured through a free-standing $SrTiO_3/LaAlO_3/YAP:Ce$ film (a), the brightness of YAP:Ce (b), and the electron scattering volume width (c), all as function of the accelerating voltage.

Replotting the detected leakage current through the scintillating film as a function of accelerating voltage, as shown in the top graph of FIG. 19B, and plotting on the same axes the corresponding measured film luminescence in terms of count rate, as shown in the middle graph of FIG. 19B, shows the accelerating voltage range over which the brightness of CL-activated sample imaging can be optimized. The shaded range on the graphs falls between the 1.8 kV voltage below that of minimum detectable leakage current and the 2.4 kV voltage at which the brightness of the scintillator saturates, providing a significant range over which these two parameters may be balanced as a function of the sample brightness and resilience. Exceeding the saturation voltage does not provide a brighter CL image. For resilient samples, it may be possible to allow some electron leakage in exchange for a higher rate of excitation transfer between a larger pool of $Ce^{3+}$ donors and the sample chromophores. There is also a trade-off between brightness and resolution, as evidenced by the increase in the electron scattering volume width measured in Monte Carlo simulations at a depth in the scintillator film within a Förster radius of ~5 nm from the sample, and plotted in the bottom graph of FIG. 19B. A doubling of this effective spot size from ~20 to ~40 nm occurs over the shaded accelerating voltage range in the figure. Obtaining images with an accelerating voltage closer to the scintillator brightness saturation limit may be advantageous, in which case a high density 1-2 nm electron-blocking layer between the scintillator film and the sample would be added to maximize the number of activated $Ce^{3+}$ dopants within the FRET radius while reducing sample damage.

Example 10

Preparation of YAP: Ce Films Using a Wet Etch Approach

This Example demonstrates a wet-etch method of preparing films for use in cathodoluminescence-activated imaging.

A schematic of the wet-etch process is shown in FIG. 21. Onto one side of a Si wafer was deposited $SrTiO_3$, $LaAlO_3$, and $YAlO_3$:Ce, following the procedure described in Example 1. Following deposition of the YAP:Ce film on the $LaAlO_3$ layer, plasma enhanced chemical vapor deposition (PECVD) silicon nitride (1 µm) was deposited on both sides of the chip. Using photolithography, both sides of the chip were patterned. The patterning process included spinning on positive photoresist (S1818, Microposit), masking an area of the film with a chromium mask, exposing with UV light, and developing to remove the photoresist in exposed regions (MF-319, Microposit). Once the photoresist was removed, the exposed silicon nitride layer was etched with O2/CF4 plasma, and the remaining photoresist was removed (Remover 1165, Microposit). The YAP:Ce side of the chip was patterned with an array of circles (10 µm in diameter). The Si side of the chip was patterned with square features (300 µm on a side).

ProTEK® B3 Primer and ProTEK® B3 (Brewer Science) were deposited on the YAP:Ce side of the chip to prevent damage to the YAP:Ce film during the tetramethylammonium hydroxide (TMAH) etch. ProTEK® B3 Primer was spun on and annealed at 250° C. for 15 minutes. ProTEK® B3 was spun on and annealed at 130° C. for 15 minutes and 250° C. for 45 minutes. To prevent pinholes in the ProTEK® B3 layer, a layer of polydimethylsiloxane (PDMS, Slygard® 184, Dow Corning) was deposited on top of the ProTEK® layer and cured at 120° C. for 30 minutes. The chip was then placed in a TMAH etch bath (25% TMAH) at 37° C. for 12 hours. After the silicon has been etched through to the YAP:Ce layer, the ProTEK® B3 and PDMS layers were removed (ProTEK® Remover, Brewer Science).

Figure 23:
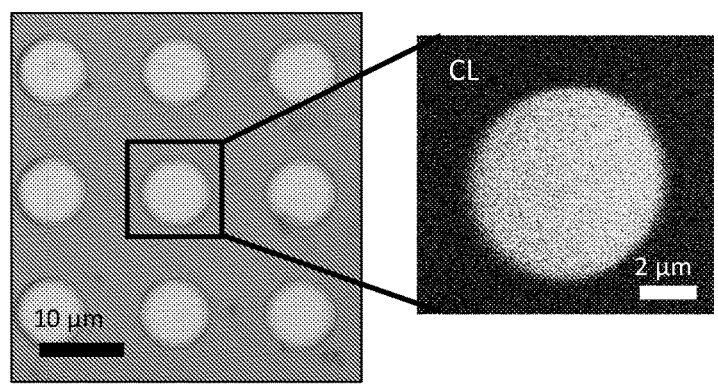
FIG. 23 is an image taken through an optical microscope of the periodic pattern of windows in an imaging chip with a YAP:Ce scintillator film illumination layer produced using a wet-etch method. The inset depicts a cathodoluminescence image of one of the windows.

Depicted in FIG. 23 is an image taken through an optical microscope of the periodic pattern of windows in an imaging chip with a YAP:Ce scintillator film illumination layer produced using a wet-etch method.

Example 11

Preparation of YAP:Ce Films Using a Dry Etch Approach

This Example demonstrates a dry-etch method of preparing films for use in cathodoluminescence-activated imaging.

A schematic of the wet-etch process is shown in FIG. 22. Onto one side of a Si wafer (200 µm, oriented [100]±0.1°) was deposited $SrTiO_3$ (3 unit cells) and $LaAlO_3$ (20 nm), following the procedure described in Example 1. The YAP: Ce film (15-20 nm) was pulsed-laser deposited on the $LaAlO_3$ layer supported by the $SrTiO_3$ on the silicon wafer. Alumina ($Al_2O_3$, 2 nm) was deposited by atomic layer deposition (Cambridge Fiji F200 Plasma ALD) on the YAP:Ce film side of the chip for protection. Subsequently, low-stress silicon nitride (SiNx, 1 µm) was deposited by plasma enhanced chemical vapor deposition (Oxford Plasmalab 80 Plus PECVD) on the same side, for protection and structural support during subsequent steps. Using photolithography, part of the silicon side of the chip was patterned with an array of square crosses (10 µm across arms); part was left intact for structural support (not shown in FIG. 22).

The patterning process included spinning on positive photoresist (S1818, Microposit), masking an area of the film with a chromium mask, exposing with UV light, and developing to remove the photoresist in exposed regions (MF-319, Microposit). The exposed silicon layer was dry etched to exhaustion with $O_2/SF_6$ plasma in a deep reactive ion etcher (Surface Technology Systems Advanced Silicon Etch) using a Bosch process; the remaining photoresist was removed (Remover PG, Microposit) and descummed with $H_2/O_2$ plasma in a reactive ion etcher (Plasma-Therm PK-12). The silicon layer was again dry etched so that the depth of the silicon wells was reduced to 10 µm, exposing the SrTiO$_3$/LaAlO$_3$/YAP:Ce film. An additional alumina layer (45 nm) was deposited on the silicon side of the chip for structural support. The silicon nitride layer was removed using with $O_2/CF_4$ plasma by reactive ion etching to reveal the SrTiO$_3$/LaAlO$_3$/YAP:Ce film.

Example 12

Cathodoluminescence-Activated Nanoimaging of Biological Materials

This Example demonstrates cathodoluminescence-activated imaging of chlorophyll-containing lipid membrane grana stacks isolated from spinach chloroplasts.

Figure 24A:
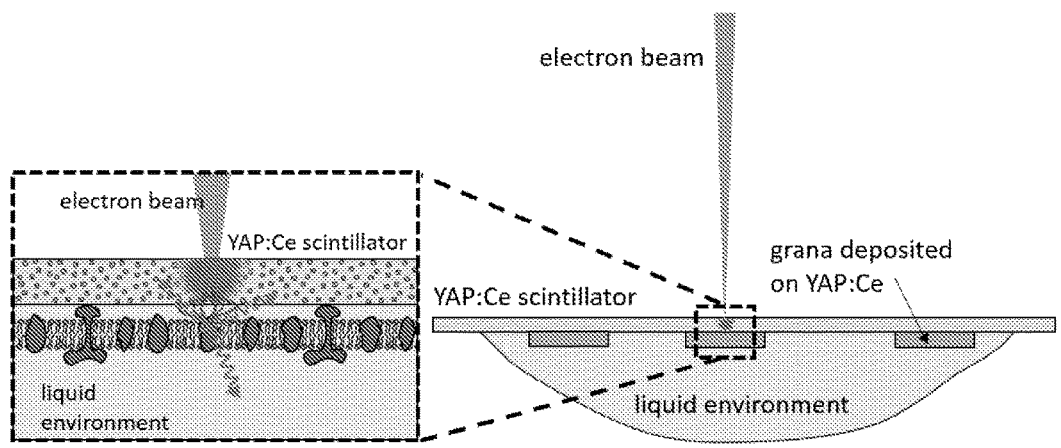
FIG. 24A is a diagram of chlorophyll-containing lipid membrane grana stacks isolated from spinach chloroplasts being imaged using a YAP:Ce scintillator.

The chip used for this Example was produced following the dry-etch method as described in Example 11 above. As measured by atomic force micrographs, the grana discs were approximately 800 nm in diameter and 20 nm tall (FIG. 24D). They were deposited on the scintillating windows of an imaging chip and covered with a droplet of 1-butyl-3-methylimidazolium hexafluorophosphate. The droplet was surrounded by the vacuum environment of the SEM.

Figure 24B:
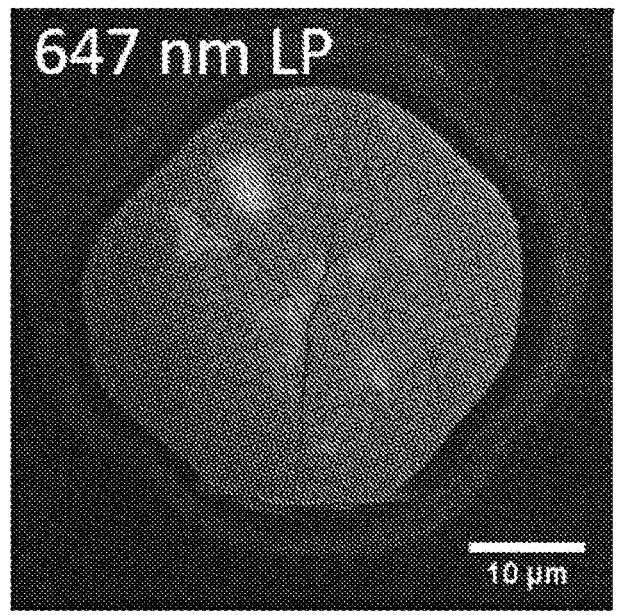
FIG. 24B depicts a cathodoluminescence image of photosynthetic membrane patches. The brighter patches indicate fluorescence at chlorophyll wavelength.

The electron beam (1.8 kV accelerating voltage) excited the scintillating illumination layer to obtain the cathodoluminescence-activated image shown in FIG. 24B. Chlorophyll fluorescence was observed from the underlying biological sample, indicated as brighter patches in the image. Luminescence was not observed in other wavelength ranges examined throughout the visible range, which suggests that FRET may be the mechanism that generates imaging contrast. At 1.8 kV, electrons do not directly excite the biological sample. Depicted in FIG. 24A is a scheme of chlorophyll-containing lipid membrane grana stacks isolated from spinach chloroplasts being imaged using a YAP:Ce scintillator.

Figure 24C:
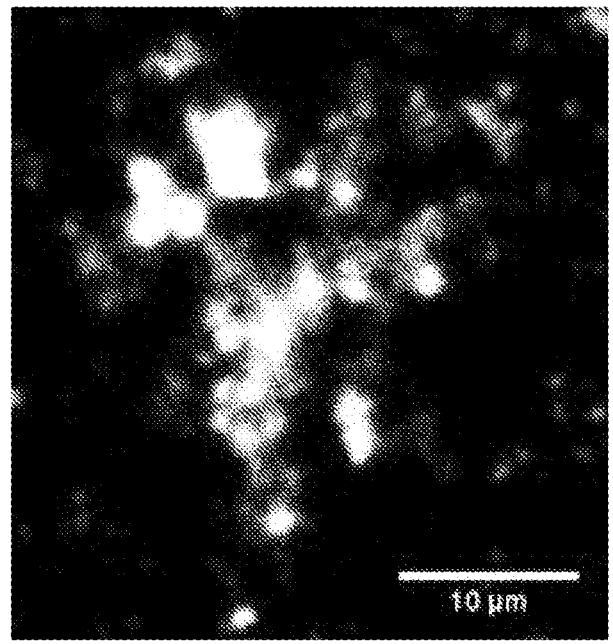
FIG. 24C depicts an image of photosynthetic membrane patches taken using confocal fluorescence microscopy. The brighter patches indicate fluorescence at chlorophyll wavelength.
Figure 24D:
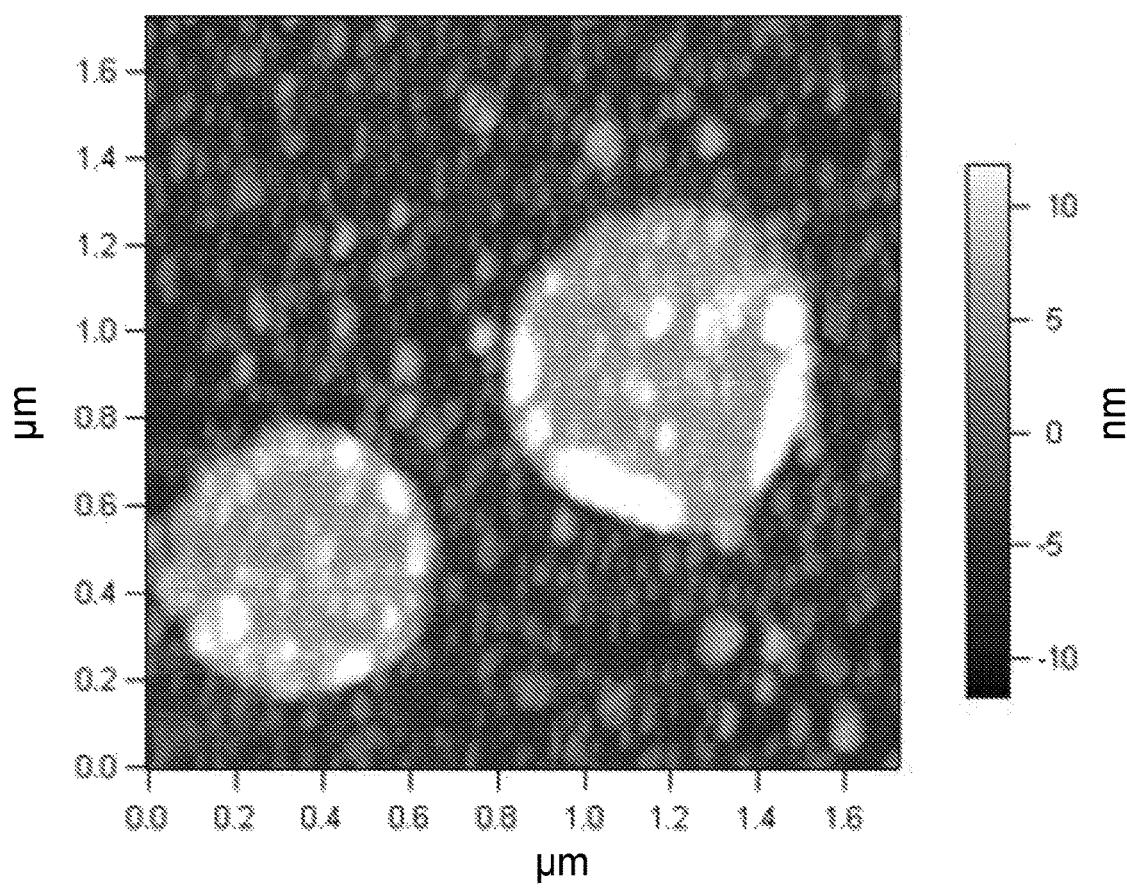
FIG. 24D depicts an atomic force micrograph of chlorophyll-containing lipid membrane grana stacks isolated from spinach chloroplasts.

The pattern observed using this CL-activated imaging matched the chlorophyll fluorescence pattern observed on the same sample imaging chip taken using confocal fluorescence microscopy (FIG. 24C). This observation demonstrates the ability to image biological materials non-invasively using this new approach.

Example 13

Cathodoluminescence-Activated Nanoimaging of Metal Particles in Vacuo and Dynamically in Liquid This Example demonstrates cathodoluminescence-activated imaging of polyvinylpyrrolidone (PVP)-coated 100 nm silver nanoparticles in a liquid environment and in vacuo.

The imaging chip used for this Example was produced following the wet-etch method as described in Example 10 above. The metal particles were deposited on the YAP:Ce face of the imaging chip.

Figure 25A:
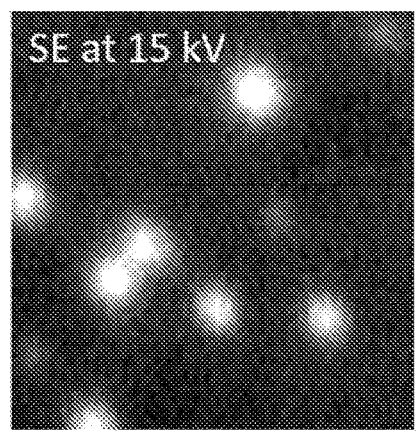
FIG. 25A depicts a secondary electron (SE) image of polyvinylpyrrolidone (PVP)-coated 100-nm silver nanoparticles deposited on the bottom face of a scintillating illumination layer, obtained using an accelerating voltage of 15 kV. The image was obtained in a 1.5 µm×1.5 µm region of interest.

Imaging in vacuo: Shown in FIG. 25A is a secondary electron (SE) image obtained in a 1.5 µm×1.5 µm region of interest. This image was obtained using an accelerating voltage of 15 kV, such that the electrons in the beam passed through the illumination layer and directly impacted the sample beads, generating contrast through secondary electrons scattering off of the metal particles. This image does not employ CL-activated imaging.

Figure 25B:
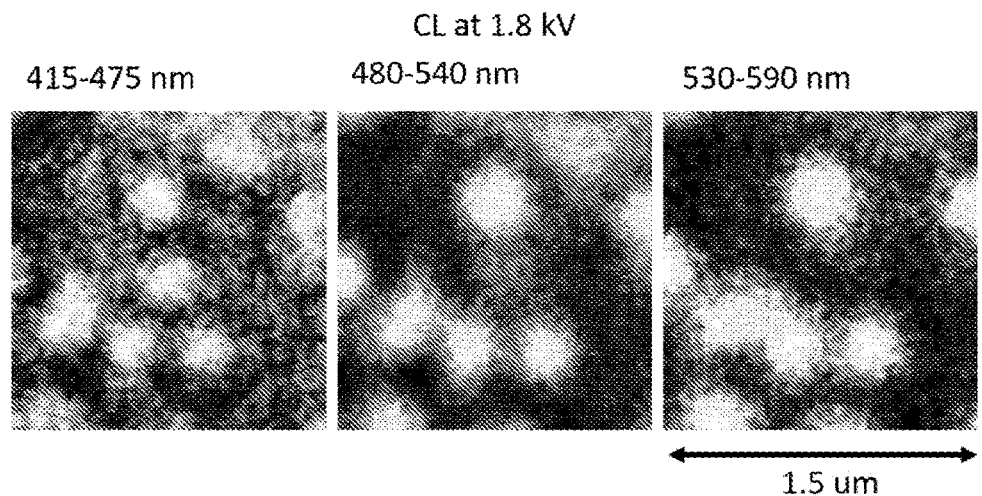
FIG. 25B depicts three correlated sub-diffraction CL-activated images of PVP-coated 100-nm silver nanoparticles deposited on the bottom face of a scintillating illumination layer, obtained using an accelerating voltage of 1.8 kV.

Shown in FIG. 25B are three correlated images taken with sub-diffraction CL-activated imaging using the lower accelerating voltage of 1.8 kV. The three images show a wavelength dependence. The bright features in the SE image of FIG. 25A, each representing a single particle, are all reproduced in the CL-activated images of FIG. 25B. Some particles that appear dim in SE are bright in the CL-activated images. The contrast in CL-activated images may result from near-field interactions between the luminescent emitters (Ce ions) in the YAP:Ce scintillator illumination layer and the conduction electrons in the metal particles, often described as plasmonic. At the emission wavelengths detected in these three images, the particles have higher intensity luminescence compared to the background level. At other wavelengths a suppression of luminescence at the particle positions has been observed, which may enable their detection.

Imaging dynamically in liquid: A droplet of 1-butyl-3-methylimidazolium hexafluorophosphate was applied to the sample of metal particles deposited on the chip. The presence of the liquid changes the index of refraction of the medium surrounding the sample, which may affect the luminescence and the near-field interaction between the sample and the illumination layer.

The scheme in FIG. 26 depicts the imaging configuration, with a droplet of ionic liquid solubilizing the metal particles and the electron beam incident on an imaging window in the imaging chip (the silicon nitride support grid on the YAP:Ce face is not shown). The particles are coated or suspended in a droplet of fluid that "hangs" from the underside of the scintillating film. The light collection apparatus is not shown in this schematic. Low (a few kV) accelerating voltages were employed so that the illumination layer was excited directly, while the liquid beneath it was not.

Figure 27:
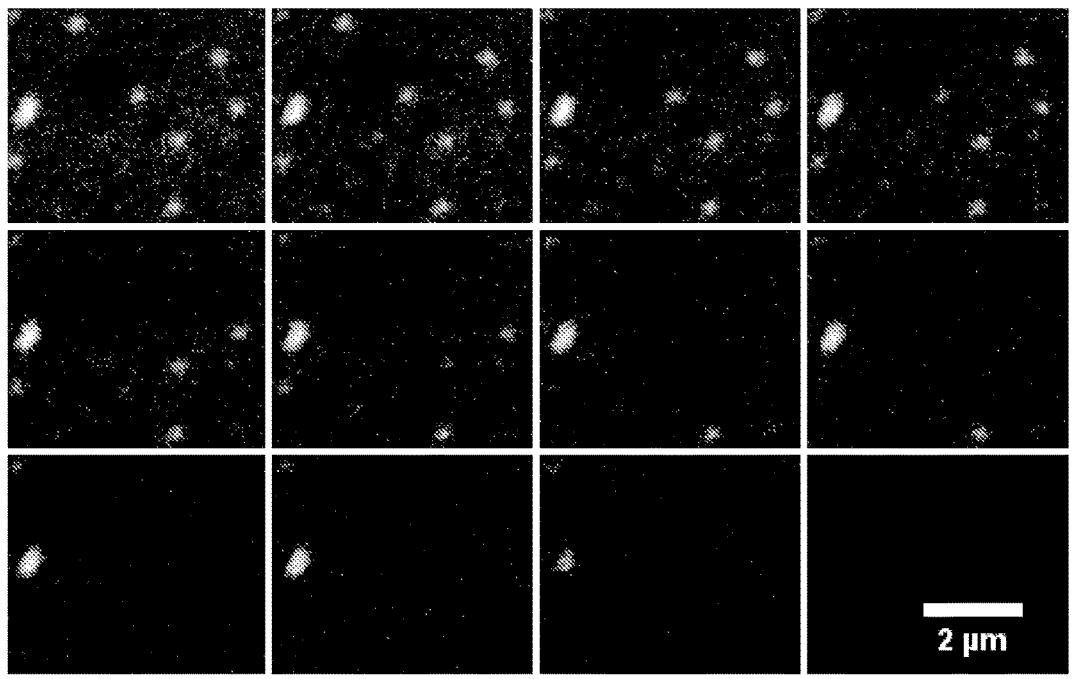
FIG. 27 depicts a series of cathodoluminescence-activated nanoimages of metal particles in a droplet of liquid on the bottom face of a scintillating illumination layer, with an electron beam incident on a window of the imaging chip above.

In this imaging geometry, a single region of interest was observed by imaging a frame every 10 seconds. Shown in FIG. 27 is a sequence of images, beginning at the top left and proceeding from left to right, top to bottom. The bright spots each correspond to PVP-coated silver nanoparticles. It was observed that as a function of time, the nanoparticles desorb from the illumination layer surface until none remain. This observation demonstrates the ability to follow the same nanoscale objects with sub-diffraction spatial resolution during a dynamic process.

Example 14

Cathodoluminescence-Activated Nanoimaging of Luminescent Polymer Particle Motion in Liquid This Example demonstrates the ability to observe the time evolution of the lateral position of a soft material in liquid.

The imaging chip used for this Example was produced following the wet-etch method as described in Example 10 above. The particles composed of PFO and F8BT were suspended in a droplet of Edwards Ultragrade 19 oil on the YAP:Ce face of the imaging chip.

Figure 28:
FIG. 28 depicts a set of cathodoluminescence-activated nanoimages of luminescent polymer particle motion in an oil droplet.

FIG. 28 depicts a set of cathodoluminescence-activated images obtained over time of the polymer particles. In these frames, a polymer particle is observed to dock on the bottom surface (YAP:Ce face), to travel along the surface and to undock This observation demonstrates the ability to observe a dynamic event in a liquid using near-field FRET as a means to generate contrast, as the luminescence of the PFO polymer is registered.

What is claimed is:

1. A system for imaging a sample, comprising:
an illumination layer;
a sample,
   wherein the sample is positioned below the illumination layer;
an electron beam source,
   wherein the electron beam source is positioned above the illumination layer, and is configured to contact multiple locations of the illumination layer with an electron beam, and
   wherein the illumination layer is configured to emit photons when excited by contact with the electron beam;
an optical detector,
   wherein the optical detector is configured to receive at least a portion of the photons emitted by the illumination layer,
   wherein the at least a portion of the photons emitted by the illumination layer and received by the optical detector are located above the illumination layer; and
a signal correlation device,
   wherein the signal correlation device is connected to the optical detector and the electron beam source, and is configured to correlate the photons received by the optical detector with the multiple locations of the illumination layer contacted with the electron beam to produce an image of the sample.

2. The system of claim 1, wherein the electron beam source is configured to contact multiple locations of the illumination layer with an electron beam without contacting the sample with the electron beam.

3. The system of claim 1, wherein the illumination layer has an optical near-field of 10 nm or less, and wherein the sample is located within the optical near-field of the illumination layer.

4. The system of claim 1, further comprising a parabolic mirror to direct the at least a portion of the photons emitted by the illumination layer to be received by the optical detector.

5. The system of claim 1, wherein the illumination layer comprises $YAlO_3$ and $Ce^{3+}$.

6. The system of claim 5, wherein the illumination layer is between 5 nm and 20 nm thick.

7. The system of claim 1 wherein the sample comprises a biological molecule, a liquid, a soft material, or any combinations thereof.

8. The system of claim 1, wherein the system is configured to image the sample over time, and produce a plurality of images of the sample sequentially over a period of time.

9. A method for imaging a sample, comprising:
(i) producing an electron beam from an electron beam source;
(ii) contacting multiple locations of an illumination layer with the electron beam,
   wherein the electron beam source is located above the illumination layer,
   wherein a sample is located below the illumination layer,
   wherein the contacting of the illumination layer with the electron beam excites least a portion of the illumination layer without exciting the sample, and
   wherein at least a portion of the excited illumination layer emits photons;
(iii) detecting at least a portion of the photons emitted by the excited illumination layer,
   wherein the detected photons are located above the illumination layer; and
(iv) correlating at least a portion of the detected photons with the multiple locations of the illumination layer contacted with the electron beam to produce an image of the sample.

10. The method of claim 9, wherein the illumination layer comprises $YAlO_3$ and $Ce^{3+}$.

11. The method of claim 10, wherein the illumination layer is between 5 nm and 20 nm thick.

12. The method of claim 9, wherein the sample comprises a biological molecule, a liquid, a soft material, or any combinations thereof.

13. The method of claim 9, wherein (ii) through (iv) are repeated to produce one or more additional images of the sample sequentially over a period of time.

14. An image produced by the method of claim 9.

15. The image of claim 14, wherein the image has a spatial resolution, and the spatial resolution is less than 50 nm.

16. An imaging chip, comprising:
an illumination layer,
   wherein the illumination layer is configured to be contacted by an electron beam produced from an electron beam source positioned above the illumination layer, become excited by contact with the electron beam, and emit photons when excited;
a frame layer,
   wherein the frame layer is configured to provide structural support, is positioned above the illumination layer, and has an imaging window through which an electron beam passes to contact the illumination layer without contacting the frame layer; and
a buffer layer,
   wherein the buffer layer is positioned between the frame layer and the illumination layer.

17. The imaging chip of claim 16, further comprising a sample layer, wherein the sample layer is configured to hold a sample and is positioned below the illumination layer.

18. The imaging chip of claim 17, wherein the sample layer further comprises a sample.

19. The imaging chip of claim 16, wherein the illumination layer comprises $Ce^{3+}$ and $YAlO_3$.

20. The imaging chip of claim 19, wherein the illumination layer is between 5 nm and 20 nm thick.

21. The imaging chip of claim 20, wherein at least a portion of the illumination layer is not contacted by the frame layer.

22. The imaging chip of claim 16, wherein the frame layer comprises Si.

23. The imaging chip of claim 16, further comprising an additional buffer layer, wherein the additional buffer layer is positioned between the buffer layer and the frame layer, the buffer layer comprises $LaAlO_3$, and the additional buffer layer comprises $SrTiO_3$.

* * * * *